United States Patent [19]
Johnson

[11] Patent Number: 5,196,542
[45] Date of Patent: Mar. 23, 1993

[54] CYCLIC HYDROCARBONS WITH AN AMINOALKYL SIDECHAIN

[75] Inventor: Roy A. Johnson, Kalamazoo, Mich.

[73] Assignee: The Upjohn Company, Kalamazoo, Mich.

[21] Appl. No.: 657,721

[22] Filed: Feb. 20, 1991

Related U.S. Application Data

[60] Division of Ser. No. 394,396, Aug. 15, 1989, which is a division of Ser. No. 117,851, Jun. 16, 1987, Pat. No. 4,917,826, which is a continuation-in-part of Ser. No. 843,120, Mar. 24, 1986, abandoned, which is a continuation-in-part of Ser. No. 788,995, Oct. 18, 1985, abandoned.

[51] Int. Cl.$^5$ .................. C07D 213/38; C07D 313/50; A61K 31/58; A61K 31/44
[52] U.S. Cl. .................................. 546/326; 546/333; 564/460; 540/107
[58] Field of Search .................. 546/329, 333; 364/460

[56] References Cited

U.S. PATENT DOCUMENTS 3,284,475 11/1966 Klimstra.
3,370,070 2/1968 Klimstra et al..
4,239,780 12/1980 Wallach.

OTHER PUBLICATIONS

Vogt, W., "Role of Phospholipase A2 is Prostaglandin Formation", Advances in Prostaglandins and Thromboxane Research, 3, p. 89 (1978).
Isakson, P. C. et al., "Lipases and Prostaglandin Biosynthesis", Advances in Prostaglandin and Thromboxane Research, 3, p. 113, (1978).
Plummer, N. A., et al., "Activation of the Arachidonate Cascade in Human Skin Inflamed by Irradiation with UVC and the Effects of Indomethacin", abstracted in Journal of Investigative Dermatology, 68, p. 246 (1977).
Vargaftig, B. B., "Carrageenan and Thrombin Trigger Prostaglandin Synthetase-Independent Aggregation of Rabbit Platelets: Inhibition by Phospholipase A2 Inhibitors", J. Pharm. Pharmacol., 29, pp. 222-228.

Flower, R. J. and Blackwell, G. J., "Anti-Inflammatory Steroids Induce Biosynthesis of a Phospholipase A2 Inhibitor Which Prevents Prostaglandin Generation", Nature, 278, pp. 456-459 (1979).
Kaplan, K. L., et al., "Low Concentrations of Indomethacin Inhibit Phospholipase A2 of Rabbit Polymorphonuclear Leukocytes", Proc. Natl. Acad. Sci., 75, pp. 2955-2988 (1978).
Vallee, E., et al., "Anti-Inflammatory and Platelet Anti-Aggregant Activity of Phospholipase-A2 Inhibitors", J. Pharm. Pharmacol., 31, pp. 588-592 (1974).
Roberts, M. F., et al., "Chemical Modification of the Histidine Residue in Phospholipase A2", J. of Biol. Chem., 252, pp. 2405-2411 (1977).
Blackwell, G. J., et al., "Phospholipase A2 Activity of Guinea-Pig Isolated Perfused Lungs: Stimulation, and Inhibition by Anti-Inflammatory Steroids", British J. Pharmacy, 62, pp. 79-89 (1978).
Wallach, D. P. and Brown, V. J. R., "Studies on the Arachidonic Acid Cascade-I", Bioch. Pharmacol., 30, pp. 1315-1324 (1981).
Doctoral Thesis, L. J. Griggs, "Part I. Synthetic Approaches to 6- and 16-Thiaestrone. Part II. Estrone with a Diazacholesterol Side Chain," University of Michigan (1965).
Klimstra, P. D., et al., "Hypocholesterolemic Agents. VI. A- and B-Ring-Modified Azacholesterols", J. Med. Chem., 9, pp. 323-326 (1966).

Primary Examiner—Robert T. Bond
Attorney, Agent, or Firm—Debbie K. Wright; Thomas A. Wootton

[57] ABSTRACT

Provided are cyclic hydrocarbons of Formula I

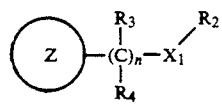

with an aminoalkyl sidechain that are useful for treating phospholipase A2 mediated conditions, diabetes, and obesity.

3 Claims, No Drawings

CYCLIC HYDROCARBONS WITH AN AMINOALKYL SIDECHAIN

CROSS REFERENCE TO RELATED APPLICATIONS

This application is a division of application Ser. No. 07/394,396, filed Aug. 15, 1989, still pending, which is a division of application Ser. No. 07/117,851, filed Jun. 16, 1987, now U.S. Pat. No. 4,917,826, which is a continuation-in-part of patent application Ser. No. 06/843,120, filed Mar. 24, 1986, now abandoned, which is a continuation-in-part of patent application Ser. No. 06/788,995, filed Oct. 18, 1985, now abandoned.

FIELD OF INVENTION

This invention relates to novel compositions of matter. More particularly, the invention relates to cyclic hydrocarbons with an aminoalkyl sidechain that are useful for inhibiting phospholipase A2 and for treating diabetes and obesity.

INFORMATION DISCLOSURE

The important role of phospholipase A2 in mamalian metabolism through the formation of prostaglandins is now well known. See W. Vogt, Advances in Prostaglandins and Thromboxane Research, 3, p. 89 (1978); P. C. Isakson, et al., Advances in Prostaglandin and Thromboxane Research, 3, page 113, (1978). Phospholipase A2 is responsible for the hydrolysis of arachidonic acid-containing phospholipids, thereby providing substrate for the multiple enzymes of the arachidonic acid cascade.

The products of the arachidonic acid cascade are varied. These products include prostaglandins, thromboxanes, leukotrienes, and other hydroxylated derivatives of arachidonic acid. All of the foregoing are referred to as "eicosanoids." While generally the products of the cascade are beneficial, in certain disease processes and other conditions the excessive production of eicosanoids induces deleterious consequences such as inflammation (see paper by N. A. Plummer, et al.; abstracted in Journal of Investigative Dermatology, 68, p. 246 (1977)); erythema (N. A. Plummer, supra); platelet aggregation (B. B. Vargaftig, J. Pharm. Pharmacol., 29, pp. 222-228 (1977)); and the release of SRS-A (slow reacting substance-anaphylaxis), a known mediator of allergic responses. The inhibition of phospholipase A2 prevents these and similar conditions mediated by the action of this enzyme.

Some inhibitors of phospholipase A2 are known. R. J. Flower and G. J. Blackwell have shown that certain anti-inflammatory steroids induce biosynthesis of a phospholipase A2 inhibitor which prevents prostaglandin generation. See Nature, 278, p. 456 (1979). These steroids are not direct inhibitors of phospholipase A2, but rather stimulate the synthesis of a phospholipase inhibiting factor called lipocortin, lipomodulin, or macrocortin.

Some examples of direct phospholipase A2 inhibition are known. Indomethacin, a drug with anti-inflammatory properties, has been shown to inhibit phospholipase A2 enzymes. See K. L. Kaplan, et al., Proc. Natl. Acad. Sci., 75, pp. 2955-2988 (1978).

Indomethacin has been shown to inhibit phospholipase A2 enzymes, isolated respectively from the venoms of Russell's Viper, Crotalus adamanteus, and bee, and from pig pancreas. Certain local anesthetics have been shown to inhibit phospholipase A2 activity by competing with calcium ion, which appears to be a requirement for phospholipase activity. See W. Vogt, Advances in Prostaglandin and Thromboxane Research, 3, p. 89 (1978) and E. Vallee et al., J. Pharm. Pharmacol., 31, pp. 588-92 (1974). Bromphenacyl bromide has been shown to inhibit phospholipase A2 by acylating a histidine residue which is at the active site of the enzyme. See M. Roberts, et al., J. of Biol. Chem., 252, pp. 2405-2411 (1977). R. Blackwell, et al., British J. Pharmacy, 62, p. 79-89 (1978) has disclosed that mepacrine inhibits the activity of phospholipase A2 derived from perfused guinea pig lung. Certain butyrophenones are disclosed as phospholipase A2 inhibitors in U.S. Pat. No. 4,239,780. D. P. Wallach and V. J. R. Brown, Bioch. Pharmacol., 30, pp. 1315-24 (1981) also refer to several compounds that inhibit phospholipase A2.

Some of the steroids employed for synthesizing compounds of the present invention and useful in some of the methods of treatment are known. See the doctoral thesis, L. J. Griggs, "Part I. Synthetic Approaches to 5-and 16-Thiaestrone. Part II. Estrone with a Diazacholesterol Side Chain," University of Michigan (1965). These compounds are stated therein to be potential hypocholesterolemic agents. U.S. Pat. No. 3,370,070 discloses similar steroid compounds which are useful as hypocholesterolemic agents and as antibacterial, antiprotozoal, and anti-algal agents.

Some of the steroidal compounds herein are also referred to in U.S. Pat. No. 3,284,475 and in P. D. Klimstra, et al., "Hypocholesterolemic Agents. VI. A- And B-Ring-Modified Azacholesterols", J. Med. Chem. 9, pp. 323-26 (1966).

The present invention also relates to antidiabetic agents. Hyperglycemia refers to a condition commonly found in patients suffering from mature-onset diabetes mellitus and other diseases in which impairment of pancreatic function is a consequence thereof. Accordingly, hyper-glycemic patients are those exhibiting elevated serum glucose levels. Failure to adequately control such elevated serum glucose levels has been associated in such patients with untoward cardiovascular effects (myocardioischemia, stroke, and peripheral vascular diseases), lethargy, coma, blindness, kidney failure and even death.

While conventional treatment for these hyperglycemic conditions may include diet (e.g. restriction of carbohydrate intake) and insulin injection, one important means of treating such patients is with oral antidiabetic agents such as those disclosed herein.

SUMMARY OF THE INVENTION

The present invention relates to cyclic hydrocarbons of formula I wherein: A compound of the formula

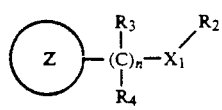

wherein:
(I) Z is

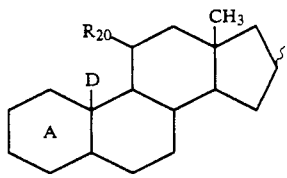

wherein 
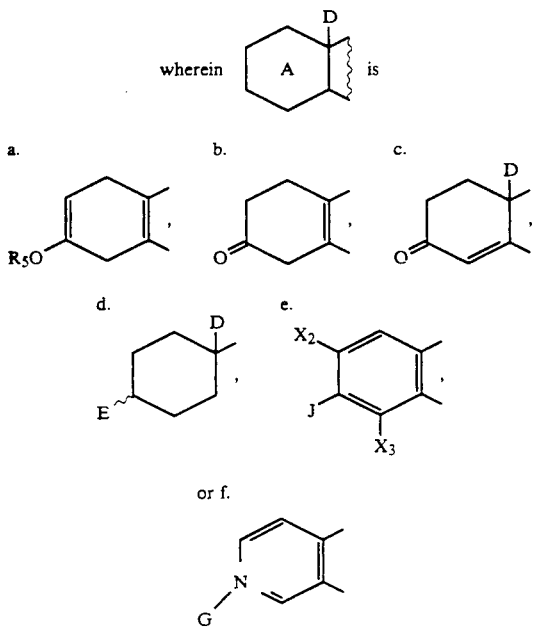

(1) wherein D is
(a) H, (b) CH₃, or (c) no bond;
(2) wherein E and J are
(a) H, (b) R₅O—, or (c) —N(CH₃)—(CH₂)₃—N(CH₃)₂ with the provisos that when E is H, the 5,6 bond is saturated and that when J is H, X₂ and X₃ are H;
(3) wherein G is
(a) nothing, or (b) →O;
(4) wherein R₅ is
(a) H, (b) C1-C3 alkyl, (c) benzyl, (d) acyl, (e) C(O)H, (f) HOCH₂CH(OH)CH₂, (g) R₄—OC—(O)CH₂;
(5) wherein X₂ and X₃ are
(a) H, (b) NO₂, (c) NH₂, (d) OH, or (e) halogen;
A. C8-C20 cycloalkyl, C. 2- or 4-cyclohexylcyclohexyl, D. 4-bicyclohexylcyclohexyl, E. 4-bicyclohexenylcyclohexyl, F. 3-cyclopentylcyclopentyl, G. 1-, 3- or 4-(2-decahydronaphthyl)cyclohexyl, H. 1- or 2-tetradecahydroanthracenyl, I. 2- or 3-tetradecahydrophenanthrenyl, J. 1- or 2-dodecahydro-1H-phenallyl, K. 1- or 2 hexadecahydropyrenyl, L. 1- or 2-octadecahydrotriphenylenyl, M. 1- or 2-octadecahydrochrysenyl, N. 1-or 2-octadecahydronaphthacenyl, O. phenylcyclohexyl, P. adamantyl, Q. pyrenyl, R. 3-fluorobiphenylyl, or S. 1- or 2-decalinyl;
II. wherein X₁ is
A. NR₁, B. NR₁R₁₃, C. N⁺.R₁.R₁.R₁₃ X⁻, or D. —O—C(O)—CH((CH₂)₃— NH₂)(NH₂);
  1. wherein X⁻ is a pharmaceutically acceptable anion;
  2. wherein R₁₃ is
    a. methyl, or b. →O;
  3. wherein R₁ is
    a. H, b. —CHO, c. —COCH₃, d. C1-C6 alkyl, e. —(CH₂)ᵣ— CO₂R₄, f. —CH₂CH=CH₂, g. —(CH₂)ₚ—X₄, h. —(CH₂)ₘ— N(R₆)(R₇), i. —(CH₂)ₚ—O(CH₂)ₚ—N(R₆)(R₇), j. —(CH₂)ₚ——Y—C(=NH)—NH₂, k. —(CH₂)q—CH(NH₂)—COOR₁₆, l. —(CH₂)ₚ—N=C(R₁₄) (R₁₅), m. —(CH₂)ₚ—NH—C(CH₃)₂—CH₂—CH₃,

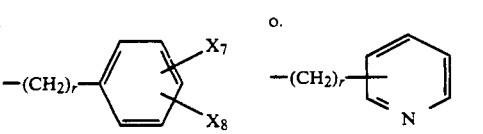

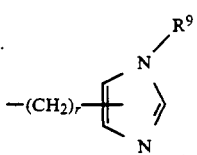

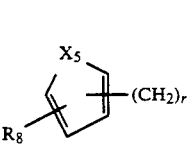

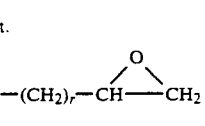

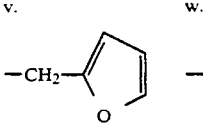

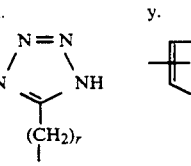

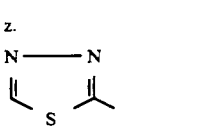

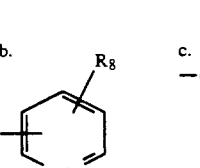

(1) wherein R₄ is
(a) H, or (b) C1-C2 alkyl;
(2) wherein X₄ is
(a) OH, (b) OCH₃, (c) OC₂H₅, (d) OCH₂CH₂OH, (e) OTs, (f) OMs, (g) Cl, (h) Br, (j) aziridinyl, or $$\begin{array}{c} N^+(CH_3)_2 \\ | \\ R_{12} \end{array} X^-$$

i) wherein R$_{12}$ is
  ii)(a) C1-C2 alkyl, ii)(b) benzyl,
  ii)(c) CH$_2$Cl, ii)(d) →O, ii)(e) CH$_2$COOC$_2$H$_5$,
  or ii)(f) C3-C18 straight chain alkyl;
(3) wherein R$_6$ is
  (a) H, (b) C1-C13 alkyl, (c) benzyl, (d) phenyl, (e) —(CH$_2$)$_p$—N(R$_{10}$)(R$_{11}$), (f) C(O)CH$_3$, (g)

(g) —(CH$_2$)$_p$—N⟨X$_6$⟩

(h) [6-methyl-3-nitropyridine], or (i) [4-aminotoluene]

i) wherein R$_{10}$ and R$_{11}$ are
    i)(a) H, i)(b) C1-C2 alkyl, or i)(c) (CH$_2$)$_3$—NH$_2$;
  ii) wherein R$_{10}$ and R$_{11}$ together are (ii)(a) [pent-2-ene-1,5-dione], or [pentane-1,5-dione]

(4) wherein R$_7$ is
  (a) H, (b) C1-C2 alkyl, (c) —(CH$_2$)$_p$—N(R$_{10}$)(R$_{11}$), or (d) CHO;
(5) wherein R$_6$ and R$_7$ together are (a) ⟨(CH$_2$)$_q$—X$_6$—(CH$_2$)$_q$⟩ i) wherein X$_6$ is
    i)(a) O, i)(b) NH, i)(c) NCH$_3$, or i)(d) N(CH$_2$)$_q$NH$_2$;

(b) [pent-2-ene-1,5-dione], or (c) [hexane-1,5-dione]

(6) wherein Y is
  (a) NH, or (b) S;
(7) wherein R$_8$ is
  (a) H, (b) C1-C2 alkyl, (c) OCH$_3$, (d) NO$_2$, (e) NH$_2$, (f) NHCOCH$_3$, (g) CN, (h) CH$_2$NH$_2$, (i) CONH$_2$, (j) Cl, (k) Br, or (l) COOCH$_3$;
(8) wherein R$_9$ is
  (a) H, (b) methyl, (c) benzyl, or (d) —(CH$_2$)$_p$N(R$_{10}$)(R$_{11}$);
(9) wherein R$_{14}$ is
  (a) H, or (b) C1-C6 alkyl;
(10) wherein R$_{15}$ is C1-C6 alkyl;
(11) wherein R$_{16}$ is
  (a) H, or
  (b) C1-C4 alkyl;
(12) wherein X$_7$ and X$_8$ are the same or different and are
  (a) H, (b) CH$_3$, (c) CF$_3$, (d) halogen, (e) OH, (f) OCH$_3$, (g) NO$_2$, (h) NH$_2$, (i) NHR$_4$, NR$_4$R$_4$, (k) —CH$_2$NH$_2$, (l) —CH$_2$NHR$_2$, (m) —SO$_2$N(R$_3$)(R$_4$), (n) —CO$_2$R$_4$, (o) CON(R$_3$)(R$_4$), (p) CH$_2$N(R$_3$)(R$_4$), or (q) tetrazolyl;
III. wherein R$_2$ is
  A. H, B. C1-C4 alkyl, C. benzyl, D. —(CH$_2$)$_p$—N(R$_6$)(R$_7$), E. —(CH$_2$)$_r$—[pyridine with R$_8$]

F. —(CH$_2$)$_r$—[phenyl with X$_7$, X$_8$]—(CH$_2$)$_p$—

G. N(→O)(R$_6$)(R$_7$), H. —(CH$_2$)$_p$N$^+$(CH$_2$—Ph)(R$_6$)(R$_7$), or I. —(CH$_2$)$_p$N$^+$(CH$_3$)(R$_6$)(R$_7$),
J. nothing;
IV. wherein R$_1$ and R$_2$ together are A. ⟨(CH$_2$)$_q$—X$_5$—(CH$_2$)$_q$⟩, or 1. wherein X$_5$ is
  a. O, b. NH, c. NCH$_3$, or d. S;

B. ⟨(CH$_2$)$_2$[—O—(CH$_2$)$_2$]—X$_9$—(CH$_2$)$_2$[—O—(CH$_2$)$_2$]⟩;

2. wherein X$_9$ is a. O, b. NH, or c. NCH$_3$;

V. wherein R$_3$ is

A. H, B. C1-C2 alkyl, or C. CH$_2$OH;

wherein m is 2-8;
wherein n is 0-1;
wherein p is 2-8;
wherein q is 2-4;
wherein r is 1-8;
wherein s is 2-8; and pharmacologically acceptable salts thereof;

with the proviso that when n is 1 and R$_1$ is —(CH$_2$)$_m$—N(R$_6$)(R7) wherein m is 2 or 3 and R$_2$ is H or CH$_3$, or when R$_2$ is —(CH$_2$)$_m$—N(R$_6$)(R7) wherein m is 2 or 3 and R$_1$ is H, CH$_3$, CHO, or CH$_3$CO, then R$_6$ and R$_7$ cannot both be hydrogen, methyl, or ethyl;

and with the proviso that when n is 0 and R$_1$ is —(CH$_2$)$_m$—N(R$_6$)(R7) wherein m is 2 or 3 and R$_2$ is H or CH$_3$, or when R$_2$ is —(CH$_2$)$_m$—N(R$_6$)(R7) wherein m is 2 or 3 and R$_1$ is H, CH$_3$, CHO, or CH$_3$CO, then R$_6$ and R$_7$ cannot both be hydrogen, methyl, or ethyl, propyl, or isopropyl;

and with the proviso that when n is 0 and one of R$_1$ and R$_2$ is —(CH$_2$)$_m$—N(R$_6$)(R7) wherein m is 3, and the other is H or methyl, then R$_6$ and R$_7$ cannot be H or methyl;

and with the proviso that when n is 0 and X1 is NR$_1$, then R$_1$ cannot be CHO when R$_2$ is H;

for each of the foregoing provisos, Z is

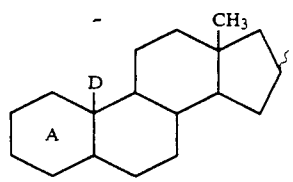

The invention also relates to methods of treatment of phospholipase A2 mediated conditions (PMC), and methods of treatment of diabetes, obesity and atherosclerosis, employing the compounds and methods of the invention.

Compounds of the present invention have been tested in standard laboratory tests to evaluate their ability to inhibit phospholipase A2. In the perfused guinea pig lung, N[3-(dimethylamino)propyl]-N-methyl-3-methoxyestra-2,5(10)-dien-17b-aminehas been shown to be preferred, exhibiting complete inhibition of the enzyme at $4 \times 10^{-7}$ Molar.

Thus, some of the compounds of the present invention are useful whenever it is medically necessary or desirable to inhibit phospholipase A2 in a mammalian system. They are particularly useful in treating symptoms or conditions resulting from the action of the arachidonic acid cascade.

The symptoms or conditions treated or prevented by the phospholipase A2 inhibitory compounds of this invention are those which are produced as a result of the excessive stimulation of the arachidonic acid cascade during certain disease processes or conditions. The multiple enzymes of the cascade act upon 5,8,11,14-eicosatetraenoic acid to produce prostaglandins, leukotrienes, and hydroxylated derivatives. At certain times during these disease processes or conditions, some of these products are responsible for the symptoms or conditions noted above, e.g., inflammation, erythema, allergic responses, and similar conditions. Phospholipase A2 provides the substrate for these enzymes of the cascade by hydrolysis of arachidonate-rich phospholipids. Thus, by the method of this invention is thus effective to treat or prevent the symptoms or conditions, which are designated as PMC's (phospholipase A2 mediated conditions).

The precise mechanisms of the disease processes or conditions which stimulate the arachidonic acid cascade are not clearly understood. The essential prerequisite, however, is enhanced activity of the phospholipases which provide arachidonate to the series of reactions designated as the arachidonic acid cascade. The method of this invention is simply to block the action of the phospholipases and cut off the flow of arachidonate into the cascade, irrespective of the stimulus or stimuli which may be present. This is accomplished with the phospholipase A2 inhibitory compounds of the present invention. Thus, the method of phospholipase A2 inhibition of this invention is suitable for treating seemingly unrelated diseases whose common element is the stimulation of the arachidonic acid cascade. PMC includes all untoward conditions or symptoms which are the result of the excessive stimulation of the arachidonic acid cascade. These conditions encompass allergic diseases, inflammatory conditions (including chronic inflammatory conditions such as rheumatoid arthritis), burns, and hypoxic conditions at the cellular level such as coronary infarcts, or infarcts of other t ˆ F ˆ PBvent the destruction of the phospholipids that are substrates for phospholipases which also are integral structural components of cellular membranes.

The phospholipase A2 inhibition method of this invention is used on any mammal whose metabolic system includes the phospholipase induced arachidonic acid cascade. The mammals which are preferred are generally domesticated animals and humans. Humans are the most preferred mammals to be treated by the method of this invention.

The dosage regimen for preventing or treating PMC by the compounds of this invention is selected in accordance with a variety of factors., including the type, age, weight, sex and medical condition of the mammal, the severity of the PMC and the particular compound employed. An ordinarily skilled physician or veterinarian will readily determine and prescribe the effective amount of the anti-PMC agent to prevent or arrest the progress of the condition. In so proceeding the physician or veterinarian could employ relatively low dosages at first, subsequently increasing the dose until a desired or maximum response is obtained.

Initial dosages of the compounds of this invention can be from about 0.003 to 3.0 g per 70 kg mammal per 6-8 hours orally. When other forms of administration are employed, equivalent doses are administered. When dosages beyond 45 mg/kg are employed, care should be taken with each subsequent dose to monitor possible toxic effects.

The degradation of cell membranes by phospholipase A2, hydrolyzing the phospholipid components of the membrane, is believed to be a component in the cellular death resulting from hypoxic states such as coronary infarcts, ligation of the aorta during surgery for aortic aneurysms (resulting in kidney damage), and the like. Inhibition of phospholipase A2 by these compounds could greatly ameliorate the cellular damage resulting froSee Zalewski, et al., Clinical Research 31, p. 227 (1983). This is a preferred use of these compounds.

Asthma is a disease of the lungs in which a wide variety of stimuli can result in an asthmatic attack. These stimuli range from damp cold air to allergens in the environment. The asthmatic response is characterized by constriction of the bronchioles leading to increased airway resistance. There is an early constructive phase due to histamine release from mast cells, as well as other modulators, e.g., peptides. A late sustained phase then occurs which in human beings may reach a maximum in 6–8 hours. This phase is slower in onset and disappearance, and is due to a complex of products of the arachidonic acid cascade. These products include thromboxanes, prostaglandins, and leukotrienes. The precursor for all of these eicosanoids is arachidonate which is released from esterified forms in membranes to the appropriate enzymes by the action of phospholipase A2. See, e.g., "Corticosteroid Treatment in Allergic Airway Diseases, "Proceedings of a Symposium in Copenhagen Oct. 1-2, 1981 (Editors: T. H. Clark, N. Myginfd, and O. Selroos, Munksgaard/Copenhagen 1982). Thus, a block of phospholipase A2, which is physiologically acceptable, will prevent release of eicosanoids in the lung thought to be responsible for the "2nd wave" of airway resistance. This is a preferred use of some of the compounds of this invention.

Thus, the phospholipase A2 inhibitory compounds are useful in the treatment of asthma. For example, these compounds are useful as bronchodilators or as inhibitors of mediators such as SRS-A which are released from cells activated by an antigen-antibody complex. Further, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, intradermally, or intramuscularly, with intravenous administration being preferred in emergency situations, by inhalation in the form of aerosols or solutions for nebulizers; or by insufflation in the form of powder. These compounds are effectively administered to human asthma patients by oral inhalation or by aerosol inhalation.

Doses in the range of about 0.01 to 50 mg per kg of body weight are used 1 to 4 times a day, the exact dose depending on the age, weight, and condition of the patient and on the frequency and route of administration. For the above use these compounds can be combined advantageously with other anti-asthmatic agents, such as sympathomimetics (isoproterenol, phenylephrine, ephedrine, etc.); xanthine derivatives (theophylline and aminophylline); and corticosteroids (e.g., prednisolone).

For administration by the oral inhalation route with conventional nebulizers or by oxygen aerosolization it is convenient to provide the instant active ingredient in dilute solution, preferably at concentrations of about 1 part of medicament to form about 100 to 200 parts of weight of total solution. Entirely conventional additives may be employed to stabilize these solutions or to provide isotonic media, for example, sodium chloride, sodium citrate, citric acid, sodium bisulfite, and the like can be employed.

A self-propelled dosage unit suitable for inhalation therapy for administering the active ingredient in aerosol form comprises the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispensing agent such as oleyl alcohol. Suitable means to employ the aerosol inhalation therapy technique are described fully in U.S. Pat. No. 2,868,691, for example.

These novel compounds are useful as anti-inflammatory agents in mammals and especially humans, and for this purpose, are administered systemically and preferably orally. For oral administration, a dose range of 0.05 to 50 mg per kg of human body weight is used to give relief from pain associated with inflammatory disorders such as rheumatoid arthritis. They are also administered intravenously in aggravated cases of inflammation, preferably in a dose range 0.01 to 100 g per kg per min until relief from pain is attained. When used for these purposes, these novel compounds cause fewer and lesser undesirable side effects than do the known synthetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions are preferred.

These compounds are useful whenever it is desired to inhibit platelet aggregation, reduce the adhesive character of platelets, and remove or prevent the formation of thrombi in mammals, including man, rabbits, dogs, and rats. For example, these compounds are useful in the prevention of myocardial infarcts, to prevent post-operative thrombosis, to promote patency of vascular grafts following surgery, and to treat conditions such as atherosclerosis, arteriosclerosis, blood clotting defects due to lipemia, and other clinical conditions. For these purposes, these compounds are administered systemically, e.g., intravenously, subcutaneously, intramuscularly, and in the form of sterile implants for prolonged action. For rapid response especially in emergency situations, the intravenous route of administration is preferred. Doses in the range about 0.005 to about 20 mg per kg of body weight per day are used, the exact dose depending on the age, weight, and condition of the patient or animal, and on the frequency and route of administration.

Increased phospholipase activity has been observed after central nervous system (CNS) trauma, e.g., brain and spinal cord injury. See, E. P. Wei, et al., J. Neurosurg., 56, pp. 695-698 (1982) and E. D. Hall and J. M. Braughler, Surgical Neurology, 18, pp. 320–327 (1982). Thus, phospholipase inhibitors, such as the compounds of the present invention, would be useful in the treatment or prevention of such conditions.

The method of this invention is useful both in treating a PMC or symptom which has already manifested itself in the mammal as well as the prevention of these conditions or symptoms in mammals including those particularly susceptible to them. Employment of the method of this invention prior to the development of a PMC would prevent the formation of the prostaglandins and similar products necessary for such conditions. Thus, the method of this invention can be used to prevent edema and erythema from sunburn by administering these compounds prior to exposure to sunlight. The compounds of this invention could be administered to persons suffering from hayfever or similar allergies prior to exposure to the allergenic substances to which hayfever sufferers are sensitive. In a like manner, a physician or veterinarian could readily determine other mammals or persons susceptible to a PMC.

It is most preferred to use the compounds of this invention in the treatment or prevention of asthma and in the treatment or prevention of cellular death resulting from hypoxic states.

The actual inhibition of phospholipase A2 by the method of this invention takes place on a cellular level. Administration of the phospholipase A2 inhibitory compounds of this invention can thus be by any manner that will allow for phospholipase A2 inhibition in the affected tissue or organs. The preferred route in most cases is to systemically administer the compounds, i.e., to allow them to enter the mammal's bloodstream and thus be distributed throughout the mammal's system. In certain cases, where the PMC is of a localized nature (e.g., sunburn or psoriasis), topical administration (e.g., transdermal) may be employed in order that the phospholipase A2 inhibition is confined to the afflicted area.

Since the diseases or conditions resulting from the arachidonic acid cascade are varied, methods of administering these compounds must depend on the particular PMC to be treated. Regardless of the route of administration selected the compounds used in the process of the present invention are formulated into pharmaceutically acceptable dosage forms by conventional methods known to the pharmaceutical art.

Thus, the compounds can be administered orally in forms such as pills, capsules, solutions or suspensions. They may also be administered rectally or vaginally in forms such as suppositories or bougies. They may also be introduced parenterally, e.g., subcutaneously, intravenously, or intramuscularly using sterile injectable forms known to the pharmaceutical art. For treatment of conditions such as erythema the compounds of this invention may also be administered topically in the form of ointments, creams, gels, or the like.

The compounds of the present invention may be formulated into pharmaceutical compositions, employing a pharmaceutically acceptable carrier.

The pharmaceutical forms contemplated by this invention include pharmaceutical compositions suitable for oral, parenteral, vaginal, topical, and rectal use, e.g., tablets, powder packets, cachets, dragees, suppositories, bougies, and the like. Suitable diluents or carriers such as carbohydrates (lactose), proteins, lipids, calcium phosphate, cornstarch, stearic acid, methylcellulose and the like may be used as carriers or for coating purposes. Oil, e.g., coconut oil, sesame oil, safflower oil, cottonseed oil, peanut oil may be used for preparing solutions or suspensions of the active drug. Sweetening, coloring and flavoring agents may be added. By "pharmaceutical excipient" is meant any of these and similar well known forms of drug formulations.

In general the preferred route of administration depends on the condition being treated. For asthma, oral inhalation or aerosol inhalation is preferred. For most other conditions the preferred mode of administration is oral.

Some of the compounds of the present invention are useful as hypoglycemic agents in non-insulin dependent diabetes mellitus (NIDDM) with insulin resistance. NIDDM refers to a condition commonly found in patients suffering from elevated serum glucose levels resulting from an impairment of tissue response to insulin and/or an impairment of pancretic islet function. Failure to adequately control such elevated serum glucose levels (hyperglycemia) has been associated in such patients with untoward cardiovascular effects (myocardioischemia, stroke, and peripheral vascular diseases), lethargy, coma, and even death.

While conventional treatment for these hyperglycemic conditions may include diet (e.g., restriction of carbohydrate intake) and insulin injection, one important means of treating such patients is with oral hypoglycemic agents.

Some of the compounds of this invention have the ability to lower the serum glucose levels in KKA$^y$ mice with spontaneous diabetes, and they are expected to be of value in the treatment of NIDDM and its complications in mammals, including human beings. Accordingly, a patient to be treated with certain of the novel compounds of this invention is first diagnosed as a diabetic by conventional means (e.g., the persistence of elevated serum glucose levels), and a treatment regimen with certain compounds of this invention established so that the elevation in a patient's serum glucose level is either significantly reduced or eliminated. The precise therapeutic endpoint of treatment (i.e., elimination or merely reduction in hyperglycemia) is readily determined by the attending physician based upon the clinical presentation and concomitantly employed treatment. For example, certain of the novel compounds of this invention may be employed to significantly reduce hyperglycemia in a patient, with a carbohydrate-restricted diet providing the further measure of control.

While the novel compounds of this aspect of the invention may be administered by any convenient route) e.g., orally, subcutaneously, intravenously, intramuscularly, topically, or rectally), these compounds are most significantly and usefully employed as oral hypoglycemic agents, particularly in solid dosage form, e.g., capsules and tablets. Alternatively, liquid oral dosage forms (e.g., syrups and elixirs) are alternatively employed. The solid, oral pharmaceutical compositions in accordance with the present invention are all prepared by methods known in the art, e.g., methods for preparing other oral antidiabetic compositions. Since an individual patient response to treatment with compounds in accordance with the present invention may vary, effective dosages of the compounds of the instant invention will vary from patient to patient. Ordinarily, an oral dosage of from 0.1 to 10 mg/kg of a compound in accordance with the instant invention will be adequate to significantly reduce hyperglycemia in a patient being treated. Repeated dosages, e.g., every 4-12 hr, may be required during the day to maintain the antihyperglycemic effect. Accordingly, dosages in accordance with the present invention may range from as low as about 0.1 mg/kg/dose to as high as about 10 mg/kg/dose, depending upon the patient, frequency of treatment, and observed response. In accordance with well-recognized methods, an attending physician may at first prescribe a relatively small amount of the novel compound of this invention, with subsequent increases in this dosage as necessary to achieve the desired level of control.

Some of the compounds of the present invention are also useful to treat and/or prevent obesity in mammals including human beings. For this purpose, the novel compounds of this invention are formulated and administered as described above for hyperglycemia.

DETAILED DESCRIPTION

The definitions which follow apply throughout the specification unless specifically noted otherwise.

All temperatures are in degrees Centigrade.

Halogen refers to chlorine, bromine, fluorine or iodine.

Hal refers to chlorine, bromine, or fluorine,

IR refers to infrared spectroscopy.

NMR refers to nuclear (proton) magnetic resonance spectroscopy, chemical shifts are reported in ppm ($\delta$) downfield from TMS.

TMS refers to tetramethylsilane.

MS refers to mass spectrometry.

Ts refers to p-toluenesulfonyl.

Ms refers to methanesulfonyl.

Brine refers to saturated aqueous sodium chloride.

$R^1$-$R^{16}$ and $X^1$-$X^9$ are as defined in the first occurrence of each herein unless indicated otherwise. For example $R_4$ as used in claim 2 has the same definition as $R_4$ used in claim 1.

The charts are meant to be schematic and the variables used therein are used generically. For example R may be alkyl, $X^-$ may be halogen, etc.

When the term "Cn-Cp alkyl", for example, is used, it means and includes isomers thereof where such exist.

A bond indicated as "—" includes both the $\alpha$ and $\beta$ configurations.

Acyl includes aroyl, phenacyl, substituted phenacyl, $COCH_3$, $COC_2H_5$, and $COC_3H_7$.

Methods For Preparing Compounds of Formula III and Related Compounds

Referring now to Chart A:

The formamide A-2 may be prepared from the Leuckart reaction of formula A-1, e.g., estrone methyl ether with 3-dimethylaminopropylamine in formic acid. To purify the crude reaction product, chromatography (e.g., silica gel, 5% of a 10% $NH_4OHCH_3OH$ solution in $CH_2Cl_2$, see section below on reactions of amino-side chains upon prolonged contact with $CH_2Cl_2$) is helpful.

When the synthesis of formamide A-2 is modified to use, for example, a ratio of estrone methyl ether:amine:-formic acid of 1:5:5, the reaction yields the un-formylated 17-NHR formula A-3.

To obtain the N-methyl group of formula A-4, amide A-2 is reduced with lithium aluminum hydride ($LiAlH_4$) in dioxane according to known procedures. The crude product obtained from this reduction is of high quality and may be used directly for most subsequent transformations, including salt formation and reduction.

Reaction of Dimethylaminopropyl Side Chains with Methylene Chloride Referring now to Chart A:

When solutions of, for example, steroids containing tertiary amines in methylene chloride are allowed to stand at 25° for several days, a much more polar product, the methylene chloride adduct A-7 accumulates. The product is isolated by trituration with 90% ethyl acetate/hexane.

Treatment of the methylene chloride adduct A-7 with excess sodium ethoxide in refluxing ethanol affords the same N-allyl product, A-8, as that obtained, infra, from mild pyrolisis of the N-oxide A-5, as well as the N-demethylated analog.

Quaternary Amine Salts and N-Oxides

Referring now to Chart A:

Reaction of formula A-4 with, for example, excess methyl iodide in methanol gives an insoluble solid compound which has a mono quaternary ammonium iodide structure A-7.

Alkylation of A-4 with benzyl chloride and with ethyl chloroacetate gives quaternary salts. In all of these cases, quaternization occurs at the terminal nitrogen of the side chain in preference to the 17-amino nitrogen.

Synthesis of the mono- and bis-N-oxides of formula A-4, is set forth in Chart A, Step A-4. Compound A-4 is oxidized, for example, with hydrogen peroxide in methanol (A. C. Cope and Ciganek, Org. Synth. Coll., 4, p. 612 (1963)), a reaction which produces selectively either the mono-, A-5, or bis-N-oxide, A-6, depending on the amount of hydrogen peroxide employed and the reaction time.

A-Ring Modifications of Compound A-10

Referring now to Chart A:

For A-ring modifications of the steroidal moiety, Birch reduction of methoxy A-9 gives the more highly saturated compound A-10. To reduce the presence of small amounts of any unreduced starting compound in the product, several recrystallizations from ether-acetonitrile may be employed.

To produce compounds of the present invention with the methoxy substituent removed from the A-ring of the steroidal moiety, for example, 17-ketoestrane is subjected to the Leuckart reaction-$LiAlH_4$ reduction sequence, (Chart A, steps 1 and 2, supra) to produce the formamide and the diamine.

Referring now to Chart D:

Acetate and butyrate derivatives (D-4) of phenol D-2 can also be prepared, and the phenol D-2 also can be brominated with N-bromoacetamide to produce the 4-bromo analog D-5.

We have also prepared a series of analogs in which the diamino side-chain is modified in various ways. This series of compounds has the aromatic A-ring rather than the dihydro aromatic A-ring to avoid the Birch reduction step. The aromatic A-ring analogs further avoid the chemical instability inherent in the enol-ether of the dihydro aromatic compounds.

In preparing the side-chain modifications, two synthetic routes were used. The first of these is the Leuckart reaction of, for example, estrone methyl ether with the desired amine in formic acid as outlined in Chart A, supra.

The second synthetic reaction is the reductive amination of, for example, estrone methyl ether with the desired amine and sodium cyanoborohydride (Chart B), R. F. Borch et al., J. Am. Chem. Soc., 93, p. 2897 (1971). For this series of analogs we used only primary amines in the reaction, consequently the products are the secondary amines represented by formula B-2.

We have also prepared various analogs in which the major changes are in the alteration of the steroidal (or hydrocarbon) nucleus of the molecule. Various groups such as cyclopentadecyl, cyclododecyl, decalyl, adamantyl, bicyclohexyl, and pyrenyl have been used to substitute for the estrogen steroidal skeleton.

We began by selecting various readily available molecules that were comprised primarily of a large hydrocarbon portion and a functional group that could easily be converted into a diamino side-chain. Several macrocyclic ketones are commercially available and provide a convenient point of departure.

Referring now to Chart A:

The first analog of this type was obtained from the Leuckart reaction between cyclopentadecanone and 3-dimethylaminopropylamine in formic acid which gave the formamide (A-2). Also, the secondary amine (A-3) which has not undergone formylation during the reaction may be isolated. During chromatographic purification of the secondary amine on silica gel using ethyl acetate-methanol-triethylamine, the compound is obtained from the column as the acetate salt. Reduction of the formamide A-2 with lithium aluminum hydride gives the N-methyl analog A-4 which is converted to a crystalline disuccinate salt.

We have also prepared a similar analog from cyclododecane using the reductive amination procedure with $NaB(CN)H_3$ (Chart B, Step 1) instead of the Leuckart reaction to attach the diamino side-chain. As in the case of the secondary amine above, this secondary amine also is obtained as a crystalline acetate salt following chromatography.

Several other side-chain modifications have been incorporated with these macrocyclic hydrocarbons. The bisdimethylaminopropyl amine side chain, has been attached to cyclododecane and a tetraamino side chain has been attached to cyclopentadecane.

Bicyclohexyl Hydrocarbon Analogs

The preceding macrocyclic analogs are the least rigid cyclic systems available. Using other available ketones, we have prepared analogs with increasing degrees of structural rigidity. Reductive amination of 2-cyclohexylcyclohexanone and 4-cyclohexylcyclohexanone gives in each case the isomeric cis and trans compounds. The isomers are separated by chromatography.

Three isomeric pairs of analogs, from reaction with 3-dimethylaminopropylamine, 1,4-diaminobutane, and 3-aminomethylpyridine have been prepared from 4-cyclohexylcyclohexanone. Another pair of analogs closely related to the above was obtained from reaction of 4-phenylcyclohexanone with 3-dimethylaminopropylamine.

Rigid Hydrocarbon Analogs trans-1-Decalone and adamantanone are two readily available ketones having rigid hydrocarbon skeletons. Both have been converted to 3-dialkylaminopropylamine derivatives. The former when aminated with 3-diethylaminopropylamine gives a single compound. Reaction of adamantanone with 3-dimethylaminopropylamine gave a product which was converted to the crystalline disuccinate salt.

Other Hydrocarbon Analogs

One of the first modified analogs we prepared used a steroid, 3-cholestanone, as the hydrocarbon nucleus. Leuckart reaction conditions with 3-dimethylaminopropylamine produces a mixture of formamides which were reduced to the methylamines. No separation of isomers could be detected with various chromatographic systems, so the mixture was converted to the solid disuccinate salt.

Pyrene-1-carboxaldehyde was converted to the diamine derivative as an example of a polycyclic aromatic hydrocarbon analog.

Many new nonsteroidal anti-inflammatory agents have been developed in recent years and these frequently contain a bicyclic hydrocarbon nucleus attached to a propionic acid. These are converted to diamines via the acid chlorides and amides. We converted flurbiprofen to the diamine by preparation of the acid chloride followed by reaction with 3-dimethylaminopropylamine to obtain the amide. Lithium aluminum hydride reduction of the amide produced the diamine. Another analog was prepared by similar treatment of the 3-ethyl-4-(p-methoxyphenyl)-2-methyl-3-cyclohexene1 carboxylic acid.

The first analog prepared containing a pyridine ring as a part of the diamino sidechain was obtained from the Leuckart reaction of estrone methyl ether with 3-aminomethylpyridine (Chart A, Step 1). This reaction gives the expected formamide A-2 together with the secondary amine (A-3), supra.

Compounds such as these can also be prepared by reductive amination of estrone methyl ether with the desired amine and sodium cyanoborohydride (Chart B) which is a simpler route to the compounds than the Leuckart reaction. Good yields are observed for compounds produced this way and only in some cases is a chromatography step employed. Analogs having a phenyl or a substituted phenyl ring in place of the pyridine can also be prepared in this way.

When the Leuckart reaction between estrone methyl ether and 2-(2-aminoethyl)-pyridine is attempted, the reaction product is N-formyl-3-methoxyestra-1,3,5(10)-trien17$\beta$-amine rather than the expected formamide. The 2-(2-aminoethyl)pyridine side chain can be attached to estrone methyl ether by reductive amination.

The 3-aminomethylpyridine group can be added to cyclopentadecanone to give an analog and to 4-cyclohexylcyclohexanone to give two isomeric analogs.

Variation in Side Chain Length

A homologous series of $a, \iota$ -diamines was synthesized having a variable number of carbons between the nitrogen atoms. Most of these analogs were prepared via reductive amination (R. F. Borch et al., J. Am. Chem. Soc., 93, p. 2897 (1971) of the ketone of formula I (purchased from Searle) with the appropriate diamines (in most cases, commercially available).

Also synthesized were a series of compounds in which the terminal nitrogen atom of the steroidal diamines is derivatized. Conversion of N-(3-methoxy-1,3,5(10)estratrien-17-yl)-1,6-hexanediamine to a series of derivatives is accomplished in good yields using standard methods.

Reductive amination of the estrone 3-methyl ether with methylamine was done on a reasonably large scale (>10 g) and provided both the 17$\alpha$- and 17$\beta$-isomers in a ratio of 1:12. The 17$\beta$-isomer in particular is a key intermediate en route to certain other diamines, via amide formation using the C-17 amine, followed by $LiAlH_4$ reduction.

Several tri- and tetra-amino steroids were prepared. In each case, the required polyamine fragment was commercially available. This series offered variety both in terms of side chain polarity and metal chelating ability.

The synthesis of analogs with the diamine moiety attached at C-20 of a progesterone side chain was also done. The conversion of estrone 3-methyl ether to 17-deoxo-17-acetyl derivative was accomplished by the proceduce of Bull and Tuinman Tetrahedron, 31, p. 2151 (1975). The C-17 ketone was transformed into the corresponding 17-cyano steroid via condensation with tosylmethyl isocyanate. The nitrile was then treated with methyllithium to afford 17$\beta$-acetyl intermediate along with approximately 20% of the 17$\alpha$-isomer, readily separable chromatographically. Subjection of the 17$\beta$-intermediate to the Leuckart/$LiAlH_4$ sequence led to the recovery of two isomeric diamines. NMR evidence suggested that some loss in stereochemical purity had occurred at C-17, so that four isomers were possible. Reductive amination of the 17$\beta$-intermediate with N,N-1,3-diaminopropane (under much milder conditions) gave only the two expected C-20 epimers. Treatment of the 17$\beta$-intermediate under the standard Mannich conditions afforded a mixture of the desired aminoketone and elimination product.

A variety of other steroid-based analogs were also synthesized. The ornithine ester was prepared via water-soluble-carbodiimide mediated esterification of bis (BOC) ornithine with steroidal 17β-alcohol, followed by deprotection of the amines with trifluoroacetic acid.

Alkylation of the same alcohol with dimethyl trimethylene ammonium salt gave the amino ether. The recovery of the product in the form of its methanesulfonate salt results from the use of sodium bicarbonate rather than sodium hydroxide in the work-up.

N-[3-(Dimethylamino)propyl]-3-methoxyestra-1,3,5(10)-trien-17α-amine was synthesized by displacement of a 17β-mesylate with N,N-dimethyl-1,3-diaminopropane (V. V. Runade et al., J. Med. Chem., 14, p. 38 (1971)). By far the predominant product in this reaction was the $\Delta^{16}$-elimination product.

A steroidal diamine with an 11β-hydroxyl and an unfunctionalized, fully saturated A ring, was made via the standard Leuckart reaction.

Inhibition of Rat Neutrophil Aggregation

1. Method for Thioglycolate Broth Preparation

Weigh sufficient thioglycolate medium, USP grade, to prepare a 5% w/v solution in sterile water. Heat the solution for 10 minutes on a boiling water bath. Remove and allow the solution to cool to 20°-25°. Inject 10±0.5 ml intraperitoneally into Sprague-Dawley rats as described below.

2. Method for Rat Peritoneal Leukocyte Collection

Six (6) Sprague-Dawley, pathogen free, female rats (230-270 grams) are injected intraperitoneally with 10.0±0.5 ml thioglycolate broth, 5% w/v 16-18 hours prior to sacrifice. After sacrifice by cervical dislocation, leukocytes accumulated in the peritoneal cavity are collected by injecting 30 ml of sterile 0.9% w/v sodium chloride intraperitoneally and vigorously massaging the abdomen to assure uniform dispersion of the cells within the carcass. Use a pasteur pipet to remove approximately 20 ml of fluid with suspended cells from a small incision through the abodominal wall. Collect the cell suspension in plastic culture tubes.

3. Washing and Resuspension of Cells for Aggregation

Centrifuge the cell suspensions isolated above for 10 minutes at 1000 rpm (Sorvall RC-3, HG-4L rotor, 25° C.). Discard the supernatant. Resuspend the cells evenly in 0.9% NaCl to original volume, centrifuge a second time for 10 minutes at 1000 rpm. Discard the supernatant. Resuspend the cells evenly in Hanks buffer.

4. Determination of Leukocyte Concentration

Transfer 10 μl of leukocyte suspension into a plastic cell counting cup. Add 15.0 ml of ISOTON~diluent for cell counting. Determine the cell count with a Model ZBI Coulter Counter or equivalent.

5. Neutrophil Aggregation

A. Add 0.5 ml of rat leukocyte (neutrophil) suspension to each channel of a Payton dual channel aggregometer. Cuvettes, 45 mm×4 mm i.d. are used. Cell suspensions at 37° C. are stirred (400 rpm).

B. Add 5 μl test compound (0.01M in absolute ethanol) to cell and evaporate to dryness under nitrogen. Add 0.5 ml cell suspension (37° C., 400 rpm). Incubate for 2 minutes, then add 1 μl of the agonist, $10^{-4}$M FMLP.

C. Record the aggregation trace (% transmitted light) on a potentiometric recorder.

Inhibition of Hog Pancreas PLA$_2$

1. Enzymes

Both soybean lipoxidase and hog pancreas phospholipase A$_2$ are obtained commercially from Sigma. The soybean lipoxidase is dissolved at a concentration of 5 mg/ml in 0.033M ammediol-HCl buffer pH 8.5 with $1 \times 10^{-4}$M Ca$^{++}$. The hog pancreas enzyme is added at the rate of approximately 350 units per ml of final mixture. Thus, 0.025 ml is equivalent to 9 units of phospholipase and 0.125 mg of lipoxidase.

2. Substrate

The substrate is phosphatidyl choline. The material has a fatty acid composition upon saponification, of 2% of 16:0, 1% of 18:0, 3% of 18:1, 18% of 18:2, and 12% of 18:3 fatty acids with the largest fraction being linoleic acid. The estimated molecular weight is 780.

78 mg of this substrate is put in a 10 ml volumetric flask containing 100 mg of deoxycholic acid. A "pill" magnetic stirrer is added along with 7-8 ml of water, and the whole stirred rapidly until all the lecithin is dissolved. The "pill" is then removed and the flask contents are made up of 10 ml with water.

3. Procedure

To three oxygraph cells equipped with magnetic stirrers is added 2.5 ml of 0.033M ammediol-HCl buffer pH 8.5 containing $1 \times 10^{-4}$M Ca$^{++}$. This is followed by 0.1 ml of the inhibitors made up at an initial concentration of 0.01M in methanol. Where controls are run, 0.1 ml of methanol is added to each cell. The cells are then put in the oxygraph apparatus and the contents are stirred briefly. 0.025 ml of the enzyme mixture is then added and the electrodes are inserted in each cell, care being taken to exclude all air bubbles. With the stirrer and water bath pump on, the contents of each cell are stirred for 2.5 minutes at 37.5° C. The reaction is initiated by adding to the cells 0.05 ml of 0.01M lecithin substrate. The reaction is monitored by continuous measurement of rates of oxygen depletion from the medium as a consequence of unsaturated fatty acids (linoleic acid) being released from esterified form by the phospholipase. These fatty acids immediately become substrates for the soybean lipoxidase which forms the 15-hydroxy acids, with consequent oxygen utilization.

The initial rates of oxygen consumption are recorded using a Sargeant-Welch Recorder set at 5 mV full scale. The "air" setting and medium chart speed are used. The slopes of oxygen consumption are then determined in triplicate, and these are compared with the methanol controls to determine the degree of inhibition. If complete inhibition is seen at the first concentration, appropriate dilutions are made to bring the inhibition percentages down to at least 3 concentrations of inhibitor where partial inhibition is observed. The $I_{50}$ can then be calculated for that particular inhibitor, using linear regression slopes. All compounds for which $I_{50}$ value is shown are tested for inhibitory activity on the soybean lipoxidase. None inhibit at the test concentration.

Testing For Blood Glucose Lowering In The KKA$^y$ Mouse

1. General

All KKA$^y$ mice used for screening are produced and selected by methods previously outlined, T. Fujita et al., Diabetes, 32, 804-10 (1983). Groups of 6 animals each are employed.

2. Screening Procedure

Pre-treatment nonfasting blood glucose (NFBG) samples are measured 5 days prior to the start of a screening run by previously described methodologies. These blood sugar values are used to place animals into groups with equal mean blood glucose concentrations and to eliminate any mice with a NFBG value <250 mg/dl. On day 0, compounds chosen to be run are incorporated into ground mouse chow (Purina 5015). Compounds are included at a rate of 1 mg/gram of chow. Generally, 300 g of drugs containing diet is prepared for each group. Mice receiving ground chow only are the negative control. Each screening run also uses ciglitazone (T. Fujita, et al., supra) as a positive control (0.5 to 1.0 mg/gram chow).

Initial body and food weights are taken on day 1. Food is placed in a crock which contains an adequate amount to last for the length of the study. In order to acclimate the mice from pelleted mouse chow to ground mouse chow, they are fed the ground chow for 9 days prior to use in the screen. On day 4 of treatment, a NFBG sample is again measured, as well as food and body weights. Food consumption measurements are used to determine an average mg/kg dose the mice received over the testing period, and to evaluate the compound's effect on food consumption.

3. Acceptance of a Screening Run and Determination of Activity

Acceptance and activity are determined by the following criteria:

A. Negative Control

This group must not show a significant change (p<0.05) from pre-to post-treatment. If there is a significant decrease in blood sugar it means the run is not valid.

B. Positive Control

This group must show a significant depression in blood sugar means levels from pre- to post-treatment. A lack of activity in this group would also invalidate the run.

C. Negative Control vs. Positive Control

This contrast must be significant. It is a further assurance that both control groups performed as expected.

D. Compound

A compound's activity is based on several criteria:

(1) A significant decrease in blood sugar mean levels from pre- to post-treatment. (2) Negative control vs. compound: This contrast allows one to determine if these groups are dissimilar, which is required for the compound to be considered active.

One skilled in the art may determine the specific utility of each compound of the present invention by assaying them by the preceding methods and for angiogenic and angiostatic activity, infra. Compounds that have been found to have a phospholipase $A_2$ inhibitory or antidiabetic effect as determined by at least one of the above assays are indicated in the Examples and Preparations which follow by the notation "PLA2" and/or "diabetes" respectively. If the compound has been tested as inactive in all tests for one of the respective activities, that is indicated by "PLA2-" or "diabetes-" respectively. Some of the compounds were assayed for PLA2 activity by more than one method. If any method showed activity, that compound is listed as having PLA2 activity.

The preferred compounds for phospholipase A2 inhibition include 1-[6-[[(17β)-3-methoxyestra-1,3,5(10)-trien-17-yl]amino]hexyl]-1H-pyrrole-2,5-dione N-[3-(3-aminopropoxy)estra-1,3,5(10)-trien-17-yl]-N,N',N'-trimethyl-1,3-propanediamine and N-[3'-(dimethylamino)propyl]-3-methoxy-N-methylestra-2,5(10)-dien-17β-amine.

The preferred compounds for antidiabetic activity include 3-methoxy-17β-[((3-trifluoromethyl)phenylmethyl)-amino]-estra-1,3,5(10)-triene, N-[3'-(dimethylamino)propyl]-3-methoxy-N-methylestra-2,5(10)-dien-17β-amine and 3-methoxy-17β-[(4-chlorophenylmethyl)amino]-estra-1,3,5(10)-triene.

Preparation 1 N-[3-(Dimethylamino)propyl]-[N]-formyl-3-methoxyestra-1,3,5(10)-trien-17β-amine Formic acid (95-97%, 100 ml) is added dropwise to a cooled and stirred mixture of estrone methyl ether (71.0 g) and 3-dimethylaminopropylamine (158 ml). After completing the addition, the mixture is warmed in an oil bath. At 160°-170° C. bath temperature, considerable gas evolution is observed and care must be taken so that the reaction does not froth out of the flask. When the strongest bubbling subsides, the bath temperature is increased to about 175° C. and heating continued for 18 hours. The reaction mixture is poured onto ice water (500 ml), 50% aq. NaOH (75 ml) is added, mixed well, and stirred with $CH_2Cl_2$ (500 ml). The layers are separated and the aqueous phase is extracted with 250 ml $CH_2Cl_2$. The combined organic extracts are washed with brine, dried ($Na_2SO_4$), filtered, and concentrated to give an oil. A portion of the crude product (44.4 g) is chromatographed on silica gel (2 kg) packed and eluted with 5% of 10% $NH_4OH—CH_3OH$ in $CH_2Cl_2$. Fractions of 375 ml volume are collected and the desired product is eluted in fractions 39-82. These are pooled (25.9 g) and crystallized.

Additional crude product from the above reaction and from a second similar reaction is chromatographed in two portions. From these columns, the title compound is obtained. Each lot is dissolved in hexane (—500 ml) and acetone (50 ml), filtered, and reduced in volume. Cooling gives crystalline title compound in two lots, mp 102°-104° C., and mp 100°-103° C. (Diabetes)

Preparation 2
N-[3-(Dimethylamino)propyl]-3-methoxy-N-methylestra-1,3,5(10)-trien-17β-amine Under a $N_2$ atmosphere, a mixture of lithium aluminum hydride (7.0 g) in dioxane (300 ml) is stirred at 20°-25°. To this is added a solution of the title compound from Preparation 1 (30.5 g) in dioxane over a period of 10 minutes. The resulting mixture is warmed in an oil bath to 100° C. over a period of 90 minutes. In reductions of amides such as this, a sudden evolution of gas in the temperature range of 80°-100° C. is frequently observed with much frothing of the mixture. Care must be taken to allow for this expansion or material may be lost from the reaction vessel. After determining by TLC that the reduction is complete, the reaction is cooled and quenched by the careful addition of aqueous sodium sulfate (75 ml) and water (150 ml). After stirring 45 min., excess solvent is removed under reduced pressure. Methylene chloride (750 ml) and sodium sulfate are added to the residue. The mixture is mixed thoroughly, the methylene chloride is separated, and the solids washed twice more with additional methylene chloride. The combined $CH_2Cl_2$ extracts are concentrated, giving the title compound as an oil. $^1H$ NMR ($CDCl_3$) δ 7.24, 6.72, 6.67, 3.77, 2.82, 2.23, 0.80. (PLA2 and diabetes)

Preparation 3
N-[3-(Diaminomethyl)propyl]-3-methoxy-N-methylestra-1,3,5(10)-trien-17β-amine Disuccinate A solution of succinic acid (6.13 g) in warm methanol (50 ml) is added to a solution of the title compound from Preparation 2 (10.0 g) in methanol (65 ml). The solution is mixed well and left at 20°–25°. Crystals form and are collected giving the title compound, mp 169°–172° C. (Diabetes)

Preparation 4
N-[3'-(Dimethylamino)propyl]-3-methoxy-N-methylestra-2,5(10)-dien-17β-amine Liquid $NH_3$ (1775 ml) is introduced into a three-neck, 5 l flask equipped with an air-driven stirrer, a $N_2$ inlet, and a dry ice/acetone condenser while cooling the flask in an acetone/dry ice bath. The cooling bath is removed, the solution is stirred, and ether (800 ml) is added to the ammonia. Lithium wire (13 g) washed in toluene to remove oil, is cut in pieces and added slowly to the stirred solution. The lithium dissolves quite rapidly and produces a deep blue solution with a bronze-color cast at the glass wall surface. The title compound from Preparation 2 (34.3 g) is dissolved in ether (500 ml) and added via a dropping funnel, inserted between flask and $N_2$ inlet, over a period of 40 minutes. The resulting solution is stirred at the reflux temperature of the ammonia for 30 minutes and then absolute ethanol (170 ml) is added slowly until the solution turns a cloudy white color. Excess ammonia is removed under a stream of $N_2$ by warming the flask on a steam bath. When the residue consists primarily of ether and white solids, it is transferred to a 2 l separatory funnel with the aid of additional ether. Brine-water (1:1) is added cautiously (much heat evolves) until two clear layers are seen. The aqueous layer is separated and the ether layer is washed twice with brine, dried ($MgSO_4$) and degassed with argon. Following drying, the mixture is filtered, the ether filtrate is concentrated, and the crude crystalline residue is recrystallized from ether-acetonitrile giving the title compound, mp 78°–80° C. An NMR spectrum reveals a small amount of starting material to be present in the product. A second recrystallization from ether—$CH_3CN$ gives the title compound, mp 80°–81.5° C., and a third recrystallization (ether—$CH_3CN$) gives the title compound, mp 81°–82° C. (PLA2 and diabetes)

Preparation 5
N-[3'-(Dimethylamino)propyl]-3-methoxy-N-methylestra-2,5(10)-dien-17β-amine Disuccinate Succinic acid (1.23 g) is dissolved in a methanol (18 ml) solution of the title compound from Preparation 4 (2.00 g) by warming on a steam bath. Upon cooling, crystals form and are collected. Recrystallization from methanol-ether gives the title compound as crystals, mp 162°–165° C. (PLA2)

Preparation 6 Ornithine methyl ester dihydrochloride

The procedure of Golankiewicz and Wiewiorowski, Acta Biochimica Polonica, 10, p. 443 (1963), is utilized. A 50 ml round-bottomed, 3-necked flask, equipped with a magnetic stirrer and a gas dispersion tube, is flame dried and then cooled in an atmosphere of nitrogen. The flask is charged with 2 g of ornithine hydrochloride and 25 ml of methanol. The solution is then saturated with hydrogen chloride gas (anhydrous) and concentrated in vacuo (50° C., 1.0 mm, 30 min). The procedure is repeated as before with the exception of a longer time concentrating in vacuo (5 h).

The resulting white hydroscopic solid is kept in a nitrogen atmosphere and yields the title compound; NMR ($CDCl_3$, TMS) δ 4.3–4.1, 3.9, 3.15–2.85 and 2.2 ppm-1.7 ppm.

Preparation 7 3-Methoxy-17(α and β)-cyano-1,3,5(10)-estratriene

The procedure used is taken from J. Bull and A. Tuinman, Tetrahedron, 31, p. 2151 (1975). A flame dried 3000 ml 3-neck round-bottomed flask, equipped with a magnetic stir bar, two constant pressure addition funnels, and a nitrogen inlet tube, is charged with estrone methyl ether (9.0 g) and 800 ml of glyme. Commercially available potassium tert-butoxide (73.0 g, Aldrich) is dissolved in 600 ml of tert-butanol and added rapidly to the starting material. After complete addition, the solution is a clear yellow. Tosylmethyl isocyanide (12.7 g) in 200 ml of glyme is added slowly (2 hours and 20 minutes) to the above solution at 20°–25°. After an additional hour of stirring at 20°–25° TLC indicates the reaction is complete. The reaction is worked up by treating the mixture with water (150 ml), brine (500 ml), and ethyl acetate (2000 ml), and then separating the layers. The organic phase is washed with brine and dried ($MgSO_4$), filtered, and concentrated to provide a solid.

The solid is chromatographed on 1,850 g of 70–230 mesh silica gel eluting with 10% hexane/methylene chloride. An initial fraction of 4000 ml is collected, followed by 50 ml fractions. After fraction 85, pure methylene chloride is used for further elution. By TLC, fractions 83–187 are homogeneous and are combined and concentrated to give a solid (mp 150°–185° C., wide range due to a mixture of the α and β isomers); NMR ($CDCl_3$, TMS) δ 7.33–7.13, 6.83–6.6, 3.77, 3.0–1.1, 0.93 and 0.83.

Preparation 8
17β-Acetyl-3-methoxy-1,3,5(10)-estratriene

A flame dried 3-neck 2000 ml round-bottomed flask, equipped with a magnetic stir bar, nitrogen inlet tube, and 1000 ml constant pressure addition funnel, is charged with the title compound from Preparation 7 (11.6 g) and 600 ml of tetrahydrofuran. Addition of a methyl lithium solution (470 ml of a 1.6M solution as a complex with lithium bromide in diethyl ether, 0.752 mol) is carried out over 20 minutes with slight cooling of the reaction vessel using a cold water bath. The mixture is stirred an additional 1.5 hours at 20°–25° before workup. Analysis by TLC indicates little progress in the reaction over an additional one hour period, and increasing decomposition of products. The reaction is quenched with water (under nitrogen) and extracted with ethyl acetate. The organic phase is washed with 1M hydrochloric acid, saturated sodium bicarbonate, and brine, dried ($MgSO_4$), filtered, and concentrated to give a solid.

The solid is chromatographed on 1300 g of 70–230 mesh silica gel eluting with 20% toluene/methylene chloride. An initial fraction of 4000 ml is collected followed by 40 ml fractions. After the starting material has eluted (fractions 83–112), the eluent is changed to pure methylene chloride. Fractions 148–182 are homogeneous by TLC and correspond to the α-isomer. These fractions are combined and concentrated to provide a solid. The following 900 ml collected contains a mixture of the α and β isomers with only a trace of the α-isomer. Solvent evaporation gives a solid.

The solid from the β-isomer is recrystallized several times from a methylene chloride-diethyl ether mixture to provide a solid, mp 136°-137° C. (PLA2-)

Preparation 9 N,N'-Bis(t-butoxycarbonyl)-ornithine

A 100 ml round-bottomed, 3-necked flask, equipped with a magnetic stirrer is purged with a stream of nitrogen. The flask is then charged with 4.6 g of ornithine hydrochloride dissolved in 40 ml of aqueous acetone (1:1). To this solution is added 14.8 g of t-butyloxycarbonyl-oxyimino-2-phenylacetonitrile (BOC-ON) followed by 12.4 g of triethylamine. The reaction mixture is stirred at 20°-25° for 3 h.

The reaction mixture is concentrated in vacuo. The resulting residue is partitioned between ethyl acetate and water (pH 3/acidified with 2M sodium bisulfate). The organic layer is separated, washed with brine, dried over magnesium sulfate and concentrated in vacuo.

The crude product is chromatographed on 600 g of CC-4 silica gel. The column is packed and eluted with 50% hexane/ethyl acetate (10 ml fractions).

Fractions 60-150 are combined based on their TLC homogeneity and afford the title compound; NMR ($CDCl_3$, TMS) δ 10.5-10.2, 3.3-3.0 and 2.0 ppm-1.0 ppm.

Preparation 10 Dimethyltrimethyleneammonium methanesulfonate

A solution of 3-dimethylamino-1-propanol (10 ml, 8.72 g) in Burdick & Jackson methylene chloride (100 ml) is cooled to −30° C. and treated with triethylamine (14.44 ml) and then slowly over 10 minutes with methanesulfonyl chloride (7.85 ml). The resulting white suspension is stirred for 40 minutes at −25° to −20° C., treated with ice, stirred for 10 min, then partitioned between ethyl acetate (300 ml) and saturated sodium bicarbonate (300 ml). The layers are separated and the aqueous layer is extracted with ethyl acetate (2×500 ml). The combined organics are washed with aqueous saturated sodium bicarbonate (300 ml), dried over magnesium sulfate, filtered and concentrated to an oil, which gradually solidifies while being stored under high vacuum overnight; NMR ($CDCl_3$, TMS) δ 2.60-3.00, 3.43, 4.57.

Preparation 11
N-[3-(Dimethylamino)propyl]-N-methyl-3-hydroxyestra-1,3,5(10)-trien-17β-amine A degassed solution of freshly distilled THF (60 ml) and diphenylphosphine (2.09 ml) is cooled to 0° C. under nitrogen and treated dropwise with n-butyllithium in hexane (7.08 ml). The resulting red solution is stirred for 5 minutes at 0° C. and for 30 minutes at 20°-25° and is then treated at 20°-25° with a solution of the title compound from Preparation 3 (1.58 g) in freshly distilled THF (12 ml+3 ml+3 ml). The resulting red solution is stirred at reflux for 5 hours, cooled to 0° C. and treated with diphenylphosphine (3.14 ml) followed by 1.61M n-butyllithium in hexane (10.62 ml). The red solution is stirred at 0° C. for 5 minutes, at 20°-25° for 25 minutes and at reflux for about 12 hours.

The reaction is cooled to 20°-25°, concentrated in vacuo and chromatographed on "flash chromatography" −3"×10½" of HPLC grade silica gel in 1:15:85 ammonium hydroxide/methanol/methylene chloride while collecting 150 ml fractions. Fractions 5-11 are combined and concentrated to give the title compound, mp 156°-157° C. (PLA2/diabetes)

Preparation 12
4-Cyclohexylcyclohexylidenephosphorohydrazidic Acid, Diethyl Ester To a solution of 4-cyclohexylcyclohexanone (27.04 g) and acetic acid (3 ml) in $CH_2Cl_2$ (400 ml) was added a solution of diethyl phosphorohydrazidate (28.91 g) in $CH_2Cl_2$ (100 ml). The reaction was stirred at room temperature for 27 hours and then was concentrated under reduced pressure. Toluene was added (2×) and removed under reduced pressure in order to aid in the removal of acetic acid by co-distillation. The residual yellow liquid was the product and was used without further purification. TLC Rf=0.52 (20% acetone in $CH_2Cl_2$, silica gel).

Preparation 13
1-(4'-Cyclohexyl)cyclohexylidenenhydrazone-4-(2",2"-dimethyltrimethylene)ketal-1,4-cyclohexanedione In a nitrogen atmosphere, solid sodium hydride (3.6 g) was added in portions over a 15 minute period to a solution of 4-cyclohexylcyclohexylidenephosphorohydrazic acid, diethyl ester (50 g) in ether (500 ml). The mixture was stirred for 40 minutes and then a solution of 1,4-cyclohexanedione, mono-2,2-dimethyltrimethylene ketal (33.66 g, 0.195 mol) in ether (500 ml) was added dropwise over a period of 20 minutes. After stirring at room temperature for 3 hours, TLC indicated that the reaction was incomplete. Another 0.15 mol of sodium hydride was added and after stirring an additional 1.5 hour, the reaction was complete and was carefully quenched with water. The ether layer was separated and the aqueous phase was extracted again with ether. The combined extracts were washed with water, dried ($Na_2SO_4$), filtered, and concentrated. The residue was a white solid which was used in the next Preparation without purification. TLC of the solid showed an Rf=0.38 (40% ethyl acetate in hexane, silica gel).

Preparation 14
11-Cyclohexyl-14,15-diaza-7-thiadispiro(5.1.5.2)pentadecan-4-one (2',2'-Dimethyltrimethylene)ketal The reaction flask was equipped with a balloon as an indicator of a positive $H_2S$ gas pressure. The flask was charged with a suspension of 1(4'-cyclohexyl)cyclohexylidenenhydrazone-4-(2",2"-dimethyltrimethylene)ketal-1,4-cyclohexanedione (0.15 mol) in 1:1 acetone-benzene (200 ml). Hydrogen sulfide gas was added from a lecture bottle so that the balloon attached to the flask was inflated. The suspension was stirred vigorously and $H_2S$ was added periodically in order to keep the balloon inflated. The mixture was stirred at room temperature for 20 hours after which TLC indicated that the starting material had been completely converted to a new, more polar product. The mixture was filtered to remove solids, which were washed thoroughly with 1:1 acetone-benzene. The filtrate was concentrated under reduced pressure giving the title compound as a semi-solid residue which was used without purification. TLC Rf=0.26 (40% ethyl acetate-hexane, silica gel).

Preparation 15
11-Cyclohexyl-14,15-diaza-7-thiadispiro(5.1.5.2)pentadec-14en-4-one (2',2'-Dimethyltrimethylene)ketal Powdered calcium carbonate (102 g) was suspended in hexane (1.5 l), lead tetra-acetate (99.8 g) was added, and the mixture was stirred at 0° C. for 30 minutes. The hydrazine 11-cyclohexyl-14,15-diaza-7-thiadispiro (5.1.5.2) pentadecan-4-one (2',2'-dimethyltrimethylene)-ketal (0.5 mol) in hexane (2.5 l) (not completely soluble so the insoluble solids were added as a suspension) was added over a period of one hour at 0° C. The reaction mixture was stirred and allowed to warm to 20° C. over a two-hour period. A TLC at this time showed the reaction to be complete. Saturated aqueous sodium bicarbonate was added, the mixture was filtered, and the filtrate was washed with saturated $NaHCO_3$ and with water and then dried over $Na_2SO_4$. The dry solution was filtered and concentrated under reduced pressure, giving 45.5 g of solid. This solid was chromatographed over silica gel (1.9 kg, 5% ethyl acetate-hexane and the desired product was eluted after increasing the solvent polarity to 40% ethyl acetate-hexane. A sample was recrystallized twice from pentane, giving white crystals: IR 1586, 1448, 1446, 1439, 1367, 1363, 1290, 1258, 1152, 1136, 1124, 1110, 1058, 1045, 1018, 980, 972, 967, 955, 910, 904 $cm^{-1}$.

Preparation 16
11-Cyclohexyl-7-thiadispiro(5.1.5.2)pentadecan-4-one (2',2'-Dimethyltrimethylene)ketal The dry, solid thiadiazine, 11-cyclohexyl-14,15-diaza-7-thiadispiro (5.1.5.2) pentadec-14-en-4-one (2',2'-dimethyltrimethylene)ketal (10.72 g, 0.0026 mol), was placed in a round bottomed flask under a $N_2$ atmosphere. The solid was heated at 140° C. for 45 minutes. After cooling to room temperature, the solid was recrystallized from ethyl acetate, giving the episulfide 11-cyclohexyl-7-thiadispiro(5.1.5.2)pentadecan-4-one (2',2'-dimethyltrimethylene)ketal, mp 212°–214° C. Recrystallization of the mother liquors followed by chromatography gave olefin 4-(4'-cyclohexylcyclohexylidene)cyclohexane (2'',2''-dimethyltrimethylene)ketal, mp 176°–177° C. IR (nujol) 1442, 1366, 1362, 1354, 1313, 1286, 1280, 1247, 1240, 1233, 1218, 1140, 1129, 1115, 1095, 1054, 1040, 1017, 962, 956, 910, 899, 891, 738 $cm^{-1}$.

Preparation 17
4-(4'-Cyclohexylcyclohexylidene)cyclohexane (2'',2''-Dimethyltrimethylene)ketal Method A. Solid thiadiazine, 11-cyclohexyl-14,15-diaza-7-thiadispiro(5.1.5.2)pentadec-14-en-4-one(2',2'-dimethyltrimethylene)ketal (0.501 g) and triphenylphosphine (0.381 g) were placed in a round bottomed flask under a $N_2$ atmosphere and heated at 100° C. for two hours. The mixture was stirred occasionally with a glass rod. The temperature was increased to 120° C. for an additional two hours. TLC at this time indicated complete reaction. The cooled reaction mixture was chromatographed (one Merck Lobar size B silica gel column, 5% ethyl acetate-hexane, 20 ml fractions) and the title compound was eluted in fractions 8–13. Recrystallization from hexane gave the title compound, mp 176.5°–177° C.

Method B. Raney nickel active catalyst (39 g, Aldrich slurry in water) was added in portions to a solution of episulfide 11-cyclohexyl-7-thiadispiro(5.1.5.2)pentadecan-4-one (2',2'-dimethyltrimethylene)ketal (4.83 g) in 1:3 tetrahydrofuran-ethyl acetate under an argon atmosphere. TLC showed the reaction to be complete within 20 minutes. The reaction mixture was filtered through Celite and the filter cake was washed well with ethyl acetate. The filtrate was concentrated under reduced pressure giving the title compound.

Preparation 18
4-(4'-Cyclohexylcyclohexylidene)cyclohexanone Dimethyl ketal

A catalytic amount of p-toluenesulfonic acid (26 mg) was added to a solution of 4-(4'-cyclohexylcyclohexylidene)cyclohexane(2'',2''-dimethyltrimethylene)-ketal(5.56 g) in 1:1 methylene chloride-methanol (400 ml). TLC after three hours indicated the reaction to be about 50% complete. Additional methanol (200 ml) was added and the reaction checked by TLC after another two hours. About 10% of starting material remained. The reaction was worked up at this time by the addition of more $CH_2Cl_2$ followed by saturated aqueous $NaHCO_3$ solution. The mixture was shaken and the layers were separated. The aqueous layer was extracted two more times with $CH_2Cl_2$, the pooled $CH_2Cl_2$ extracts were washed with brine, dried ($Na_2SO_4$), filtered, and concentrated to a solid. This dimethyl ketal was used without further purification.

Preparation 19
4-(4'-Cyclohexylcyclohexylidene)cyclohexanone

A solution of 4-(4'-cyclohexylcyclohexylidene)cyclohexanone dimethyl ketal (0.016 mol) and 1.0N HCl (100 ml) in tetrahydrofuran (125 ml) was left at room temperature for 2.5 hours at which time TLC indicated hydrolysis to be complete. Water and brine were added to the reaction solution and the mixture was extracted with ether (4×). The pooled ether extracts were washed with brine, dried ($Na_2SO_4$), filtered, and concentrated to give 4.49 g of white solid. This solid was chromatographed (790 g of 40–63 μm silica gel, 4.5 l of 5% ethyl acetate-hexane followed by 10% ethyl acetate-hexane) with 4-(4'-cyclohexylcyclohexylidene)cyclohexanonedimethyl ketal (0.56 g, 10%) eluted first followed by the title compound. Recrystallization of the title compound from hexane gave colorless crystals, mp 81°–81.5° C.

Example 1
N-[3-(Dimethylamino)propyl]-3-methoxyestra-1,3,5(10)-trien-17β-amine Dihydrochloride, and
N-[3-(Chloromethyldimethylammonium)propyl]-3-methoxyestra-1,3,5(10)-trien-17β-amine chloride Formic acid (97–98%, 47.5 ml) is added dropwise to a cooled and stirred mixture of estrone methyl ether (71.0 g) and 3-dimethylaminopropylamine (158 ml). The resulting mixture is heated in an oil bath (165°–175° C.) for 20 hours. The reaction is quenched in ice water (total volume 700 ml) and the resulting alkaline (pH—9) mixture is extracted twice with $CH_2Cl_2$. The combined extracts are washed with dilute aq. NaOH and with brine, dried ($Na_2SO_4$), filtered, and concentrated. Hexane (250 ml) is added to the residue and a white fluffy precipitate is filtered off. The solvent is removed, leaving a residual light brown oil which slowly crystallizes. A portion (20 g) of this material is chromatographed over silica gel (500 g) packed as a slurry in 7.5% of 10% $NH_4OH$—$CH_3OH$ in $CH_2Cl_2$. The column is eluted (300 ml fractions) with the same solvent system. The desired material (about 14 g) is eluted in fractions 13–26 and pooled in $CH_2Cl_2$. As this solution stands at 20°–25°, crystals form. After two days, the crystals (4.803 g), mp 184°–192° C. with rapid heating, are collected by filtration. More crystals form in the filtrate and after 3 days these are collected. The compound can be recrystallized from methanol-acetone in the freezer, giving the second title compound as crystals, mp 184°-186° C. decomposition (dec) with bubbling.

The remaining reaction product is chromatographed over silica gel (1.5 kg) packed as a slurry in 7.5% of 10% NH₄OH—CH₃OH in chloroform. The column is eluted (350 ml fractions) with the same solvent system. Fractions 28-39 are pooled, dissolved in acetone-CHCl₃ and crystallized by adding hexane and cooling. Crystals are collected, mp 160°→>225° C. The filtrate is concentrated to an oil which crystallizes. This is taken up in ether and ethereal HCl is added. A precipitate is collected and recrystallized from methanol-i-propyl alcohol, giving crystals of the first title compound, mp 278°-283° C. dec. (PLA2)

EXAMPLE 2

N-Methyl-N-[3-(dimethylamino)propyl]-3-methoxyestra-1,3,5(10)-trien-17β-amine, methylene chloride adduct A solution of 18 g of the title compound from Preparation 2 is allowed to stand for about 2 days in—300 mL of methylene chloride at 25°. TLC analysis (15/85/2 methanol/methylene chloride/ammonium hydroxide) shows, in addition to the expected starting compound, a new much more polar component which accounts for about one-third of the material. Following removal of the methylene chloride in vacuo, the residue is taken up in 300 mL of ethyl acetate. The mixture is stirred at 20°-25° for 15 min, then diluted with 30 mL of hexane and stirred 10 min longer. The solids are isolated via filtration through a medium-porosity sintered glass funnel and washed with 200 mL more 90/10 ethyl acetate/hexane. After drying for 1 hr at 25°, 0.1 mm, the title compound is obtained having a mp 164°-165° (dec, mp varies with rate of heating). (PLA2, diabetes)

EXAMPLE 3

N-Methyl-N-[3-(methylamino)propyl]-3-methoxyestra-1,3,5(10)-trien-17β-amine and
N-methyl-N-(2-propenyl)-3-methoxyestra-1,3,5(10)-trien-17β-amine A solution of 469 mg of the title compound from Example 2 and 340 mg of sodium ethoxide in 10 mL of ethanol is heated at reflux for 1 h, by which time TLC indicates that no starting material remains. The mixture is filtered through a fine-porosity sintered glass funnel, and the filtrate, with ethanol washes, is concentrated in vacuo. The residue is chromatographed on an 80 g column of silica gel which is previously deactivated with 8 mL of ammonium hydroxide. The column is packed and eluted (8 mL fractions) with 5/95/1 methanol/methylene chloride/ammonium hydroxide.

Fractions 19-21 contain the second title compound which crystallizes upon trituration with methanol. Filtration and drying (0.1 mm, 16 h, 25°) yields the compound, mp 88°-89° C.

Elution of the above chromatogram with 10:90:2 methanol/methylene chloride/ammonium hydroxide (fractions 47-58) affords the first title compound as an oil; IR ñmax (neat) 1600, 1570, 1500, 1460, 1280, 1255, 1240, 1150, 1035, 905 cm⁻¹. (PLA2) (2nd compound, PAA2—)

EXAMPLE 4

N-[3-(Trimethylammonium)propyl]-3-methoxy-N-methylestra-2,5(10)-dien-17β-amine iodide A solution of the amine produced in Preparation 4 (193 mg) in methanol (10 ml) is treated at 20°-25° with methyl iodide (284 mg). The reaction is stirred at 20°-25° for 20 hours. A precipitate forms which is collected by filtration to give the title compound, mp 206° C., dec. (PLA2)

EXAMPLE 5

N-[3-(Dimethylbenzylammonium)propyl]-N-methyl-3-methoxyestra-1,3,5(10)-trien-17β-amine chloride Following the general procedure of Example 2, but starting with benzyl chloride, the title compound is produced, mp 199°-210° C. (PLA2)

EXAMPLE 6

N-[3-(Dimethylcarbethoxymethyl ammonium)propyl]-N-methyl-3-methoxyestra-1,3,5(10)-trien-17β-aminechloride Following the general procedure of Example 2, but starting with ethyl chloroacetate, the title compound is produced, mp 159°-163° C. (PLA2)

EXAMPLE 7

N-[3-(Dimethylamino)propyl]-N-methyl-3-methoxyestra-1,3,5(10)-trien-17β-amine, N-mono-oxide and N,N'-dioxide A solution of 4.7 g of the title compound from Preparation 2, and 5 ml of 30% aqueous hydrogen peroxide in 120 ml of methanol is stirred at 20°-25° for 72 hr. Additional 5 ml portions of hydrogen peroxide are added at 6 hr and 28 hr. After 72 hr, an argon atmosphere is introduced, and a suspension of 100 mg of 10% platinum/carbon in 1.5 ml of ethanol is added in one portion. The stirred mixture is cooled intermittently to moderate the (initially) fairly vigorous evolution of oxygen. The mixture is stirred for 4 hr (oxygen evolution appears complete at about 2 hr) and then filtered through a pad of Celite on a medium porosity sintered glass funnel. The filtrate, including washes with additional methanol, is evaporated to dryness on a rotary evaporator behind a safety shield, and the residue is azeotroped with six 200 ml portions of methylene chloride to remove most of the water.

A 500 mg portion of silica gel is shaken with 50 ml of concentrated aqueous ammonium hydroxide until the silica becomes homogeneous and free-flowing. The ammonia-treated silica is allowed to stand overnight at 25° C. in a stoppered flask and is then slurry-packed into a column with 10/90/1 methanol/methylene chloride-/ammonium hydroxide. The column is eluted with the same solvent (100-150 ml fractions).

The first title compound is obtained from fractions eluting between 1500-2300 ml. Evaporation of these fractions affords an oil, which turns to a solid upon trituration with 75 ml of ether. Filtration and drying (0.1 mm, 25°, 16 hr) yields the first title compound, a solid with mp 78°-82° C. (PLA2, diabetes)

Elution of the above chromatogram with 50:50:2 methanol/chloroform/ammonium hydroxide (10 L) yields the second title compound. After trituration with ether (−100 ml), filtration, and drying (16 hr, 25° C., 0.01 mm), the solid exhibits a mp 94°–96° C. (PLA2, diabetes)

The amount of hydrogen peroxide and the reaction time in this case are chosen intentionally to produce close to a 1:1 mixture of mono- and bis-oxide. At lower hydrogen peroxide concentration and shorter reaction time the mono-oxide compound is the predominant product (−70%), while more reagent and longer reaction time favors bis-oxide formation.

EXAMPLE 8

N-Methyl-N-(2-propenyl)-3-methoxyestra-1,3,5(10)-trien-17β-amine

A 20 mg sample of mono-oxide compound prepared in Example 7 is heated at 110° C. in the absence of solvent for 15 min. The material is then cooled to 20°–25° and chromatographed on a 10 g column of silica gel which is deactivated with 1 ml of concentrated ammonium hydroxide. The column is packed and eluted with 5:95:1 methanol/chloroform/ammonium hydroxide (1 ml fractions). Fractions 15–18 yield the title compound identical by TLC to the material more fully characterized in Example 3. (PLA2-)

EXAMPLE 9

N-[3-(Dimethylamino)propyl]-N-methyl-3-(1-phenyl-5-tetrazolyloxyestra-1,3,5(10)-trien-17β-amine A degassed solution of the title compound from Preparation 11 (0.294 g) in acetonitrile (25 ml) is treated at 20°–25° under nitrogen with 5-chloro-1-phenyl-1H-tetrazole (0.148 g) followed by anhydrous potassium carbonate (0.276 g). The resulting suspension is stirred at reflux for 21 hours, permitted to cool to 20°–25° and concentrated in vacuo to a light brown residue.

The crude product is chromatographed on "flash chromatography" −3"×8.5" of HPLC grade silica gel-in 1% ammonium hydroxide in 3:17 methanol/methylene chloride while collecting—130 ml fractions. Fractions 4–10 are combined and concentrated to give the title compound. Further purification affords a solid, mp 204°–206° C. (PLA2)

EXAMPLE 10

N-[3-(Dimethylamino)propyl]-N-formyl-estra-1,3,5(10)-trien-17β-amine

Following the general procedure of Prepartion 1, but starting with 17-ketoestrane, the title compound is produced, mp 123°–125° C.

EXAMPLE 11

N-[3-(Dimethylamino)propyl]-N-methylestra-1,3,5(10)-trien-17β-amine

Following the general procedure of Preparation 2, but starting with the title compound of Example 10, the title compound is produced. IR 2950, 2870, 2780, 1490, 1455, 1385, 1340, 1255, 1045, 745 cm$^{-1}$. (PLA2)

EXAMPLE 12

N-[3-(Dimethylamino)propyl]-N-methyl-3-acetoxyestra-1,3,5(10)-trien-17β-amine

A solution of the title compound from Preparation 11 (0.218 g) in pyridine (3 ml) is cooled to 0° C. under nitrogen and treated with acetic anhydride (1.2 ml). The resulting solution is stirred at 0° C. and then permitted to warm to 20°–25° with stirring for 66 hours. The reaction mixture is poured into ice-cold saturated sodium bicarbonate (150 ml) and extracted with ethyl acetate (3×120 ml). The combined organics are washed with aqueous saturated sodium bicarbonate, dried over sodium sulfate, filtered and concentrated to an oil.

The crude product is chromatographed on "flash chromatography" −3"×8½" column of HPLC grade silica gel-in 1:10:90-ammonium hydroxide/methanol/methylene chloride while collecting 150 ml fractions.

Fractions 4–6 are combined and concentrated to give a solid, mp 40°–41° C. (PLA2)

EXAMPLE 13

N-[3-(Dimethylamino)propyl]-N-methyl-3-butyroxyestra-1,3,5(10)-trien-17β-amine

Following the general procedure of Example 12, but starting with n-butyric anhydride, the title compound is produced. IR(film) 2930, 2860, 2815, 2765, 1755, 1605, 1495, 1455, 1375, 1345, 1225, 1155, 1075, 1035, 1000, 935, 825 cm$^{-1}$. (PLA2)

Example 14

4-Bromo-N-[3-(dimethylamino)propyl]-N-methyl-3-hydroxyestra-1,3,5(10)-trien-17β-amine A solution of the title compound from Preparation 11 (0.43 g) in absolute ethanol (30 ml) is treated at 20°–25° under nitrogen with N-bromo acetamide (0.24 g). The resulting yellow solution is stirred at 20°–25° under nitrogen overnight and concentrated in vacuo.

The resulting yellow oil is chromatographed on two size B Lobar columns (in tandem) in 5% of a 9:1 methanol/ammonium hydroxide solution in 95% methylene chloride while collecting 18 ml fractions. Fractions 79–87 are combined and concentrated to give the title compound, mp 75°–78° C. (PLA2)

EXAMPLE 15

N-[3-(Dimethylamino)propyl]-N-formyl-5α-androstan-17β-amine

Following the general procedure of Preparation 1, but starting with 5α-androstan-17-one, the title compound is produced, mp 121.5°–122° C. (PLA2)

EXAMPLE 16

N-[3-(Dimethylamino)propyl]-N-methyl-5α-androstan-17β-amine

Following the general procedure of Preparation 2, but starting with the title compound of Example 15, the title compound is obtained. NMR(CDCl$_3$, TMS) δ 2.26, 0.80. (PLA2)

EXAMPLE 17

N-Formyl-N-(3-methylbutyl)-3-methoxyestra-1,3,5(10)-triene-17β-amine

Following the general procedure of Preparation 1, but starting with isoamylamine, the title compound is produced, mp 106°–107° C. (PLA2-, diabetes)

EXAMPLE 18

N-Methyl-N-(3-methylbutyl)-3-methoxyestra-1,3,5(10)-triene-17β-amine

Following the general procedure of Preparation 2, but starting with the title compound of Example 16, the title compound is produced, mp 80°–80.5° C. (PLA2-, diabetes)

EXAMPLE 19

N-Formyl-N-(3-hydroxypropyl)-3-methoxyestra-1,3,5(10)-triene-17β-amine

Following the general procedure of Preparation 1, but starting with 3-amino-1-propanol, the title compound is produced, mp 159°-161° C. (PLA2-, diabetes-)

EXAMPLE 20

N-(3-Hydroxypropyl)-N-methyl-3-methoxyestra-1,3,5(10)-triene-17β-amine

Following the general procedure of Preparation 2, but starting with the title compound from Example 19, the title compound is produced, mp 121.5°-123.5° C. (PLA2)

EXAMPLE 21

N-(3-Ethoxypropyl)-N-formyl-3-methoxyestra-1,3,5(10)-triene-17β-amine and N-(3-Ethoxypropyl)-3-methoxyestra-1,3,5(10)-triene-17β-amine Following the general procedure of Preparation 1, but starting with 3-ethoxypropylamine, the title compounds are produced. First title compound, mp 107.5°-108.5° C. (PLA2, diabetes-)

Second title compound: mp 64°-64.5° C. (PLA2, diabetes)

EXAMPLE 22

N-(3-Ethoxypropyl)-N-methyl-3-methoxyestra-1,3,5(10)-triene-17β-amine

Following the general procedure of Preparation 2, but starting with the first title compound from Example 21, the title compound is obtained. IR (liquid film) 2970, 2934, 2866, 2853, 2780, 1611, 1501, 1466, 1454, 1444, 1378, 1314, 1282, 1256, 1238, 1176, 1152, 1151, 1123, 1054, 1039 cm$^{-1}$. (PLA2, diabetes)

EXAMPLE 23

N-Formyl-N-[2-(2-hydroxyethoxy)ethyl]-3-methoxyestra-1,3,5(10)-triene-17β-amine

Following the general procedure of Preparation 1, but starting with 2-(2-aminoethoxy)ethanol, the title compound is produced, mp 134°-135° C. (PLA2)

EXAMPLE 24

N-[2-(2-Hydroxyethoxy)ethyl]-N-methyl-3-methoxyestra-1,3,5(10)-triene-17β-amine

Following the general procedure of Preparation 2, but starting with the title compound of Example 23, the title compound is produced, mp 101.5°-102° C. (PLA2, diabetes)

EXAMPLE 25

N-[2-(Dimethylamino)ethyl]-N-formyl-3-methoxyestra-1,3,5(10)-triene-17β-amine

Following the general procedure of Preparation 1, but starting with unsymdimethyl-aminoethylenediamine, the title compound is produced, mp 98°-100° C. (PLA2, diabetes)

EXAMPLE 26

N-[2-(Dimethylamino)ethyl]-N-methyl-3-methoxyestra-1,3,5(10)-triene-17β-amine Disuccinate Salt Following the general procedure of Preparation 2, but starting with the title compound of Example 25, an oil is produced.

A portion of the oil (0.732 g) and succinic acid (0.469 g) are dissolved in methanol (10 ml). Crystals form and are collected after two hours, giving a crystalline solid. Recrystallization from methanol gives the title compound, mp 162°-164° C. (PLA2, diabetes)

EXAMPLE 27

N-[2-(Dimethylamino)ethyl]-3-methoxy-N-methylestra-2,5(10)-dien-17β-amine Disuccinate Salt Following the general procedure of Preparation 4, but starting with the title compound from Example 25, an oil is produced.

The oil (1.946 g) is dissolved in methanol (25 ml) and the solution combined with a solution of succinic acid (1.228 g) in methanol (25 ml). A finely divided, white precipitate forms and after cooling in the refrigerator, filtration of the mixture gives the title compound as crystals, mp 147°-153° C. with slight yellowing. (PLA2, diabetes)

EXAMPLE 28

N-[4-(Dimethylamino)butyl]-3-methoxyestra-1,3,5(10)-trien-17β-amine dihydrochloride Following the general procedure of Example 33, but starting with 4-dimethylaminobutylamine, an oil is produced.

The oil is redissolved in ether and ethereal HCl is added. The solvent is removed under a stream of nitrogen, leaving a white solid. Crystallization from cold methanol gives a first crop, mp 280°-283° C. dec, and a second crop of crystals. Recrystallization from methanol gives the title compound, mp 284°-286° C. dec. (PLA2, diabetes)

EXAMPLE 29

(1'R or S)-N-(4'-Diethylamino-1-methyl)butyl-3-methoxyestra-1,3,5(10)-trien-17β-amine Following the general procedure of Example 33, but starting with 2-amino-5-diethylaminopentane, the title compound is produced. IR 2965, 2932, 2868, 2843, 2804, 1611, 1501, 1466, 1453, 1447, 1381, 1372, 1355, 1336, 1314, 1304, 1282, 1256, 1237, 1202, 1152, 1133, 1101, 1070, 1053, 1042 cm$^{-1}$. (PLA2)

EXAMPLE 30

17β-[1-(4-Methyl)piperazinyl]-3-methoxyestra-1,3,5(10)-triene

Following the general procedure of Preparation 1, but starting with N-methylpiperazine, the title compound is produced, mp 154.4°-155.5° C. (PLA2, diabetes)

EXAMPLE 31

17β-[1-(4-Methyl)piperazinyl]-3-methoxyestra-2,5(10)-diene

Following the general procedure of Preparation 4, but starting with the title compound from Example 30, the title compound is produced, mp 149°–151° C. (PLA2)

EXAMPLE 32

N-[2-(N'-Morpholino)ethyl]-3-methoxyestra-1,3,5(10)-trien-17β-amine dihydrochloride Following the general procedure of Example 33, but starting with 2-(N-morpholino)ethylamine, a gummy, semi-solid precipitate is formed. When this mixture is acidified (pH—6–7) with aqueous HCl, a white solid precipitates. The solid is collected and air dried overnight giving product. Recrystallization from methanol-ether gives colorless crystals, mp dec from 235°–280° C. A sample is recrystallized from methanol-ether, giving the title compound as colorless crystals; mp, dec from 250°–295° C. (PLA2, diabetes)

EXAMPLE 33

N-[3-(N'-Morpholino)propyl]-3-methoxyestra-1,3,5(10)-trien-17β-amine 3-(N'-Morpholino)propylamine(24.0 g), glacial acetic acid (20 g), estrone methyl ether (9.5 g), NaB(CN)H$_3$ (2.09 g), and tetrahydrofuran (80 ml) are added sequentially to methanol (110 ml). The resulting mixture is stirred at 20°–25° for about 2 days, after which a clear solution is seen. TLC (10% of a 1:9 NH$_4$OH—CH$_3$OH solution in CHCl$_3$; 40% ethyl acetate in hexane) reveals that starting steroid is consumed and a major, new more polar material forms. Excess solvent is removed under reduced pressure. Water (300 ml) is added to the residue. After 15 minutes, this solution is washed with ether and then made alkaline by the addition of 50% aqueous NaOH. A cloudy mixture results and is extracted with ether (100 ml). A second extraction with ether (150 ml) is done and, while in progress, crystals form in the first extract. The first extract is cooled on ice and after several hours, the crystals are collected, mp 112°–114° C. The filtrate and the second extraction solution are combined, dried (MgSO$_4$), filtered, and reduced in volume to 50 ml from which a second crop of crystals is collected, mp 110°–114° C. A sample of the first crop is recrystallized from ether, giving the title compound, mp 114°–116° C. (PLA2, diabetes)

EXAMPLE 34

N-[2-(2'-Morpholinoethyl)aminoethyl]-3-methoxyestra-1,3,5(10)-trien-17β-amine trihydrochloride Following the general procedure of Example 33, but starting with N-morpholinoethylenediamine, an oil is produced. The oil is redissolved in ether and etheral HCl is added. The solvent is blown off with a stream of nitrogen, leaving a solid. The solid is recrystallized from water-acetone, giving a white solid. A sample is recrystallized from water-acetone giving the title compound, mp 225°–240° C. dec. (PLA2, diabetes)

EXAMPLE 35

3-Methoxy-N-[3-(pyrrolidin-2-on-1-yl)propyl]estra-1,3,5(10)-trien-17β-amine acetate Following the general procedure of Example 33, but starting with 1-(3-aminopropyl)-2-pyrrolidinone, an oil is produced. The oil is dissolved in chloroform (100 ml). Acetic acid (2.5 ml) is added and the solution is diluted with ether (400 ml) and crystallization allowed to proceed. After cooling on ice, colorless crystals are collected. Recrystallization from chloroform-ether gives the title compound as colorless crystals, mp 113°–123° C. (PLA2, diabetes)

EXAMPLE 36

N-[3-(Imidazoyl)propyl]-3-methoxyestra-1,3,5(10)-trien-17β-aminacetate

Following the general procedure of Example 35, but starting with N-(3-aminopropyl)imidazole, the title compound is produced, mp 82°–86° C. (PLA2, diabetes)

EXAMPLE 37

3-Methoxy-N-[2-(1-methylpyrrol-2-yl)ethyl]estra-1,3,5(10)-trien-17β-amine

Following the general procedure of Example 33, but starting with 2-(2-aminoethyl)-1-methylpyrrole, the title compound is produced, mp 141°–143° C. (PLA2, diabetes)

EXAMPLE 38

N-(2-Furfuryl)-3-methoxyestra-1,3,5(10)-trien-17β-amine

Following the general procedure of Example 33, but starting with furfurylamine, the title compound is produced; mp 60°–62° C. (PLA2-, diabetes)

EXAMPLE 39

N-Cyclopentadecyl-N-(3-dimethylaminopropyl)-N-formylamine and
N-cyclopentadecyl-N-(3-diemthylaminopropyl)amine, acetic acid salt Following the general procedure of Preparation 1, but starting with cyclopentadecanone, the title compounds are produced. The first title compound is rechromatographed on 395 g of 40–63 μm silica gel with 5% triethylamine-ethyl acetate. The product is obtained in fractions 71–110 as an oil. IR (liquid film) 2928, 2858, 2815, 2780, 2765, 2724, 1674, 1459, 1421, 1407, 1261, 1212 cm$^{-1}$. (PLA2)

The N-cyclopentadecyl-N-[3-dimethylamino)propyl]amine is rechromatographed on 395 g of 40–63 μm silica gel using ethyl acetate-methanol-triethylamine (85/10/5) for elution. The product is obtained in fraction 47–90 as an oil which crystallizes. This is then recrystallized from hexane to give the second title compound, mp 88°–90° C. (PLA2, diabetes)

EXAMPLE 40

N-Cyclopentyldecyl-N-[3-(dimethylamino)propyl]-N-methylamine

Following the general procedure of Preparation 2, but starting with the first title compound of Example 39, the title compound is produced. IR (liquid film) 2928, 2857, 2812, 2782, 1459, 1266, 1253, 1211, 1153, 1123, 1097, 1076, 1062, 1043, 1033, 836, 710 cm$^{-1}$. (PLA2, diabetes-)

EXAMPLE 41

N-Cyclopentyldecyl-N-(3-dimethylaminopropyl)-N-methylamine, disuccinate salt

The diamine of Example 40 (274 mg) in methanol (3 ml) is treated with succinic acid (283 mg) in methanol (3 ml). The reaction is stirred at 20°–25° for 18 hours. A white precipitate forms which is collected by filtration. This is then recrystallized from methanol-diethyl ether to give a solid, mp 164°–165° C. (PLA2)

EXAMPLE 42

N-[3-Dimethylammoniumpropyl]-cyclododecamine acetate

Following the general procedure of Example 33, but starting with cyclododecanone, a pale yellow oil (semi-solid) is produced. This oil is partitioned between chloroform (300 ml) and water (600 ml) and adjusted to pH 12 with 2M potassium hydroxide. The layers are separated, and the aqueous layer is extracted with chloroform (300 ml). The organics are washed with 1M potassium hydroxide (200 ml, with gentle shaking) and 1:1 brine-water (250 ml), dried over sodium sulfate, filtered and concentrated to a light yellow oil which becomes semi-solid upon storage under high vacuum overnight.

The crude product is chromatographed on silica gel (1 kg) in 5% triethylamine in 5:1 ethyl acetate/95% ethanol while collecting 40 ml fractions. Fractions 247–364 are combined and concentrated to give a solid which is recrystallized from hot ethyl acetate-hexane to produce the title compound, mp 102°–6° C. (PLA2)

EXAMPLE 43

N,N-bis[3-(dimethylamino)propyl]-cyclododecamine

Following the general procedure of Example 33, but starting with N,N,N',N'-tetramethyl dipropylenetriamine and cyclododecanone, the title compound is produced. IR (mull) 2938, 2906, 2861, 2851, 2812, 2781, 2762, 2724, 1469, 1460, 1445, 1266, 1249, 1043 cm$^{-1}$. (PLA2)

EXAMPLE 44

N-[N',N'-Di-(2-aminoethyl)-2-aminoethyl]-N-cyclopentadecylamine

Following the general procedure of Example 33, but starting with tris-(2-aminoethyl)amine and cyclopentadecanone, the title compound is produced; IR (liquid film) 3361, 3287, 2928, 2857, 2810, 1460, 1350, 1282, 1116, 1043, 893, 843, 711. (PLA2)

EXAMPLE 45 cis- and trans-2-Cyclohexyl-N-[3-(dimethylamino)propyl]-1-aminocyclohexane

Following the general procedure of Example 33, but starting with 3-dimethylaminopropylamine and 2-cyclohexyl cyclohexanone, the title compounds are produced. Cis: IR (liquid film) 3313, 2922, 2853, 2814, 2785, 2764, 1458, 1448, 1376, 1268, 1174, 1169, 1162, 1152, 1110, 1098, 1073, 1043, 892, 859, 847, 722, 687; trans: IR (liquid film) 3314, 2967, 2924, 1575, 1461, 1448, 1373, 1295, 1265, 1169, 1152, 1135, 1120, 1073, 1043, 1033, 893, 851. (PLA2)

EXAMPLE 46 cis- and trans-4-Cyclohexyl-N-[3-(dimethylamino)propyl]-1-aminocyclohexane

Following the general procedure of Example 45, but starting with 4-cyclohexylcyclohexanone, the title compounds are produced. Cis: IR (liquid film) 3293, 2924, 2852, 2813, 2786, 2764, 1459, 1449, 1377, 1359, 1267, 1171, 1042, 739 (PLA2); trans: IR (mull) 2818, 2787, 2763, 2695, 2418, 2350, 2317, 2292, 1647, 1573, 1543, 1404, 1323, 1262, 1042, 914, 651. (PLA2)

EXAMPLE 47 cis- and trans-N-(4-Aminobutyl)-4-cyclohexyl-1-aminocylohexane

Following the general procedure of Example 46, but starting with 1,4-diaminobutane, the title compounds are produced; cis: IR (liquid film) 3580, 3292, 2922, 2851, 2807, 1576, 1472, 1449, 1379, 1359, 1331, 1319, 1109, 889, 849, 820, 739 (PLA2); trans: IR (mull) 3660, 3421, 3373, 3275, 3256, 3169, 3107, 1587, 1480, 1449, 1425, 1366, 1350, 1339, 1315, 1134, 1127, 1119, 933, 915, 897, 889, 859, 847, 826, 802, 788, 780, 741, 695. (PLA2) (trans, diabetes)

EXAMPLE 48 cis-andtrans-N-[3-(Dimethylamino)propyl]-4-phenyl-1-aminocyclohexane

Following the general procedure of Example 46, but starting with 3-dimethylaminopropylamine and 4-phenylcyclohexanone, the title compounds are produced; cis: IR (liquid film) 3294, 3161, 3081, 3061, 3026, 2967, 2932, 2856, 2814, 2784, 2765, 2729, 1601, 1493, 1465, 1461, 1450, 1375, 1358, 1267, 1262, 1179, 1170, 1157, 1129, 1098, 1070, 1042, 1031, 1006, 997, 843, 755, 689 (PLA2); trans: IR (mull) 3380, 3265, 3082, 3067, 3028, 2819, 2802, 2777, 1682, 1603, 1495, 1445, 1308, 1258, 1175, 1117, 1105, 1031, 913, 892, 883, 755, 698, 659, 647. (PLA2) (trans, diabetes)

EXAMPLE 49 trans-1-(3-Diethylaminopropyl)aminodecalin

Following the general procedure of Example 46, but starting with diethylaminopropylamine and trans-1-decalone, the title compound is produced. IR (liquid film) 3307, 2968, 2920, 2853, 2799, 1455, 1447, 1383, 1369, 1201, 1164, 1159, 1128, 1105, 1085, 1070. (PLA2, diabetes-)

EXAMPLE 50 trans-1-(3-Diethylaminopropyl)aminodecalin-dihydrochloride salt

The title compound from Example 49 (100 mg) is dissolved in ether and treated with an ether solution saturated with HCl gas. A white gummy substance precipitates. The solvent is removed and the substance crystallizes after a very thourough drying over P$_2$O$_5$ in a vacuum dessicator. MP 156°–158.5° C. (PLA2)

EXAMPLE 51

2-[N-(3-Dimethylaminopropyl)]adamantanamine

Following the general procedure of Example 33, but starting with 3-dimethylaminopropylamine and 2-adamantanone, the title compound is produced. TLC (ethyl acetate/methanol/triethylamine; 85:10:5) Rf=0.22; NMR (CDCl$_3$) δ 2.62, 2.32, 2.20, 2.10–1.20.

EXAMPLE 52

2-[N-(3-dimethylaminopropyl)]adamantanamine, disuccinate salt

Succinic acid (1.18 g) is dissolved in methanol (10 ml). A solution of the title compound from Example 51 (944 mg) in methanol (5 ml) is added to the succinic acid solution in one portion. The solution is stirred at 20°–25° for 45 minutes. The methanol is partially removed at a reduced pressure and acetonitrile (50 ml) and ether is added. The solution becomes cloudy and a white precipitate forms. The white solid is collected by filtration and dried in a vacuum dessicator over P₂O₅ to give the title compound. The product is recrystallized twice from acetonitrile and has a mp 102°-104° C. (PLA2, diabetes-)

EXAMPLE 53

N-(3-Dimethylaminopropyl)-N-methyl-5α-cholestan-3(-amine,disuccinate salt

Following the general procedure of Preparation 1, but starting with 5α-cholestan-3-one, an oil is produced. This formamide product is a mixture of 3α and 3β isomers by NMR evidence. The isomers do not separate by column chromatography. NMR (CDCl₃) δ 8.20, 8.12, 2.22, 0.99–0.81, 0.67.

The product (1.32 g) described above is reduced with lithium aluminum hydride (0.99 g) as described in Preparation 2. The product is chromatographed on two Merck Lobar TM size B columns. The sample is applied in CH₂Cl₂ and eluted with NH₄OH/MeOH/CH₂Cl₂ (95/4.5/0.5). Fractions with a volume of 20 ml each are collected and the product is obtained in fraction numbers 90–128 to give 0.597 g.

The product described above (597 mg) is dissolved in methanol (6) and a solution of succinic acid (472 mg, 4 mmol) in warm methanol (5 ml) is added. After two or three minutes a white precipitate forms. Stirring is continued for 72 hours. The precipitate is collected by filtration and washed with methanol. The product is dried in a vacuum dessicator at 20°-25° over P₂O₅. The title compound is thus obtained which is recrystallized from methanol and has a mp 180.5°-182° C. (PLA2)

EXAMPLE 54

[3-(Dimethylamino)propyl]-1-aminomethylpyrene

Following the general procedure of Example 33, but starting with 3-dimethylaminopropylamine and 1-pyrenecarboxaldehyde, the title compound is produced. IR (liquid film) 3296, 3040, 2967, 2940, 2857, 2814, 2779, 2765, 1603, 1588, 1459, 1182, 1096, 846, 842, 828, 819, 756, 710, 681. (PLA2)

EXAMPLE 55

(1,1'-Biphenyl)-4-acetamide,N-(3-dimethylaminopropyl)-2-fluoro-α-methyl

Using flurbiprofen (15.71 g), thionyl chloride (50 ml) and then in the second step 3-dimethylaminopropylamine (30 ml) as described previously, the amide is prepared. The product is recrystallized twice from hexane to give the title compound, mp 71.5°-72.5° C. (PLA2)

EXAMPLE 56

3-Cyclohexene-1-carboxamide,N-(3-dimethylaminopropyl)-3-ethyl-4-(4-methoxyphenyl)-2-methyl 3-Ethyl-4-(p-methoxyphenyl)-2-methyl-3-cyclohexene-1-carboxylic acid (8.23 g) is mixed with thionyl chloride (25 ml). The mixture is heated at reflux temperature for 45 minutes and then cooled to 20°-25°. The excess thionyl chloride is removed under reduced pressure. Toluene is added to the residue and evaporated at reduced pressure to aid in the thionyl chloride removal.

A solution of 3-dimethylaminopropylamine (12.18 g) in toluene (25 ml) is treated with a solution of acid chloride (prepared above) in toluene (50 ml). The reaction is stirred for 16 hrs at 20°-25°.

The reaction mixture is diluted with ethyl acetate and poured into water. The pH is adjusted to—10. The layers are separated. The organic layer is washed with half-saturated brine (2×), dried (anhydrous N₂SO₄), filtered and evaporated. The residue is chromatographed on 63–200 μm silica gel which is slurry packed with triethylamine/methanol/ethyl acetate (5/10/85). Eluting with the same solvent, fractions which contain 350 ml each are collected. The crystalline product is collected in fractions 10–16. The product is recrystallized twice from hexane to give the title compound, mp 91°-92° C. (PLA2)

EXAMPLE 57

N-Formyl-3-methoxy-N-(3'-pyridinyl)methylestra-1,3,5(10)-trien-17β-amine and 3-Methoxy-N-(3'-pyridinyl)methylestra-1,3,5(10)-trien-17β-amine Following the general procedure of Preparation 1, but starting with 3-aminomethylpyridine, the title compounds are produced, the first title compound as colorless crystals. IR (mull) 1665, 1629, 1609, 1590, 1575, 1495, 1255, 1151, 1041, 713 cm⁻¹. (PLA2-, diabetes)

The major portion of the fractions contains mixtures of the two products and is rechromatographed over silica gel (750 g) packed in ethyl acetate. Fractions of 300 ml are collected. Fractions 34–42 contain the less polar first title compound and are pooled and crystallized from acetone-hexane. Fractions 43–47 (mixtures) are pooled. Fractions 48–57 (mixtures) are pooled and crystallization attempted from acetone-hexane. Fractions 58–63 (containing traces of less polar component) are pooled and recrystallized from acetone-hexane, giving the second title compound. Fractions 64–76 are pooled and recrystallized from acetone-hexane, also giving the second title compound, mp 125°-127° C. Additional second title compound is obtained by physically separating crystals from the mixtures of the two products. This material has a mp 126°-128° C. A sample is recrystallized again from acetone-hexane and gives the second title compound as crystals, mp 127°-129° C. (PLA2-, diabetes)

EXAMPLE 58

3-Methoxy-N-(3'-pyridinylmethyl)estra-1,3,5(10)-trien-17β-amine

Following the general procedure of Example 33, but starting with 3-aminomethylpyridine, the title compound is produced (PLA2-, diabetes)

EXAMPLE 59

3-Methoxy-N-(2'-pyridinylmethyl)estra-1,3,5(10)-trien-17β-amine hydrochloride

Following the procedure of Example 33, but starting with 2-(aminomethyl)pyridine, an oil is produced. The oil is redissolved in ether and ethereal HCl is added. The solvent is blown off with a stream of N₂ leaving a solid. The solid is crystallized from water (200 ml). Recrystallization from hot water (300 ml) gives the title compound, mp 125°-128° C. (PLA2, diabetes)

EXAMPLE 60

3-Methoxy-N-(4'-pyridinylmethyl)estra-1,3,5(10)-trien-17β-amine

Following the general procedure of Example 33, but starting with 4-aminomethylpyridine, the title compound is produced, mp 157°-159° C. (PLA2-, diabetes)

EXAMPLE 61

N-Benzyl-3-methoxyestra-1,3,5(10)-trien-17β-amine

Following the general procedure of Example 33, but starting with benzylamine, the title compound is produced, mp 102°-104° C. (PLA2-, diabetes)

EXAMPLE 62

N-Formyl-3-methoxyestra-1,3,5(10)-trien-17β-amine

A mixture of estrone methyl ether (14.2 g) and 2-(2-aminoethyl)-pyridine(24 ml, 24.4 g) is stirred and cooled in an ice bath. To this mixture, formic acid (97-98%, 11.5 ml) is added in portions. The mixture is then heated in an oil bath (180°-190° C. bath temp.) for 24 hours. The mixture is poured onto ice, treated with NaOH, and extracted with methylene chloride (3×). The extracts are dried ($Na_2SO_4$), filtered, and concentrated to give a solid. The solid is crystallized from methylene chloride-hexane to give crystals. Recrystallization from methylene chloride-acetone gives the title compound, mp 252°-253° C. preceded by yellowing. (PLA2-, diabetes)

EXAMPLE 63

3-Methoxy-N-[2-(2'-pyridinyl)ethyl]estra-1,3,5(10)-trien-17β-amine

Following the general procedure of Example 33, but starting with 2-(2-aminoethyl)pyridine, the title compound is produced; mp 130°-132° C. (PLA2-, diabetes)

EXAMPLE 64

3-Methoxy-N-[{2-[N'-(5-nitro-2-pyridinyl)-amino]ethyl]}estra-1,3,5(10)trien-17β-amine Following the general procedure of Example 33, but starting with 2-(2-aminoethylamino)-5-nitropyridine, the title compound is produced, mp 107°-109° C. (PLA2-, diabetes)

EXAMPLE 65

N-Cyclopentadecyl-N-(3-pyridylmethyl)amine

Following the general procedure of Example 33, but starting with 3-aminomethylpyridine and cyclopentadecanone, the title compound is produced, NMR ($CDCl_3$, TMS) δ 8.58, 7.72, 7.25, 3.76, 2.56, 1.32.

EXAMPLE 66

N-Cyclopentadecyl-N-(3-pyridylmethyl)amine, succinate salt

Succinic acid (885 mg) is dissolved in methanol (10 ml). A solution of the title compound from Example 65 (950 mg) in methanol (5 ml) is added to the succinic acid solution in one portion. The solution is stirred at 20°-25° for 45 minutes and then the methanol is partially removed by evaporation at a reduced pressure. Next, ether is added to the partially evaporated solution and a white precipitate forms. The solid is collected by filtration. The solid is recrystallized from acetonitrile twice to yield the title compound, mp 148°-149° C. (PLA2, diabetes-)

EXAMPLE 67 cis- and trans-4-Cyclohexyl-1-[(3-methylpyridyl)amino]cyclohexane

Following the procedure of Example 33, but starting with 3-aminomethylpyridine and 4-cyclohexylcyclohexanone, the title compounds are produced; cis: IR (Liquid film) 2923, 2851, 1576, 1478, 1448, 1423, 791, 787, 714, 630 $cm^{-1}$(PLA2); trans: mp 65°-67° C.; IR (mull) 3267, 3033, 2815, 2782, 1583, 1575, 1504, 1423, 1364, 1133, 1030, 845, 790 $cm^{-1}$. (PLA2) (trans, diabetes)

EXAMPLE 68

N-(3-Aminopropyl)-3-methoxyestra-1,3,5(10)-trien-17β-amine and
N,N'-bis(3-methoxy-1,3,5(10)-estratrien-17-yl)-1,3-propanediamine A stirred mixture containing 17.04 g of estrone 3-methyl ether, 41.6 g of 1,3-propanediamine bis-hydrochloride, 3.75 g of sodium cyanoborohydride, and 60 g of 3 Å molecular sieves in 420 ml of methanol and 300 ml of tetrahydrofuran is heated at reflux for 26 h, then recooled to 25°. Celite (3 tablespoons) is added, and the mixture is filtered through a medium-porosity sintered glass funnel. The solids are washed with an additional 500 ml of 4:3 methanol/tetrahydrofuran, and the combined filtrate is evaporated to dryness. The residue following evaporation of the first filtrate is partitioned between 1000 ml of water (adjusted to pH 12 with sodium hydroxide) and 400 ml of chloroform, and the aqueous layer is further extracted with two 300 ml portions of chloroform. The organic extracts are washed with water, dried over anhydrous sodium sulfate, and concentrated in vacuo.

The crude product is chromatographed on 1.6 kg of 40-60μ silica gel, which is equilibrated with 10 l of 50/45/5 methylene chloride/ethyl acetate/triethylamine and then eluted with 16 l of the same mixture (1×4 l, then 50 ml fractions). Subsequent elution with 20 l of 25/75/5 methanol/methylene chloride/triethylamine is done to remove the more polar product.

Fractions 91-97 yield the dimer second title compound which contains 5-10% of a faster moving impurity tentatively identified as the 17α-isomer.

Fractions 98-220 afford the second title compound, a solid. Recrystallization of a small portion of this material from ethyl acetate affords crystals with mp 125°-140°. (PLA2, diabetes-)

The broad mp range and the observation of an m/z 36 peak in some mass spec scans of the second title compound suggest that it may contain small amounts of the corresponding hydrochloride salt.

Continued elution of the above chromatogram (the first—12 l of the 25/75/5 MeOH/$CH_2Cl_2$/$Et_3N$ solvent) afford a semi-solid residue. Trituration with 10 ml of ethyl acetate, followed by filtration and drying (1 h, 20°-25°, 0.1 mm) yields a white solid with mp 145° (dec). NMR shows that this solid is an approximate 1:1 mixture of the first title compound and $Et_3N^+CH_2ClCl^-$ (from reaction of the $Et_3N$ and $CH_2Cl_2$ used for elution). Rechromatography of this solid on 300 g of silica gel (elution with 38/60/2 MeOH/$CH_2Cl_2$/$NH_4OH$) affords the first title compound as an oil. The mother liquors from the above crystallization are rechromatographed in the same manner and yield additional compound; IR (neat) 1610, 1577, 1501, 1431, 1352, 1336, 1314, 1281, 1256, 1237, 1179, 1161, 1152, 1040, 900, 872, 816, 786 cm$^{-1}$. (PLA2, diabetes)

EXAMPLE 69

N-(3-Aminopropyl)-3-methoxyestra-1,3,5(10)-trien-17β-amine, dihydrochloride

A solution of 400 mg of the first title compound from Example 68 in 2 ml of methanol is treated with 5 ml of 0.5M HCl/methanol (non-aqueous). Precipitation of the salt from the clear solution begins in about 5 min. After most of the product has crystallized, ether is added until the total volume is about 25 ml. The solids are isolated by filtration through a fine-porosity sintered glass funnel and are dried for 28 h at 25° (0.05 mm), thereby affording the title compound, with mp 274°–276° C. (dec). (PLA2, diabetes)

EXAMPLE 70

N,N'-Bis(3-methoxy-1,3,5(10)-estratrien-17-yl)-1,3-propanediamine, disuccinate

A suspension of 448 mg of the second title compound from Example 68 in 5 ml of methanol is diluted with methylene chloride until the solution becomes clear. Most of the methylene chloride is removed by gentle heating, and the hot solution is treated with a solution of 173 mg of succinic acid in 3.5 ml of methanol. The mixture is allowed to cool gradually to 20°–25° as the product precipitates. Ether (15 ml) is added to the stirred mixture, and, after 30 min, the product is isolated via filtration through a fine-porosity sintered glass funnel. The solids are washed with 3:1 ether/methanol and dried for 18 h at 25° (0.08 mm), thereby affording the title compound, mp 191°–193° C. (PLA2)

EXAMPLE 71

N-(4-Aminobutyl)-3-methoxyestra-1,3,5(10)-trien-17β-amine and
N,N'-(1,4-butanediyl)bis[3-methoxyestra-1,3,5(10)-trien-17β-amine]

A 1000 ml round-bottomed, 3-necked flask, equipped with a magnetic stirrer and a reflux condenser, is flame-dried and then cooled in an atmosphere of nitrogen. The flask is charged with 9.4 g of estrone 3-methyl ether suspended in 165 ml of tetrahydrofuran and 230 ml of methanol. To this suspension is added 33 g of 3 Å molecular sieves, followed by 25 g of 1,4-diaminobutane dihydrochloride. The pH of the solution is adjusted to 5.5 with glacial acetic acid, and 2.1 g of sodium cyanoborohydride is added in one portion. The reaction is refluxed for 16 h.

The reaction mixture is cooled and filtered through Celite, and the solids are washed with 700 ml of 57% methanol/tetrahydrofuran. The filtrate is concentrated in vacuo. The resulting solid is partitioned between chloroform and water (pH 12). The aqueous layer is extracted several times with chloroform. The combined organic layers are dried over magnesium sulfate and concentrated in vacuo.

The crude product is chromatographed on 170 g of 70–230 mesh silica gel. The column is packed and eluted with (67:33:2) methylene chloride/methanol/conc. ammonium hydroxide (10 ml fractions).

Fractions 25–50 are combined based on their TLC homogeneity and afford the second title compound. Fractions 301–500 are combined based on their TLC homogeneity and afford the first title compound; first title compound: mp 76°–78° (PLA2); second title compound: mp>300° C.; IR (mineral oil mull) 3494, 3352, 3235, 3035, 2813, 2769, 2710, 1615, 1507, 1321, 1290, 1257, 1244, 1040, 844, 831 and 632 cm$^{-1}$. (PLA2)

EXAMPLE 72

N-[4-Aminobutyl]-3-methoxyestra-1,3,5(10)-trien-17β-amine,disuccinate

A 10 ml round-bottomed, 2-necked flask, equipped with a magnetic stirrer is flame dried and then cooled in an atmosphere of nitrogen. The flask is charged with 100 mg of the first title compound from Example 71 dissolved in 1 ml of methanol. Then a solution containing 66 mg of succinic acid in 2 ml of methanol (warmed to dissolve) is added in one portion. The reaction mixture is stirred for 1.5 h at 20°–25°. A white precipitate results, and the reaction mixture is concentrated in vacuo.

The resulting white solid is recrystallized from methanol/ether, dried (25° C., 0.1 mm, 64 h) and affords the title compound, mp 141.5°–162.2° C. (PLA2)

EXAMPLE 73

N,N'-(1,4-Butanediyl)-bis[3-methoxyestra-1,3,5(10)-trien-17β-amine]disuccinate

Following the general procedure of Example 72, but starting with N,N'-(1,4-butanediyl)bis[3-methoxyestra-1,3,5(10)-trien-17β-amine], the title compound is produced, mp 248.0°–253.0° C. (PLA2-)

EXAMPLE 74

N-(5-Aminopentyl)-3-methoxyestra-1,3,5(10)-trien-17β-amine

Following the general procedure of Example 33, but starting with 1,5-diaminopentane, the title compound is produced; mp 125.0°–222.0°; IR (mineral oil mull) 3029, 2755, 2688, 2608, 2560, 1611, 1500, 1367, 1357, 1350, 1336, 1314, 1283, 1280, 1259, 1248, 1238, 1153, 1036, and 814 cm$^{-1}$. (PLA2)

EXAMPLE 75

N-(5-Aminopentyl)-3-methoxyestra-1,3,5(10)-triene-17β-amine, dihydrochloride

A 25 ml round-bottomed, 2-necked flask, equipped with a magnetic stirrer, is flame dried and then cooled in an atmosphere of nitrogen. The flask is charged with 606 mg of the title compound from Example 74 dissolved in 10 ml of methanol. To this solution is added 6.8 ml of a 0.53M anhydrous hydrochloric acid solution (methanol) in one portion. The reaction mixture is stirred for 2 h at 20°–25°.

The reaction mixture is diluted with 150 ml of diethyl ether, the precipitate is filtered, dried (25° C., 0.1 mm, 16 h) and affords the title compound; mp 135.6° C. (dec). (PLA2)

EXAMPLE 76

N-(3-Methoxy-1,3,5(10)-estratrien-17-yl)-1,6-hexanediamine and the corresponding dihydrochloride salt Following the general procedure of Example 33, but starting with 1,6-hexanediamine, the title compound is produced, mp 93°–94° C. (PLA2)

The dihydrochloride salt is made by dissolving the title compound (52.2 mg) in 0.5 ml of methanol and adding 0.56 ml of 0.5M hydrogen chloride in methanol. The solution is stirred for 10 minutes at 20°–25°. Addition of diethyl ether is carried out dropwise until the cloud point is reached at which time a white precipitate forms. The solid is filtered, washed with diethyl ether, and dried under high vacuum to provide the dihydrochloride salt, mp 231°–237° C. (PLA2)

EXAMPLE 77

N-(3-Methoxy-1,3,5(10)-estratrien-17-yl)-1,8-octanediamine

Following the general procedure of Example 33, but starting with 1,8-octanediamine, the title compound is produced, mp 47.5°–49.0° C. (PLA2)

EXAMPLE 78

N-(3-Methoxy-1,3,5(10)-estratrien-17-yl)-1,10-decanediamine

Following the general procedure of Example 33, but starting with 1,10-decanediamine, the title compound is produced, mp 55.5°–57.5° C. (PLA2)

EXAMPLE 79

N-(4-Amino-4-carbomethoxybutyl)-3-methoxyestra-1,3,5(10)-trien-17β-amine and 17-(3-Amino-[2-oxopiperidinyl)-3-methoxyestra-1,3,5(10)-triene Following the general procedure of Example 33, but starting with ornithine methyl ester, the title compounds are produced; first title compound: NMR (CDCl$_3$, TMS) δ 7.3–6.55, 3.75, 3.70 and 0.75 ppm (PLA2); second title compound: NMR (CDCl$_3$, TMS) δ 7.4–6.6, 3.75 and 0.75 ppm. (PLA2-)

EXAMPLE 80

N-(3-Methoxy-1,3,5(10)-estratrien-17-yl)-N'-dodecyl-1,3-propanediamine and the corresponding dihydrochloride salt Following the general procedure of Example 33, but starting with N-dodecyl-1,3-propanediamine, the first title compound is produced; NMR (CDCl$_3$, TMS) δ 7.37–7.17, 6.87–6.63, 3.78, 3.0–2.53, 2.43–1.1, 1.0–0.8, 0.75. (PLA2-)

The dihydrochloride salt is made by dissolving the first title compound in methanol and adding 0.5 ml of 0.5M anhydrous hydrogen chloride in methanol to produce a solid, mp 217°–221° C.

EXAMPLE 81

N-Acetyl-N'-(3-methoxy-1,3,5(10)-estratrien-17-yl)-1,6-hexanediamine

The starting diamine from Example 76 (0.142 g) is dissolved in 5 ml of methanol and the mixture cooled in an ice bath. With continued cooling, acetic anhydride (63.2 mg) is added to the above mixture, and stirring is continued for 35 minutes, at which time TLC indicates the reaction is complete. The solution is made basic with 2M sodium hydroxide to a pH of 13–14. The solution is extracted with methylene chloride (4×) and the organic phase washed with water and brine, dried (Na$_2$SO$_4$), filtered, and concentrated to give 150 mg of an oil. In an identical manner a smaller amount of the starting diamine (52.9 mg) and acetic anhydride (22 mg) are reacted to give upon workup 52.8 mg of an oil.

The above oils are combined and chromatographed on 25 g of 40–60μ silica gel eluting with methylene chloride containing 6% of a methanol-ammonium hydroxide (9:1) mixture. An initial fraction of 50 ml is collected followed by 2 ml fractions. Fractions 51–105 are homogeneous by TLC and are combined and concentrated to provide the title compound; IR ñmax(neat) 3291, 2928, 2860, 1652, 1609, 1573, 1556, 1501, 1464, 1453, 1447, 1435, 1369, 1282, 1256, 1237, 1151, 1040, 734 and 726 cm$^{-1}$. (PLA2)

EXAMPLE 82

N-[6-(Formylamino)hexyl]-3-methoxy-1,3,5(10)-estratrien-17β-amine

All glassware used in this reaction is flame dried under nitrogen. The procedure used is based on work by M. Waki and J. Meienhofer, J. Org. Chem., 42, 2019 (1977). A two-necked round bottomed flask, equipped with a nitrogen inlet tube and magnetic stir bar is charged with 1-cyclohexyl-3-(2-morpholinoethyl)carbodiimide metho-p-toluene sulfonate (0.338 g) and 2 ml of chloroform. The mixture is cooled in an ice bath and formic acid (74.6 mg) in 2 ml of chloroform is added dropwise. After stirring the above mixture for 10 minutes, the contents are added to a constant pressure addition funnel. The carbodiimide-formic acid solution is added to an ice-bath-cooled solution of the starting diamine from Example 76 (0.153 g) in 2 ml of pyridine. The entire reaction mixture is stirred for 4½ hours with cooling in an ice bath. By TLC, the reaction is not complete and is allowed to warm to 20°–25° for 30 minutes prior to workup.

The reaction contents are poured into a methylene chloride:ethyl acetate (1:1) mixture and water is added. The water layer is adjusted to a pH of 10, and the layers are separated. The water layer is adjusted to pH 13 and extracted with a fresh portion of methylene chloride-ethyl acetate (1:1). The combined organic layers are washed several times with brine, but fail to remove a suspended solid in the organic layer. After allowing the organic phase to sit in the refrigerator overnight, a white solid settles to the bottom of the flask. The solution is decanted from the flask without transferring the solid (the solid is water soluble). The organic phase is washed with water and brine, dried (Na$_2$SO$_4$), filtered, and concentrated to give an oil. In a similar manner a comparable amount of the starting diamine (0.204 g) is reacted to form the formamide and gives an oil.

The above oils are combined and chromatographed on 20 g of 40–60 μm silica gel eluting with methylene chloride containing 5% of a methanol-ammonium hydroxide (9:1) mixture. An initial fraction of 80 ml is collected followed by 2 ml fractions. Fractions 46–80 contain the desired product along with a minor impurity of higher Rf. The fractions are combined and concentrated to give the title compound as a solid; IR ñmax (mull) 3283, 1667, 1609, 1576, 1537, 1501, 1354, 1312, 1281, 1255, 1237, 1151, 1132, 1039, 816, 780 and 710 cm$^{-1}$. (PLA2)

EXAMPLE 83

N-[6-(Ethoxycarbonylamino)hexyl]-3-methoxy-1,3,5(10)-estratrien-17β-amine

A flame-dried 10 ml round-buttomed flask, equipped with a magnetic stir bar and nitrogen inlet tube is charged with the starting diamine from Example 76 (0.151 g) in 3 ml of methylene chloride. The mixture is cooled in an ice bath and triethylamine (45.6 mg) in 1.5 ml of methylene chloride, followed by ethyl chloroformate (47.0 mg) in 1.5 ml of methylene chloride is added. The mixture is stirred for 30 minutes with cooling (by TLC the reaction is complete after 15 minutes). The contents are poured into water and extracted with methylene chloride (3×). The combined organic phase is washed with water and brine, dried ($Na_2SO_4$), filtered, and concentrated to give an oil. In an identical manner a smaller amount of the starting diamine (42.2 mg) is reacted with triethylamine and ethyl chloroformate to give an oil.

The above oils are combined and chromatographed on 25 g of 40–60µ silica gel eluting with methylene chloride containing 5% of a methanol-ammonium hydroxide (9:1) mixture. An initial fraction of 80 ml is collected followed by 2 ml fractions. Fractions 6–110 are homogeneous by TLC and are combined and concentrated to provide the title compound as a solid; IR ñmax (neat) 3339, 2976, 2930, 2860, 2814, 1722, 1706, 1610, 1516, 1501, 1464, 1452, 1313, 1304, 1280, 1256, 1239, 1151, 1134, 1122, 1105, 1040 and 778 $cm^{-1}$. (PLA2)

EXAMPLE 84

N-[6-(2,5-Dimethylpyrrolyl)hexyl]-3-methoxy-1,3,5(10)-estratrien-17β-amine

The procedure used is based on work by S. Breukelman, G. Meakins, and M. Tire, J.C.S. Chem. Commun., 800 (1982). The starting diamine from Example 76 (0.139 g) is dissolved in 2.5 ml of benzene. To this solution is added 2,5-hexanedione (75.5 mg) in 2.5 ml of benzene and acetic acid (16.4 mg) in 1 ml of benzene. The mixture is heated to reflux for 10 minutes and then cooled (by TLC the reaction is complete by the time the mixture achieves reflux temperature). Water is added to the mixture, and the water layer is made basic with 2M sodium hydroxide to a pH of 13-14. The entire mixture is extracted with methylene chloride (4×) and the organic phase washed with water and brine, dried ($Na_2SO_4$), filtered and concentrated to give an oil.

The above oil is chromatographed on 25 g of 40–60µ silica gel, eluting with methylene chloride containing 2.5% of a methanol-ammonium hydroxide (9:1) mixture. An initial fraction of 40 ml is collected followed by 2 ml fractions. Fractions 31–117 are homogeneous by TLC and are combined and concentrated to give an oil; IR nmax (neat) 2929, 2856, 2817, 1610, 1518, 1501, 1464, 1454, 1409, 1394, 1313, 1300, 1281, 1256, 1237, 1151, 1040, 816, 745 and 725 $cm^{-1}$. (PLA2)

EXAMPLE 85

N,N',N'-Tris(methoxycarbonylmethyl)-N-(3-methoxy-1,3,5(10)-estratrien-17-yl)-1,3-propanediamine A solution of 342 mg of diamine from Example 68, 0.8 ml of diisopropylethylamine, and 0.28 ml of methyl bromoacetate in 20 ml of tetrahydrofuran is stirred at 20°-25° for two weeks. The mixture is then poured into 100 ml of 1:1 water/brine and extracted with two 100 ml portions of ethyl acetate. The extracts are washed with brine, dried over sodium sulfate, and concentrated in vacuo.

The crude product is chromatographed on a 75 g column of silica gel. The column is packed and eluted (7 ml fractions) with 40% ethyl acetate/hexane. Fractions 59–100, clean by TLC, are combined and yield the title compound, an oil; IR nmax (neat) 1740, 1602, 1570, 1500, 1430, 1280, 1260, 1240, 1200, 1170, 1020, 960 and 870 $cm^{-1}$. (PLA2-)

EXAMPLE 86

N,N',N'-Tris(carboxymethyl)-N-(3-methoxy-1,3,5(10)-estratrien-17-yl)-1,3-propanediamine, tris (potassium salt)

A solution of 100 mg (0.179 mmol) of the title compound from Example 85 in 4.0 ml of methanol is treated with 0.537 ml of 1.0M aqueous potassium hydroxide and the initially cloudy solution is stirred at 25° for 20 hours. (The mixture becomes clear by 30 min). Following removal of the methanol in vacuo, the residue is taken up in 5 ml of water and freeze-dried, thereby affording the title compound; mp>325°; NMR ($D_2O$, TMS) δ 7.3–6.5, 3.65, 3.5–3.0. (PLA2-)

EXAMPLE 87

3-Methoxy-N-methyl-estra-1,3,5(10)-trien-17β-amine and the corresponding 17α-epimer Following the general procedure of Example 33, but starting with methylamine hydrochloride, the second title compound is produced; IR ñmax (mull) 3309, 1608, 1503, 1478, 1448, 1445, 1433, 1310, 1289, 1252, 1236, 1232, 1160, 1104, 1086, 1030, 888, 862, 824, 740 $cm^{-1}$. (PLA2, diabetes)

Continued elution of the large column above yields the first title compound. Recrystallization from 50 ml of ethyl acetate gives white needles with mp 136°-137°. (PLA2, diabetes)

EXAMPLE 88

N-[3-(3-Aminopropyl)amino]propyl-3-methoxyestra-1,3,5(10)-trien-17β-amine and the corresponding N,N'-dimer Following the general procedure of Example 71, but starting with 3,3'-iminobispropylamine, the title compounds are produced; first title compound: mp 53.2°-110.0° C.; IR nmax (mull) 3365, 3292, 3251, 3026, 2821, 2759, 1609, 1581, 1501, 1367, 1359, 1313, 1287, 1255, 1236, 1155, 1124, 1119, 1035, 817 and 786 $cm^{-1}$ (PLA2); second title compound: mp 119.5°-229.0° C.; IR ñmax (mull) 3278, 3052, 3026, 2646, 1610, 1501, 1351, 1314, 1282, 1256, 1237, 1160, 1152, 1033, 817 and 785 $cm^{-1}$. (PLA2)

EXAMPLE 89

N-[3-(3-Aminopropyl)amino]propyl-3-methoxyestra-1,3,5(10)-trien-17β-amine, trisuccinate A 25 ml round-bottomed, 2-necked flask, equipped with a magnetic stirrer is flame dried and then cooled in an atmosphere of nitrogen. The flask is then charged with 500 mg of the first title compound from Example 88 dissolved in 10 ml of methanol. Then a solution containing 443 mg of succinic acid in 2 ml of methanol (warmed to dissolve) is added in one portion. The reaction mixture is stirred for 1 h at 20°-25° (within 20 min a solid precipitates).

The reaction mixture is diluted with 10 ml of diethyl ether, the precipitate is filtered, dried (25° C.,—10 mm, 100 h) and affords the title compound, mp 150.1°-153.0° C. (PLA2)

EXAMPLE 90

N-[3-(3-Aminopropyl)amino]propyl-3-methoxyestra-1,3,5(10)-trien-17β-amine, trihydrochloride Following the general procedure of Example 89, but starting with anhydrous hydrochloric acid solution, the title compound is produced; mp 262.5°–267.5° C. (PLA2)

EXAMPLE 91

N-(3-Methoxy)-1,3,5(10)-estratrien-17-yl)-N'-(3-dimethylamino)propyl-1,3-propanediamine and trihydrochloride salt Following the general procedure of Example 33, but starting with the triamine, the first title compound is produced; NMR (CDCl$_3$,TMS) δ 7.33–7.17, 6.83–6.6, 3.73, 2.97–1.1, 2.2, 0.73. (PLA2)

The trihydrochloride salt is made by dissolving the first title compound (52 mg) in 0.5 ml of methanol and adding 0.75 ml of anhydrous 0.5M hydrogen chloride in methanol. The solution is stirred for 10 minutes at 20°–25°. Addition of diethyl ether is carried out dropwise until the cloud point of the solution is reached. A few additional drops of ether cause a white precipitate to form. The solid is filtered, washed with diethyl ether, and dried under high vacuum to provide a powder, mp 265°–268° C. (PLA2)

EXAMPLE 92

N-(3-Methoxy-1,3,5(10)-estratrien-17-yl)-diethylenetriamine and the corresponding trihydrochloride salt Following the general procedure of Example 33, but starting with diethylenetriamine, the title compound is produced; mp 120°–147° C.; IR ñmax (mull) 3262, 3196, 3118, 3054, 1609, 1578, 1561, 1398, 1366, 1353, 1338, 1312, 1286, 1252, 1237, 1032 and 816 cm$^{-1}$. (PLA2)

The trihydrochloride salt is prepared by standard methods, mp 180°–185° C. (PLA2)

EXAMPLE 93

N-(3-Methoxy-1,3,5(10)-estratrien-17-yl)-1,4-bis(3-aminopropyl)piperazine

Following the general procedure of Example 33, but starting with 1,4-bis(3-aminopropyl)piperazine, the title compound is produced, mp 62°–138° C.; IR ñmax (mull) 3335, 3026, 2820, 2772, 1609, 1501, 1349, 1315, 1286, 1254, 1237, 1152, 1147, 1034, 819 and 785 cm$^{-1}$. (PLA2)

EXAMPLE 94

N-(5,9-Diazanonan-1-yl)-3-methoxyestra-1,3,5(10)-trien-17β-amine

Following the general procedure of Example 33, but starting with spermidine, the title compound is produced; IR nmax (neat) 2929, 2866, 2849, 2816, 1664, 1610, 1576, 1501, 1466, 1453, 1436, 1314, 1281, 1256, 1237, 1152, 1132, 1040, 816, 814, 784, 779 cm$^{-1}$. (PLA2)

EXAMPLE 95

N-(5,9-Diazanonan-1-yl)-3-methoxy-estra-1,3,5(10)-trien-17β-amine trihydrochloride A solution of the title compound from Example 94, (0.17 g) in absolute methanol (1 ml) is treated at 20°–25° under argon with 0.53M anhydrous HCl in methanol (2.8 ml) until acidic by pH paper. The resulting solution is stirred for—5 minutes at 20°–25°, treated with anhydrous diethyl ether (45 ml) over 30 minutes, and the resulting suspension is stirred for 15 minutes under argon. The suspension is filtered, and the filtercake is washed with anhydrous ether (—15 ml). The light yellow powder is dried under high vacuum overnight to give the title compound, mp 230°–235° C. (PLA2)

EXAMPLE 96

3-Methoxy-N-(4,9,13-triazatridecan-1-yl)-estra-1,3,5(10)-trien-17β-amine

Following the general procedure of Example 33, but starting with spermine, the title compound is produced; IR ñmax (neat) 2928, 2865, 2846, 2814, 1610, 1501, 1466, 1454, 1256, 1237, 1152, 1123, 1040, 817, 785, 782 cm$^{-1}$. (PLA2)

EXAMPLE 97

3-Methoxy-N-(4,9,13-triazatridecan-1-yl)-estra-1,3,5(10)-trien-17β-amine, tetrahydrochloride A solution of the title compound from Example 96 (0.184 g) in absolute methanol (1 ml) is treated at 20°–25° under nitrogen with 0.53M anhydrous HCl in methanol (3.1 ml) until acid pH paper. The resulting solution becomes turbid within a minute and a precipitate begins to form. The resulting suspension is stirred for—5 minutes, and anhydrous ether (45 ml) is added in portions over 30 minutes. The suspension is stirred for—15 minutes and filtered. The filtercake is washed with anhydrous ether (—15 ml) and the residue is dried under high vacuum to give the title compound; NMR (d$_6$DMSO, TMS) δ 0.90, 1.10–3.60, 3.70, 6.60–6.87, 7.23. (PLA2)

EXAMPLE 98

N-Formyl-N',N'-dimethyl-N-[1-(3-methoxy-1,3,5(10)-estratrien-17-yl)ethyl]-1,3-propanediamine Following the general procedure of Preparation 1, but starting with the title compound from Preparation 8 and 3-dimethylaminopropylamine, the title compound is produced; NMR (CDCl$_3$, TMS) δ 8.3–8.1, 7.33–7.13, 6.87–6.63, 3.77, 3.6–2.63, 2.26, 2.43–0.6; TLC Rf=0.19 (more polar isomer) and 0.23 (less polar isomer), run in methylene chloride with 5% methanol-ammonium hydroxide (9:1), Rf=0.52 (more polar isomer) and Rf=0.54 (less polar isomer), run in methylene chloride with 10% methanol-ammonium hydroxide (9:1).

EXAMPLE 99

N,N',N'-Trimethyl-N-[1-(3-methoxy-1,3,5(10)-estra-trien-17-yl)ethyl]-1,3-propanediamine Following the general procedure of Preparation 2, but starting with the title compound of Example 98, the title compounds are produced; less polar isomer; NMR (CDCl$_3$, TMS) δ 7.37–7.2, 6.83–6.6, 3.77, 2.33, 2.12, 3.0–1.07, 0.9–0.77, 0.72 (PLA2); more polar isomer: NMR (CDCl$_3$, TMS) δ 7.37–7.17, 6.87–6.65, 3.8, 2.28, 2.17, 3.0–1.07, 1.0–0.83, 0.7. (PLA2)

EXAMPLE 100

N-(N',N'-3-Dimethylamino)propyl-α-methyl-3-methoxy-1,3,5(10-estratrien-17-methaneamine Following the general procedure of Example 33, but starting with the first title compound of Preparation 8, the title compounds are produced; less polar isomer: NMR (CDCl$_3$, TMS) δ 7.33–7.2, 6.87–6.63, 3.87, 3.4–3.1, 3.0–1.1, 2.23, 1.13–1.0, 0.73 (PLA2); more polar isomer: NMR (CDCl$_3$, TMS) δ 7.4–7.2, 6.87–6.67, 3.82, 3.0–1.1, 2.25, 1.22–1.08, 0.72. (PLA2)

EXAMPLE 101

3-Methoxy-17-(3-dimethylamino-1-oxopropyl)-1,3,5(10)-estratriene

A 15 ml round-bottomed flask, equipped with a magnetic stir bar, condenser, and nitrogen inlet tube, is charged with the first title compound from Preparation 8 (0.454 g), dimethylamine hydrochloride (0.408 g), paraformaldehyde (0.201 g), 6 ml of absolute ethanol, and 90 µl of 0.5M anhydrous hydrogen chloride in methanol. The above mixture is heated to 80° C. for 52 hours. By TLC, a large amount of starting material is still present. The solution is cooled and additional dimethylamine hydrochloride (0.134 g) and paraformaldehyde (97 mg) are added. The mixture is again heated to 80° C. overnight. Analysis by TLC indicates starting material is still present, but enough product is present for workup. After cooling, the solution is made basic using aqueous 2M sodium hydroxide. The mixture is extracted with methylene chloride (3×) and the organic phase washed with water and brine, dried (Na$_2$SO$_4$), filtered, and concentrated to give 541 mg of an oil.

The oil is chromatographed on 60 g of 40-60µ silica gel eluting with 2% triethylamine/ethyl acetate. An initial fraction of 75 ml is collected, followed by 4 ml fractions. Fractions 61-90 are nearly homogeneous by TLC and are combined and concentrated to provide a solid, mp 78°-82° C. (PLA2)

EXAMPLE 102

3-Methoxyestra-1,3,5(10)-trien-17β-ol, N,N'-bis(t-butoxycarbonyl)-ornithine ester A 10 ml round-bottomed, 2-necked flask, equipped with a magnetic stirrer is flame dried and then cooled in an atmosphere of nitrogen. The flask is charged with 116 mg of N,N'-bis(t-butoxycarbonyl) ornithine (Preparation 9) dissolved in 3 ml of ethylene dichloride. To the stirred mixture is added 5 mg of N,N-dimethylaminopyridine, 100 mg of the appropriate 17β-alcohol and 148 mg of 1-cyclohexyl-3-(2-morpholinoethyl) carbodiimide metho-p-toluenesulfonate. The reaction mixture is stirred at 40° C. for 16 h.

The reaction mixture is cooled and then washed 4×70 ml with water. The organic layer is separated, washed with brine, dried over magnesium sulfate and concentrated in vacuo.

The crude product is chromatographed on 40 g of 230-400 mesh silica gel. The column is packed and eluted with 60% hexane/methyl ethyl ketone (2 ml fractions).

Fractions 30-42 are combined based on their TLC homogeneity and afford the title compound; NMR (CDCl$_3$, TMS) δ 7.4-6.6, 3.75, 1.5 and 0.8 ppm.

EXAMPLE 103

3-Methoxyestra-1,3,5(10)-trien-17β-ol, ornithine ester bis(trifluoroacetate)

A 25 ml round-bottomed, 2-necked flask, equipped with a magnetic stirrer, is flame dried and then cooled in an atmosphere of nitrogen. The flask is charged with 75 mg of di(BOC) ester dissolved in 8.3 ml of methylene chloride and cooled to 0° C. (ice/water bath). To the stirred solution is added 4.6 g of trifluoroacetic acid. The mixture is stirred for 20 min at 0° C.

The reaction mixture is then concentrated in vacuo. The resulting residue is triturated with ether and affords the title compound. Recrystallization from chloroform/hexane affords pure material, which decomposes between 175°-180° C.; NMR (CD$_3$OD, TMS) δ 7.3-6.55, 3.75 and 0.95 ppm. (PLA2)

EXAMPLE 104

3-Methoxyestra-1,3,5(10)-trien-17β-ol, 3-(dimethyl-amino)propyl ether, methane sulfonate A degassed solution of 3-methoxyestra-1,3,5(10)-trien-17β-ol, (0.10 g) in freshly distilled THF (2 ml) is added at 20°-25° under N$_2$ to a suspension of 50% NaH (0.05 g) in THF (2 ml). The resulting suspension is stirred for 2 h at 25° and treated with dimethyltrimethyleneammonium methanesulfonate (0.38 g) (see Preparation 9). The resulting suspension is stirred at reflux overnight with the reaction going—60-65%. The reaction is permitted to go an additional 24 h, permitted to cool to 20°-25° and is partitioned between ice-cold, saturated, aqueous sodium bicarbonate (100 ml) and chloroform (100 ml). The layers are separated, and the aqueous layer is extracted with chloroform (2×100 ml). The organics are washed with aqueous saturated sodium bicarbonate (100 ml), dried over anhydrous potassium carbonate, filtered and concentrated to give crude product.

The crude product is chromatographed on silica gel (45) in 5% ethyl acetate/hexane while collecting 10 ml fractions. Fractions 10-12 are combined and concentrated to give starting material. Fractions 18-35 are combined and concentrated to give the title compound; IR ñmax (mull) 2930, 2855, 2850, 2745, 1601, 1574, 1495, 1460, 1440, 1370, 1350, 1302, 1275, 1245, 1225, 1130, 1085, 1025, 940 cm$^{-1}$.

EXAMPLE 105

N-[3-Dimethylamino)propyl]-3-methoxyestra-1,3,5(10)-trien-17α-amine

A solution of 2.0 g (7.0 mmol) of 3-methoxyestra-1,3,5(10)-trien-17β-ol in 35 ml of methylene chloride is cooled, under nitrogen, to 0° and treated with 1.46 ml of triethylamine, followed by 0.606 ml of methanesulfonyl chloride, the latter added dropwise over about 30 seconds. The mixture is stirred at 0° for 30 min, by which time TLC analysis (5% acetone/methylene chloride) shows the absence of starting alcohol and the presence of a single faster moving spot. Ice chips (—5 g) are added to the reaction mixture and stirring is continued for 15 min at 0°. The reaction mixture is then diluted with 100 ml of methylene chloride and washed with cold dilute aqueous potassium bisulfate (2×50 ml), followed by a single water wash. The combined organic layer is dried over anhydrous sodium sulfate and evaporated to dryness. The crude mesylate, a solid, is homogeneous by TLC and is used in the next step without purification.

The crude mesylate is dissolved in 20 ml of freshly distilled N,N-dimethyl-1,3-propanediamine (bp 129°-130° at atmospheric pressure), and the mixture is heated at reflux in an atmosphere of nitrogen for 12 days. The reaction mixture is cooled to 20°-25° and concentrated in vacuo. The residue is diluted with water, adjusted to pH 12-13, and extracted with chloroform. The extracts are washed with water, dried over anhydrous sodium sulfate, and evaporated to dryness.

The crude product containing a small amount of the desired 17α-amine is chromatographed on a column containing 80 g of silica gel. Elution with 300 ml of 5% acetone/methylene chloride yields an oil, 3-methoxyestra-1,3,5(10), 16-tetraene; IR n̄max (neat) 3025, 1602, 1500, 1445, 1425, 1280, 1260, 1240, 1040 cm$^{-1}$; NMR (CDCl$_3$, TMS) δ 7.4–6.6, 6.1–5.4, 3.80, 0.78 ppm.

Elution of the above chromatogram with 15/85/1.5 methanol/methylene chloride/ammonium hydroxide gave impure title compound.

This material is rechromatographed on 80 g of silica gel, eluting with 25/75/5 methanol/ethyl acetate/triethylamine (8 ml fractions). Fractions 37–55 are combined and yield pure title compound which crystallizes on standing. Recrystallization from ethyl acetate affords crystals with mp 164°–168°. (PLA2)

EXAMPLE 106

N-[3-Dimethylamino)propyl]-3-methoxyestra-1,3,5(10)-trien-17α-amine, disuccinate To a stirred solution of 240 mg of the title compound from Example 105 in 2 ml of methanol is added a warm solution of 153 mg of succinic acid in 3 ml of methanol. The homogeneous mixture is stirred for 20 min at 25°, and is then concentrated to about one-third of the original volume on the rotary evaporator. The crystalline product is recrystallized from methanol/ether, and the solids are filtered, washed with 60/40 ether/methanol and dried (0.08 mm, 2 h, 25°) to produce the title compound, mp 160.5°–161.0° C. (PLA2)

EXAMPLE 107

N-[3-Dimethylamine)propyl]-N-formyl-11β-hydroxy-5α-androstan-17β-amine

Following the general procedure of Preparation 1, but starting with 11β-hydroxy-5α-androstan-17-one, the title compound is produced, mp 142°–144° C.; NMR (CDCl$_3$, TMS) 0.95, 1.03, 1.04–2.45, 3.32, 4.30, 8.15.

EXAMPLE 108

N-[3-(Dimethylamino)propyl]-N-methyl-11β-hydroxy-5α-androstan17β-amine

Following the general procedure of Preparation 2, but starting with the title compound of Example 107, the title compound is produced, mp 130°–131° C. (PLA2)

EXAMPLE 109

N-(3-Methoxy-1,3,5(10)-estratrien-17-yl)-N-methylacrylamide

A 25 ml two-neck round bottomed flask, equipped with a magnetic stir bar, nitrogen inlet tube, and 10 ml addition funnel is charged with the first title compound of Example 87 (1.0 g), triethylamine (0.40 g), and 5 ml of methylene chloride. Dropwise addition of acryloyl chloride (0.335 g) in 5 ml of methylene chloride to the above solution is followed by stirring at 20°–25° for 30 minutes. Additional methylene chloride is added to the reaction mixture and the organic solution is washed with water and brine, dried (Na$_2$SO$_4$), filtered, and concentrated to provide a solid.

The solid is chromatographed on 140 g of 70–230 mesh silica gel eluting with 15% ethyl acetate/methylene chloride. An initial fraction of 200 ml is collected, followed by 10 ml fractions. Fractions 48–95 are homogeneous by TLC and are combined and concentrated to provide the title compound as a solid; mp 130°–132° C. (PLA2-)

EXAMPLE 110

N-Cyclopentadecyl-1,3-propanediamine and N,N'-bis(cyclopentadecyl)-1,3-propanediamine Following the general procedure of Example 71, but starting with cyclopentadecanone and 1,3-diaminopropane bis(hydrochloride), the second title compound is produced, mp 242°–248°. (PLA2)

Continued elution of the chromatogram, fractions 49–78 afford the first title compound; NMR (CDCl$_3$, TMS) δ 2.9–2.4, 1.40 and 1.7–1.2 ppm. (PLA2)

EXAMPLE 111

N,N'-Bis(cyclopentadecyl)-1,3-propanediamine, dihydrochloride

A solution of 500 mg of the second title compound from Example 110 in 5 ml of methanol is treated with 5 ml of 0.5M HCl in methanol (prepared by bubbling HCl gas into methanol and then titrating the solution). The clear solution is stirred for 20 min, and then ether is added until solids begin to precipitate. The mixture is stirred for 18 h at 20°–25° and then diluted with 20 ml more ether. The solids are filtered, washed with ether and dried (0.05 mm, 18 h, 25°), thereby affording the title compound; mp 237°–240°. (PLA2)

EXAMPLE 112

N-Cyclopentadecyl-1,3-propanediamine, dihydrochloride

A solution of 564 mg of the first title compound from Example 110 in 5 ml of methanol is treated with 10 ml of 0.5M HCl in methanol added in one portion. After 20 min, the stirred, clear solution is gradually diluted with ether at the rate of 3 ml/min until about 75 ml is added. (Precipitation of the salt begins after the addition of about 10 ml of ether.) The suspension is stirred for 1 h at 25°, then filtered, and the solids are washed with 10 ml of 1:1 methanol/ether and dried (0.1 mm, 25°,18 h). The title compound so produced exhibits mp 268°–270° (dec).

Example 113

N-Cyclohexyl-N'-dodecyl-1,3-propanediamine

Following the general procedure of Example 33, but starting with N-dodecyl-1,3-propanediamine and cyclohexanone, the title compound is produced; IR n̄max (neat) 3292, 2925, 2854, 2810, 1466, 1450, 1367, 1130 and 721 cm$^{-1}$. (PLA2)

EXAMPLE 114

Diphenylphosphoric acid, 3-(N,N-dimethylamino)propylamide

A 25 ml round-bottomed, 2-necked flask, equipped with a magnetic stirrer, is purged with nitrogen. The flask is charged with 1.34 g of diphenyl chlorophosphate and 10 ml of chloroform. The flask is then cooled to 0° C. (ice/water). 0.64 g of N,N-dimethyl-1,3-propane-diamine is added in one portion and allowed to stir at 0° C. for 10 min. Then 208 mg of calcium hydroxide is added in small portions over a 20 min period. Once the addition is complete, 430 μl of a 12.75M sodium hydroxide solution (aq.) is added over a 10 min period. The reaction mixture is allowed to stir for 30 min at 20°–25°.

The reaction mixture is then dried over magnesium sulfate and concentrated in vacuo. The crude product is chromatographed on a column containing 40 g of 70-230 mesh silica gel. The column is packed and eluted with 75% ethyl acetate/methanol with 2% triethylamine (5 ml fractions).

Fractions 11-26 are combined based on their TLC homogeneity to afford the title compound; IR ñmax (neat) 3223, 2968, 2945, 2861, 2818, 2770, 1591, 1490, 1461, 1456, 1258, 1222, 1196, 1163, 1114, 1070, 1026 and 1007 cm$^{-1}$. (PLA2)

appropriate steroid and amine in the presence of a small amount of p-toluenesulfonic acid over a water separator until water no longer evolves. The solvent is evaporated and the resulting imine is reduced to the amine by the method of Example 33.

| Example | Compound | M.P. |
|---|---|---|
| 116 | 17β-(Phenylamino)-androst-5-en-3β-ol hydrate | 128.5–130 |
| 117 | 3-Methoxy-17β-(phenylamino)-estra-1,3,5(10)-triene (diabetes) | 138–139 |
| 118 | 3-Methoxy-17β-[(3-pyridinyl)amino]-estra-1,3,5(10)-triene (diabetes) | 258–261 |
| 119 | 3-Methoxy-17β-[(4-chlorophenyl)amino]-estra-1,3,5(10)-triene (diabetes) | 137–138.5 |
| 120 | 3-Methoxy-17β-[(4-methoxyphenyl)amino]-estra-1,3,5(10)-triene (diabetes) | 161–163 |
| 121 | 3-Methoxy-17β-[((3-trifluoromethyl)phenyl)-amino]-estra-1,3,5(10)-triene (diabetes) | 113–120 |
| 122 | 3-Methoxy-17β-[(4-methoxycarbonyl)phenylamino]-estra-1,3,5(10)-triene (diabetes) | 183–184.5 |

The following compounds are prepared by starting with the title compound of Example 61, and formaldehyde (Example 123) and acetaldehyde (Example 124), and then reducing by the method of Example 33:

| Example | Compound | M.P. |
|---|---|---|
| 23 | 3-Methoxy-N-methyl-17β-[(phenylmethyl)amino]-estra-1,3,5(10)-triene (PLA2, diabetes) | 149–150.5 |
| 124 | 3-Methoxy-N-ethyl-17β-[(phenylmethyl)amino]-estra-1,3,5(10)-triene (diabetes) | 113.5–115 |

EXAMPLE 115

Tris[3-(N,N-dimethylamino)propyl]-phosphoric triamide

A solution of 1 ml (1.645 g) of phosphorous oxychloride in 50 ml of ether is added over a period of 20 min to a stirred, 0° solution of 4.05 ml (3.29 g) of N,N-dimethyl-1,3-propanediamine in 50 ml of ether. (A vigorous reaction ensues and a voluminous white solid forms.) The reaction mixture is then allowed to warm to 20°-25° and stirring is continued 18 h longer.

The mixture is cooled to 0° and treated with ammonia gas bubbled into the mixture via a pipet for about 10 min. The solids are filtered, washed with two additional 20 ml portions of cold ether, and dried under vacuum, thereby affording a hygroscopic solid, mostly ammonium chloride. The filtrate from above is concentrated in vacuo and affords an oil; IR ñmax (neat) 3223, 2814, 2764, 1447, 1226, 1183, 1154, 1098, 1065, 1043, 1010, 973, 830 cm$^{-1}$. (PLA2)

The following compounds are prepared by first preparing the imine by refluxing a toluene solution of the The following compounds are prepared by following the general procedure of Example 33. The starting amines are 3-(aminomethyl)pyridine (Examples 125-27), benzylamine (Example 128), 2-aminomethylfuran (Example 129), 4-chlorobenzylamine (Examples 130 and 134), 4-(2-aminoethyl)benzenesulfonamide (Examples 131 and 139), 2-thiophenemethylamine (Examples 132 and 138), 3-(trifluoromethyl)benzylamine (Examples 133 and 135), 4-methoxybenzylamine (Example 136), 4-(trifluoromethyl)benzylamine (Example 137), 4-(aminomethyl)benzenesulfonamide hydrochloride (Example 140), 2-(aminomethyl)benzimidazole dihydrochloride hydrate (Example 141), 2-(trifluoromethyl)-benzylamine (Example 142), glycine methyl ester hydrochloride (Example 143), 4-fluorobenzylamine (Example 144), 3,4-dichlorobenzylamine (Example 145), 2,4-dichlorobenzylamine (Example 146), and 2-chlorobenzylamine (Example 147). The starting steroids are 3β-hydroxy-5-androsten-17-one (Examples 125 and 128-33), 3α-hydroxy-5α-androstan-17-one (Example 126), 11β-hydroxy-5α-androstan-17-one (Example 127), and estrone methyl ether (Examples 134-47).

| Example | Compound | M.P. |
|---|---|---|
| 125 | 17β-[(3-Pyridinylmethyl)amino]-androst-5-en-3β-ol | 196–201 |
| 126 | 17β-[(3-Pyridinylmethyl)amino]-5α-androstan-3α-ol | 158–162 |
| 127 | 17β-[(3-Pyridinylmethyl)amino]-5α-androstan-11β-ol | 186–187.5 |
| 128 | 17β-[(Phenylmethyl)amino]-androst-5-en-3β-ol Ethanol solvate (diabetes) | 155.5–157.5 |
| 129 | 17β-[(2-Furylmethyl)amino]-androst-5-en-3β-ol | 106–108 |
| 130 | 17β-[(4-Chlorophenylmethyl)amino]-androst-5-en-3β-ol (diabetes) | 181–185 |
| 131 | 17β-[(2-(4-Aminosulfonylphenyl)ethyl)amino]-androst-5-en-3β-ol (diabetes) | 218–219.5 |
| 132 | 17β-[(2-Thienylmethyl)amino]-androst-5-en-3β-ol hydrate | 143–144.5 |
| 133 | 17β[((3-Trifluoromethyl)phenylmethyl)amino]- | 101–103.5 |

-continued

| Example | Compound | M.P. |
|---|---|---|
| | androst-5-en-3β-ol | |
| 134 | 3-Methoxy-17β-[(4-chlorophenylmethyl)amino]-estra-1,3,5(10)-triene (PLA2-, diabetes) | 131.5–132.5 |
| 135 | 3-Methoxy-17β-[((3-trifluoromethyl)phenylmethyl)amino]-estra-1,3,5(10)-triene (PLA2, diabetes) | 70–71.5 |
| 136 | 3-Methoxy-17β-[(4-methoxyphenylmethyl)amino]-estra-1,3,5(10)-triene (PLA2-, diabetes) | 117.5–118.5 |
| 137 | 3-Methoxy-17β-[((4-trifluoromethyl)phenylmethyl)-amino]-estra-1,3,5(10)-triene (PLA2, diabetes) | 83.5–85 |
| 138 | 3-Methoxy-17β-[(2-thienylmethyl)amino]-estra-1,3,5(10)-triene (PLA2-, diabetes) | 85.5–87 |
| 139 | 3-Methoxy-17β-[(2-(4-aminosulfonylphenyl)ethyl)-amino]-estra-1,3,5(10)-triene (PLA2-, diabetes) | 157–158 |
| 140 | 3-Methoxy-17β-[((4-aminosulfonyl)phenylmethyl)-amino]-estra-1,3,5(10)-triene (PLA2-, diabetes) | 189–192 |
| 141 | 3-Methoxy-17β-[((2-benzimidazolyl)methyl)amino]-estra-1,3,5(10)-triene (diabetes) | 192–196 |
| 142 | 3-Methoxy-17β-[((2-trifluoromethyl)phenyl-methyl)amino]-estra-1,3,5(10)-triene (diabetes) | 112.5–114 |
| 143 | 3-Methoxy-17β-[(methoxycarbonylmethyl)-amino]-estra-1,3,5(10)-triene (diabetes) | 57.5–59.5 |
| 144 | 3-Methoxy-17β-[(4-fluorophenylmethyl)amino]-estra-1,3,5(10)-triene (diabetes) | 71.5–73.5 |
| 145 | 3-Methoxy-17β-[(3,4-dichlorophenylmethyl)amino]-estra-1,3,5(10)-triene (diabetes) | 130.5–132.5 |
| 146 | 3-Methoxy-17β-[(2,4-dichlorophenylmethyl)amino]-estra-1,3,5(10)-triene (diabetes) | 102.5–104.5 |
| 147 | 3-Methoxy-17β-[(2-chlorophenylmethyl)amino]-estra-1,3,5(10)-triene (diabetes) | 136–137 |

The following compounds are prepared by following the general procedure for Example 33. If the starting material is other than estrone methyl ether, it is noted in parentheses following the compound name.

| Example | Compound | M.P. |
|---|---|---|
| 148 | 3-Hydroxy-17β-[((3-trifluoromethyl)phenylmethyl)-amino]-estra-1,3,5(10)-triene tetrahydrofuran solvate (estrone) (diabetes) | 49–52° |
| 149 | 3-Methoxy-17β-[(2-(4-chlorophenyl)ethyl)-amino]-estra-1,3,5(10)-triene (diabetes) | 122–124° |
| 150 | 3-(2,3-dihydroxypropoxy)-17β-[(4-chlorophenyl-methyl)amino]-estra-1,3,5(10)-triene (2,3-dihydroxypropyl estrone ether) (diabetes) | 123–133° |
| 151 | 3-Methoxy-17β-[(4-methoxycarbonylphenylmethyl)-amino]-estra-1,3,5(10)-triene (diabetes) | 122–128° |
| 152 | 3-Methoxy-17β-[(4-bromophenylmethyl)amino]-estra-1,3,5(10)-triene (diabetes) | 143–144.5° |
| 153 | 3-Methoxy-17β-[(3-chlorophenylmethyl)amino]-estra-1,3,5(10)-triene (diabetes) | 60–63° |
| 154 | 3-Methoxy-17β-[(3-phenylpropyl)amino]-estra-1,3,5(10)-triene (diabetes) | 85–90° |
| 155 | 3-Methoxy-17β-[(4-phenylbutyl)amino]-estra-1,3,5(10)-triene (diabetes) | 97–100° |
| 156 | 3-Methoxy-17β-[(4-methylphenylmethyl)amino]-estra-1,3,5(10)-triene (diabetes) | 102–106° |
| 157 | 3-Methoxy-17β-[(1-phenylethyl)amino]-estra-1,3,5(10)-triene (diabetes) | 70–78° |
| 158 | 3-Methoxy-17β-[(2-(1,2-dihydro-2-oxopyrid-1-yl)ethyl)amino]-estra-1,3,5(10)-triene (diabetes) | 130–131° |

The following compounds are prepared by starting with the title compound of Example 135, and formaldehyde (Example 159), acetaldehyde (Example 160), propionaldehyde (Example 161), iso-valeraldehyde (Example 162), octylaldehyde (Example 163), and tetradecyl aldehyde (Example 164), and then reducing by the method of Example 33:

| Example | Compound | M.P. |
|---|---|---|
| 159 | 3-Methoxy-N-methyl-17β-[((3-trifluoromethyl)-phenylmethyl)amino-estra,1,3,5(10)-triene | 112.5–114° |
| 160 | 3-Methoxy-N-ethyl-17β-[((3-trifluoromethyl-phenylmethyl)amino]-estra-1,3,5(10)-triene (diabetes) | 80–87.5° |
| 161 | 3-Methoxy-N-(propyl)-17β-[((3-trifluoromethyl)-phenylmethyl)amino]-estra-1,3,5(10)-triene (diabetes) | 91–92.5° |

-continued

| Example | Compound | M.P. |
|---|---|---|
| 162 | 3-Methoxy-N-(3-methylbutyl)-17β-[((3-trifluoromethyl)phenylmethyl)amino]-estra-1,3,5(10)-triene hydrochloride (diabetes) | 92–102° |
| 163 | 3-Methoxy-N-(octyl)-17β-[((3-trifluoromethyl)phenylmethyl)amino]-estra-1,3,5(10)-triene hydrochloride | 86–309° |
| 164 | 3-Methoxy-N-(tetradecyl)-17β-[((3-trifluoromethyl)phenylmethyl)amino]-estra-1,3,5(10)-triene | 116–119° |

The following compounds are prepared by starting with acetaldehyde and the title compound of Example 132, Example 139, and Example 142, respectively, and then reducing by the method of Example 33:

| Example | Compound | M.P. |
|---|---|---|
| 165 | 3-Methoxy-N-ethyl-17β-[(4-chlorophenylmethyl)amino]estra-1,3,5(10)-triene (diabetes) | 93.5–95° |
| 166 | 3-Methoxy-N-ethyl-17β-[(2-(4-aminosulfonyl)phenyl)ethyl)-amino]-estra-1,3,5(10)-triene (diabetes) | 125–133° |
| 167 | 3-Methoxy-N-ethyl-17β-[((2-trifluoromethyl)phenylmethyl)amino]-estra-1,3,5(10)-triene (diabetes) | 70.5–75° |

The following compound is prepared by starting with the title compound from Example 154 and hydrocinnamaldehyde and then reducing by the method of Example 33:

| Example | Compound | M.P. |
|---|---|---|
| 168 | 3-Methoxy-N-(3-phenylpropyl)-17β-[(3-phenylpropyl)amino]-estra-1,3,5(10)-triene (diabetes) | 85–90° |

EXAMPLE 169

N-[17β-3-methoxyestra-1,3,5(10)-trien-17-yl]-1,6-hexane-diamine 1,6-Diaminohexane was dissolved in 800 ml of methanol and the pH of the solution was brought to 6.7 with glacial acetic acid. To this was added estrone methyl ether and 800 ml of THF. NaCNBH$_3$ was then added and the solution was heated to 61° C. and kept there overnight. Reaction completion was found by TLC. The solution was made basic with 2M NaOH (1300 ml) to a pH above 12. The solution was then extracted with CH$_2$Cl$_2$ (3×1000 ml) and the combined organic layers were washed with brine, dried (MgSO$_4$), filtered, and concentrated to give a yellow oil. Upon standing in the refrigerator the material turned to a yellow white solid.

The material was passed through a pre-column of 70–230 mesh silica gel and eluted with CHCl$_3$ containing 25% of a MeOH/NH$_4$OH (9/1) mixture. After the solvent was evaporated, the resulting oil was chromatographed on 1840 g of 15–40 μm silica gel and eluted with CHCl$_3$ containing 13% of a MeOH/NH$_4$OH (9/1) mixture. 300 ml fractions were collected with fraction numbers 33–53 being homogeneous by TLC. Fraction numbers 30–32 contained a small amount of the α-isomer and another impurity but were added to the main batch of fractions. Solvent evaporation and trituration with hexane provided an off-white solid which was placed under (0.1 mm) high vacuum for 2 hours to give the title compound, m.p. 93°–94.5° C.

EXAMPLE 170

1H-Pyrrole-2,5-dione,1-[6-[[(17β)-3-methoxyestra-1,3,5(10)-trien-17-yl]amino]hexyl]

The diamine from Example 169 and maleic anhydride were added to a 3-necked round-bottomed flask (2 liter) equipped with a condenser, nitrogen inlet tube, thermometer with thermometer adapter, and magnetic stir bar. Both starting materials were covered with 850 ml of o-xylene, heated to a solution temperature of 144° C. (reflux) and kept there for 1 hour and 15 minutes. Reaction completion was determined by TLC. The solution was allowed to cool and diluted with 1200 ml of CHCl$_3$. The xylene and chloroform were evaporated to give a light brown gum.

This gum was chromatographed on 1840 g of 15–40 μm silica gel eluting with CHCl$_3$ containing 3% of a MeOH/NH$_4$OH (9/1) mixture. Fractions of 400 ml were collected with fractions 11–25 being homogenous by TLC and corresponding to the desired product. Solvent evaporation and trituration with hexane provided a light yellow solid. This solid was placed under high vacuum (0.2 mm) for 2 hours to give the title compound, m.p. 123°–124° C., as confirmed by NMR. (PLA2)

EXAMPLE 171

L-Ornithine, N5-[(17β)-3-methoxyestra-1,3,5(10)-trien-17-yl]monopotassium salt 1.08 g of estrone methyl ether was slurried in 30 ml of THF and 40 ml of methanol. 6 g of 3 Å sieves were added followed by 1.25 g of ornithine methyl ester dihydrochloride dissolved in 20 ml of methanol. The pH was adjusted (25% Et$_3$N/MeOH) to 6.0 and then 237 mg of NaCNBH$_3$ was added in one portion and the reaction mixture was stirred for about 4 days. Reaction progress was monitored by TLC. The product was worked up by filtering through celite, washing the solids with 210 ml of (4:3) MeOH/THF, evaporating under reduced pressure, and then dissolving the white solid in CH$_2$Cl$_2$ and washing it with 2M NaHSO$_4$ until the aqueous layer became acidic (caution HCN). The aqueous acidic layer was separated, made basic with 3M KOH (pH 13), and extracted with CH$_2$Cl$_2$. This was dried over MgSO$_4$, filtered and evaporated under reduced pressure to yield crude product. The entire crude was chromatographed using 50 g of 230–400 mesh silica gel eluting with a CH$_2$Cl$_2$/MeOH solution (10% NH$_4$OH) (9:1), and collected in 3 ml fractions after a 50 ml column volume was voided. Fractions 145–210 yielded the methyl ester.

16 mg of this methyl ester was dissolved in 2 ml of MeOH and 39 µl of a 1.0M KOH solution were added. An additional 2 ml of water was added to the stirred reaction and the reaction progress was monitored by TLC until completion. There followed a workup by evaporation under reduced pressure to produce the title compound. TLC: Rf 0.19 (90:9:1, CH$_2$Cl$_2$/MeOH/NH$_4$OH) (PLA2)

EXAMPLE 172

1H-Pyrrole-2,5-dione,1-[6-[[(17β)-3-methoxyestra-1,3,5(10)-trien-17-yl]amino]hexyl], citrate A flame dried 3-necked 15 ml round-bottomed flask, equipped with a magnetic stir bar, glass stoppers and nitrogen inlet tube, was charged with the title compound from Example 170 and about 3 ml of THF. To this was added citric acid monohydrate which had been completely dissolved in 1.5 ml of MeOH. Stirring at 20°–25° was continued for 30 minutes at which time ether was added dropwise. At least 5 ml of ether was added before a white solid appeared. An additional 2 ml of ether was added to ensure complete recovery of the salt. The mixture was filtered through a F fist funnel to give a white solid. The solid was placed under high vacuum (0.2 mm, 20°–25°) for 4 hours to produce the title compound. MS (M+H)$^+$: 465.3111 (PLA2)

EXAMPLE 173

1H-Pyrrole-2,5-dione, 1-[6-[[(17β)-3-methoxyestra-1,3,5(10)-trien-17-yl]amino]hexyl], methanesulfonate A flame dried 3-necked, 15 ml round-bottomed flask equipped with a nitrogen inlet tube, magnetic stir bar and glass stoppers was charged with the title compound from Example 170 and 3.5 ml of THF. To this was added methanesulfonic acid in 2.5 ml of THF. After about 20 minutes of stirring, a white precipitate formed. To ensure complete formation of the solid, 5 ml of ether was added and stirring was continued another 10 minutes. The mixture was filtered through a fine porosity fritted funnel and the solid washed with one portion of cold THF. This provided a white powder. The solid was placed under high vacuum overnight to produce the title compound, m.p. 200.5°–202.5° C. (PLA2)

EXAMPLE 174

1,3-Propanediamine, N-[3-[[(5α,17β)-androstan-17-yl]amino]propyl]-N,N',N'-trimethyl 0.53 g of 5α-androstan-17-one was slurried in 10 ml of THF and 15 ml of MeOH. 2 g of 3 Å sieves were then added followed by 0.5 g of N,N,N'-trimethyl-N'-(3-aminopropyl)-1,3-propanediamine. The pH was lowered to 6–6.5 with glacial acetic acid, 120 mg of NaCNBH$_3$ was added and the mixture was refluxed for 7 hours. TLC (CH$_2$Cl$_2$/10% NH$_4$OH in MeOH (4:1)) revealed product formation with some contaminants. The reaction mixture was cooled, filtered through Celite wash solids with 1:1 MeOH/THF, evaporated under reduced pressure, and diluted with CH$_2$Cl$_2$. The solution was then made basic with 3M KOH, washed with saturated NaCl solution, dried over MgSO$_4$, filtered and evaporated under reduced pressure to yield crude product. The entire crude product was chromatographed on a medium pressure system comprising 230–700 mesh silica gel (160 g), eluting with CH$_2$Cl$_2$/10% NH$_4$OH in MeOH (6:1). After 140 ml of column volume was voided, 5 ml fractions (#'s 55–150) were collected. NMR confirmed that the title compound was produced. MS (M+H)$^+$: 432.4314 (PLA2)

EXAMPLE 175

Cholane-3,7,11-triol, 24-[[3-(dimethylamino)propyl]amino]

2 g of 3α,7α,12α-trihydroxy-5β-cholanic acid and 0.68 ml of Et$_3$N were dissolved in 100 ml of DMF and then cooled to 0° C. Once cooled, 0.64 ml of isobutyl-chloroformate was added, the mixture was stirred for 15 minutes, and then 0.57 ml of 3-dimethylaminopropylamine in 5 ml of DMF was added. The mixture was allowed to warm to 20°–25° and stirred overnight. TLC (CH$_2$Cl$_2$/10% NH$_4$OH in MeOH (4:1)) revealed product formation. The product was worked up by washing the entire reaction mixture 3 times with water (pH 12–13), washing with saturated NaCl, drying over MgSO$_4$, filtering and evaporating under reduced pressure, to yield crude amide.

957 mg of the crude amide was dissolved in 100 ml of pyridine. To this was added about 2.1 ml of BSTFA followed by refluxing to yield product. The reaction mixture was evaporated under high vacuum to remove all traces of pyridine. 1.5 g of LiAlH$_4$ was slurried in 5 ml of THF. The crude tetra-TMS intermediate was added to this in a dropwise manner in 5 ml of THF and allowed to stir for about 3 days. 45% KOH was added carefully until gassing ceased and the solution was then diluted with THF/ether (300 ml). The Al salts were filtered off, dried over MgSO$_4$, filtered and evaporated under reduced pressure to yield crude product. IR revealed a trace of starting material. NMR (no TMS) revealed that the crude product contained the title compound. The entire crude was dissolved in 5–7 ml of MeOH and then 100 ml of 0.1N HCl was added and the mixture was stirred at 20°–25°. After 1.5 hours TLC (CHCl$_3$/25% NH$_4$OH in MeOH) revealed product formation. The solution was made basic with concentrated NH$_4$OH (pH 9–10) and the entire solution was placed under high vacuum. The resulting residue was chromatographed on 200 g of 70–230 mesh silica gel, and eluted with CHCl$_3$/25% NH$_4$OH in MeOH (4:1). After 200 ml of column volume was collected 5 ml fractions (numbers 105–260) were collected. NMR was consistent with the title compound, m.p. 68°–73° C. (PLA2)

EXAMPLE 176

1H-Pyrrole-2,5-dione, 1-[3-[[3-[(3-methoxyestra-1,3,5(10)-trien-17-yl)methylamino]propyl]methylamino]propyl]

1.0 g of the steroid amine N-(3-aminopropyl)-N'-[(17β)-3-methoxyestra-1,3,5(10)-trien-17-yl]-1,3-propanediamine was dissolved in 30 ml of CHCl$_3$. A solution containing 491 mg of maleic anhydride in 10 ml of THF was then added and the mixture was stirred at 20°–25°. TLC (CHCl$_3$/25% NH$_4$OH in MeOH (4:1)) revealed product formation together with remaining starting material and the di-maleamic acid. Because starting material was present an additional 50 mg of maleic anhydride was added in 1 ml of THF and the mixture was stirred for 30 minutes. Subsequent TLC analysis indicated no starting material present. The reaction mixture was evaporated under reduced pressure to yield a crude product. The entire crude was chromatographed on 285 g of 230–400 mesh silica gel and eluted with $CHCl_3/25\%$ $NH_4OH$ in MeOH (4:1) (medium pressure column). After 500 ml of column volume was collected, 6 ml fractions (numbers 50–82) were collected. NMR was consistent with the desired maleamic acid intermediate.

217 mg of this maleamic acid and 0.33 ml of a 37% aqueous solution of formaldehyde were added to 15 ml of acetonitrile followed by 89 mg of sodium cyanoborohydride. The mixture was stirred at room temperature. TLC revealed about 60% completion of the reaction. Therefore, an additional 0.33 ml of 37% aqueous formaldehyde solution and 89 mg of sodium cyanoborohydride were added and the mixture was stirred at room temperature. TLC revealed the presence of the next crude maleamic acid intermediate and therefore the entire reaction mixture was evaporated under reduced pressure, to yield crude maleamic acid. This crude maleamic acid was chromatographed on 60 g of 230–400 mesh silica gel, eluting with $CHCl_3/25\%$ $NH_4OH$ in MeOH (4:1). After 90 mls of column volume were voided, 3 ml fractions (numbers 38–80) were collected. NMR was consistent with the desired maleamic acid intermediate.

85 mg of this maleamic acid was dissolved in 4 ml of $CHCl_3$. 151 μl of 1.6 mm acetic anhydride was added followed by 46 mg of anhydrous sodium acetate and the mixture was stirred overnight at 20°–25°. TLC revealed product formation which was worked up by evaporation under reduced pressure to yield crude product. The entire crude was chromatographed on a medium pressure system utilizing a 25 g (230–400 mesh) silica gel column, eluted with $CH_2Cl_2/10\%$ $NH_4OH$ in MeOH (8:1). The column volume fraction plus fractions numbers 1–8, yielded the title compound. MS $(M+H)^+$: 508.3570 (PLA2)

EXAMPLE 177

1-Propanol,
3-[[3-[(3-methoxyestra-1,3,5(10)-trien-17-yl)amino]-propyl]amino]

2.9 g of estrone methyl ether was slurried in 55 ml of THF and 80 ml of MeOH. 11 g of 3 Å sieves were then added followed by 2 g of 1-propanol-3-[(3-aminopropyl)amino]. The pH was lowered to 6–6.5 with glacial acetic acid, 628 mg of sodium cyanoborohydride was added and the mixture was refluxed overnight. A sample was removed from the reaction mixture and evaporated under reduced pressure. Several drops of concentrated $NH_4OH$ were added to the sample and it was again evaporated under reduced pressure. $CH_2Cl_2$ was added to this sample and it was filtered, and evaporated under reduced pressure. TLC analysis ($CH_2Cl_2/10\%$ $NH_4OH$ in MeOH (4:1)) revealed product formation with some starting material remaining. The entire reaction mixture was filtered through a pad of celite. The solids were washed with 200 ml of MeOH/THF (4:3), evaporated under reduced pressure and then about 20 ml of concentrated $NH_4OH$ was added to the residue (pH 10) and this was again evaporated under reduced pressure. The entire crude was chromatographed on 285 g of 230–400 mesh silica gel (medium pressure system), eluting with $CH_2Cl_2/10\%$ $NH_4OH$ in MeOH (4:1). After 600 ml of column volume was voided, the following 12 ml fractions were taken: fraction numbers 15–30 yielded the first title compound; NMR confirmed the structure (PLA2). Fraction numbers 95–190 yielded the second title compound; NMR confirmed the structure. MS $(M+H)^+$: 401.3173 (PLA2)

EXAMPLE 178

1H-Pyrrole-2,5-dione,
1-[6-[(3-methoxyestra-1,3,5(10)-trien-17-yl)amino]hexyl]-3,4-dimethyl Following the general procedure of Example 170, but starting with 2,3-dimethylmaleic anhydride, the title compound was produced, mp 79°–80° C. (PLA2-)

EXAMPLE 179

1-Azetidinehexanamine,
N-(3-methoxyestra-1,3,5(10)-trien-17-yl)

0.208 g of diamine from Example 169, 0.415 g of lithium carbonate and 0.114 g of 1,3-dibromopropane were mixed in 5 ml of $CH_3CN$. The mixture was heated in a sand bath to 80° C. overnight. The solution was cooled and made acidic using 1M HCl. After stirring for 10 minutes the solution was made basic with 2M NaOH. This solution was extracted with $CHCl_3$ (2×) and the organic layer was washed with brine and dried ($Na_2SO_4$), filtered and concentrated to provide a yellow oil.

This yellow oil was chromatographed on 35 g of 70–230 silica gel and eluted with $CHCl_3$ containing 8% of a MeOH/$NH_4OH$ (9/1) mixture. An initial fraction of 70 ml was collected followed by 3 ml fractions. Fraction numbers 67–90 were nearly homogeneous by TLC and were combined and concentrated to provide a yellow oil.

This yellow oil was chromatographed on 22 g of 40–60 μm silica gel and eluted with $CHCl_3$ containing 10% of MeOH/$NH_4OH$ (9/1) mixture. An initial fraction of 75 ml was collected followed by 3 ml fractions. Fractions 3–20 contained the desired intermediate product as a yellow oil.

This yellow oil was chromatographed again on the same column and eluted with $CHCl_3$ containing 7.5% of a MeOH/$NH_4OH$ (9/1) mixture. An initial fraction of 85 ml was collected followed by 3 ml fractions. The product came off within the first 85 ml and fractions 1–10. Solvent evaporation provided complete recovery of the material.

The oil was chromatographed a final time on the same column and eluted with $CHCl_3$ containing 3% of a MeOH/$NH_4OH$ (9/1) mixture. An initial fraction of 75 ml was collected followed by 3 ml fractions. Fractions 31–80 were homogeneous by TLC and were combined and concentrated to provide a light yellow oil. This became an off-white solid, m.p. 45°–47° C. NMR was consistent with the desired product. (PLA2)

EXAMPLE 180

Acetamide,
2-chloro-N-[6-[(3-methoxyestra-1,3,5(10)-trien-17-yl)amino]hexyl]

0.154 g of the diamine from Example 169 was added to 2 ml of $CHCl_3$. To this was added $Et_3N$ in 1 ml of CHCl₃. The contents were cooled in an acetone-dry ice bath.

To this was added 53.4 mg of chloroacetyl chloride in 1.5 ml of CHCl₃. After stirring in the dry ice bath for 15 minutes, the solution was allowed to warm to 20°–25°. Following workup a light yellow oily solid was produced.

The yellow oily solid was chromatographed on 22 g of 40–60 μm silica gel eluting with CHCl₃ containing 3% of a MeOH/NH₄OH (9/1) mixture. Two 25 ml fractions were collected followed by 3 ml fractions. Fractions 71–120 were nearly homogeneous by TLC and were combined and concentrated to give a light yellow oil. M.S. results showed that the isolated oil was the title compound. MS (M+H)+: 461.2916 (PLA2)

EXAMPLE 181

Butanediamide,
N'-[5-[[4-[[5-(acetylhydroxyamino)pentyl]amino]-1,4-dioxobutyl]hydroxyamino]pentyl]-N-hydroxy-N-[5-[(3-methoxyestra-1,3,5(10)-trien-17-yl)amino]pentyl]

1.49 g of estrone methyl ether was slurried in 100 ml of THF and 200 ml of MeOH. 47 g of 3 Å sieves were then added followed by 2 g of deferoxamine mesylate salt. The pH was then lowered to 6.0–6.5 with glacial acetic acid and 188 mg of sodium cyanoborohydride was added. This was refluxed for about 4 days. TLC (CHCl₃/25% NH₄OH in MeOH (4:1)) revealed reaction completion. The material was filtered through celite, the solids washed with 200 ml of MeOH, and evaporated under reduced pressure, to yield crude product. The crude product was chromatographed on 1000 g of 70–230 mesh silica gel eluting with CHCl₃/25% NH₄OH in MeOH (4:1). After an initial fraction of 1300 ml was voided, fractions (numbers 1–100) were collected which contained crude product. The crude product was rechromatographed on 100 g of 230–400 mesh silica gel (medium pressure system) eluting with CHCl₃/25% NH₄OH in MeOH (4:1). After a 100 ml column volume was voided, 6 ml fractions were collected. Fraction numbers 8–12 yielded the title compound. MS (M+H)+: 829.5431 (PLA2)

EXAMPLE 182

1H-Pyrrole-2,5-dione,
1-[3-[[3-[(3-methoxyestra-1,3,5(10)-trien-17-yl)amino]propyl]amino]propyl]-, dihydrochloride 2.0 g of the free amine N-(3-aminopropyl)-N'-[(17β)-3-methoxyestra-1,3,5(10)-trien-17-yl]-1,3-propanediamine was dissolved in 9.43 ml of a 0.53M HCl/MeOH solution (5.0 mm) and stirred for 30 min. The MeOH was then blown-off by a stream of nitrogen. 20 ml of CHCl₃ was added followed by 2.64 g of 18-crown-6. This mixture was stirred for 30 min. Then a solution containing 0.7 ml Et₃N and 2.46 g of Boc-ON dissolved in 20 ml of CHCl₃ was added in a dropwise manner over 20 min. This mixture was stirred at 20°–25° overnight. TLC (CHCl₃/10% NH₄OH in MeOH (8:1)) revealed product formation. This material was evaporated under reduced pressure to yield crude product. The entire crude was chromatographed on 285 g of 230–400 mesh silica gel (medium pressure), eluting with CHCl₃/10% NH₄OH in MeOH (8:1). After 750 ml of column volume was collected 7 ml fractions (numbers 60–170) were taken. NMR confirmed the intermediate tBOC-steroid maleamic acid was produced.

1.2 g of the tBoc-steroid so produced was dissolved in 100 ml of o-xylene, 235 mg of maleic anhydride was added and the mixture was heated to reflux. After 1 hour, TLC (CHCl₃/10% NH₄OH in MeOH (8:1)) revealed product formation. The intermediate maleamic acid was also present and therefore refluxing was continued while adding 100 mg of maleic anhydride until some red solid appeared in the reaction flask at which point the reaction was stopped. The reaction mixture was evaporated under a high vacuum to yield crude product. The entire crude was chromatographed on a 230–400 mesh silica gel medium pressure column, eluting with CHCl₃/10% NH₄OH in MeOH (8:1). After 400 ml of column volume was voided, 6 ml fractions (numbers 9–30) were taken containing the tBoc-maleimide as confirmed by NMR.

50 mg of the t-Boc-maleimide was dissolved in a minimal amount of CH₂Cl₂, and then the CH₂Cl₂ was blown off with a stream of N₂. 3 ml of a 2.8M HCl solution in EtOAc was added. After 4 hours, 3 ml more of 2.8M HCl/EtOAc was added and then the mixture was placed in a −78° freezer overnight. The next morning the reaction was stirred for 4 hours at 20°–25°, after which TLC (CHCl₃ (10% NH₄OH in MeOH (8:1)) indicated only a trace of starting material remaining. The solid was filtered and placed on a high vacuum (20°–25°, 0.1 torr) for 2 hours to yield the title compound. MS (M+H)+: 480.3221 (PLA2)

EXAMPLE 183

1,3-Propanediamine,
N-[3-(3-aminopropoxy)estra-1,3,5(10)-trien-17-yl]N,N',N'-trimethyl A flame dried 25 ml two necked round bottomed flask, equipped with a 10 ml constant pressure addition funnel, magnetic stir bar, and nitrogen inlet tube, was charged with the 0.175 g of NaH dispersion. This dispersion was washed three times with hexane; each time the hexane was suctioned out. The NaH was covered with 4 ml of DMF. To this mixture was added 0.401 g of the title compound from Preparation 11 in 10 ml of DMF over a 25 minute period with stirring in a cold water bath. Stirring was then continued at 20°–25° for 1 hour. To this was added 0.332 g of Boc-3-amino-1-propanol mesylate in 2 ml of DMF over a period of 5 minutes. Stirring was continued at 20°–25° for 1 hour. The reaction mixture was poured into ice water, CHCl₃ was added, and the resulting layers separated. The water layer was washed once with CHCl₃. The combined organic layers were washed with brine, filtered, dried (MgSO₄) and concentrated under high vacuum to give a yellow oil.

This oil was chromatographed on 71 g of 70–230 mesh silica gel eluting with CHCl₃ containing 10% of a MeOH/NH₄OH (9/1) mixture. Initial fractions of 25 ml (3) were collected followed by 5 ml fractions (actual column volume was approximately 150 ml). Fraction numbers 39–88 were homogeneous by TLC (CHCl₃ containing 10% of a MeOH/NH₄OH (9/1) mixture) and were combined and concentrated to give a light yellow oil.

A flame dried 2-necked 25 ml round bottomed flask, equipped with a nitrogen inlet tube, rubber stopper and magnetic stir bar, was charged with 0.371 g of this light yellow oil and 10 ml of CH₂Cl₂. To this solution was added 0.67 ml trifluoroacetic acid via syringe. By TLC the reaction appeared nearly complete after 2.5 hours and was worked up. Solvent evaporation gave a yellow oil and a second product.

The combined oils were chromatographed on 70 g of 70–230 mesh silica gel eluting with $CHCl_3$ containing 12% of a $MeOH/NH_4OH$ (9/1) mixture. Initial fractions of 25 ml (6) were collected followed by 5 ml fractions. Fraction numbers 44–90 were nearly homogeneous by TLC and were combined and concentrated to provide the title compound as a light yellow oil. MS $(M+H)^+$: 428.3604 (PLA2)

EXAMPLE 184

1H-Pyrrole-2,5-dione1-[3-[[17-[[3-(dimethylamino)-propyl]methylamino]estra-1,3,5(10)-trien-3-yl]oxy]propyl]

88.9 mg of the title compound from Example 183 and 34.9 mg of maleic anhydride were added to a 10 ml round bottomed flask in 5 ml of o-xylene. The solution was rapidly heated in a sand bath to a temperature of 135°–142° C. By TLC after 0.5 hour the reaction was complete. After cooling the reaction mixture was worked up. Solvent evaporation under high vacuum provided a white solid.

To ensure the product was pure the solid was chromatographed on 22 g of 40–60 μm silica gel eluting with $CHCl_3$ containing 8% of a $MeOH/NH_4OH$ (9/1) mixture. Two fractions of 25 ml were collected followed by 2.5 ml fractions. Fraction numbers 19–43 were nearly homogeneous by TLC ($CHCl_3$ containing 10% of a $MeOH/NH_4OH$ (9/1) mixture). The fractions were combined and concentrated to give the title compound as a white solid, m.p. 117°–120° C. NMR confirmed the production of this compound. (PLA2)

EXAMPLE 185

L-Lysine, N6-(3-methoxyestra-1,3,5(10)-trien-17-yl)

1.1 g of the 3-methyl estrone ether was slurried in 20 ml of THF and 30 ml of MeOH. 4 g of 3 Å sieves was then added followed by 1.51 g of α-tBoc lysine methyl ester. The pH was then lowered with glacial acetic acid to 6.0. Then 243 mg of sodium cyanoborohydride was added and the reaction was refluxed overnight. TLC ($CHCl_3$/10% NH4OH in MeOH (20:1)) revealed product formation. The reaction was stopped, allowed to cool, filtered through celite, washed with (4:3) MeOH/THF (solids) and evaporated under reduced pressure to yield tBOC steriod. The entire crude was chromatographed on 285 g of 230–400 mesh silica gel (medium pressure) column. After 500 ml of column volume was voided, 6 ml fractions (numbers 1–70) were taken. NMR confirmed that the desired tBoc steriod was produced.

50 mg of the tBoc steriod was dissolved in 5 ml of $CH_2Cl_2$ and cooled to 0° C. 2.46 ml of trifluoroacetic acid was then added and the mixture was gradually warmed to 20°–25°. After 2 hours TLC ($CHCl_3$/10% $NH_4OH$ in MeOH (8:1)) revealed product formation. The reaction mixture was evaporated under reduced pressure to yield crude product. The entire crude was chromatographed on 7 g of 70–230 mesh silica gel, eluting with $CHCl_3$/10% $NH_4OH$ in MeOH (8:1). After 5 mls was voided, 1 ml fractions (numbers 16–24) were taken which by TLC contained the desired methyl ester steriod. NMR confirmed its production.

30 mg of the methyl ester steroid was dissolved in 1 ml of MeOH and then 70 μl of 1.0M KOH solution (aqueous) was added. 0.5 ml aliquots of $H_2O$ were then added with stirring overnight until the reaction was complete (about 4.0 ml total). TLC ($CHCl_3$/10% $NH_4OH$ in MeOH (8:1)) revealed product formation. The reaction mixture was evaporated under reduced pressure and azeotroped with $CH_2Cl_2$ (5×) to yield crude product. The entire crude was dissolved in a small volume of $CH_2Cl_2$, and ether was added to produce a filterable solid precipitate. Upon filtering the solid was isolated and was tacky to the touch. The solid was dissolved in $CH_2Cl_2$ and evaporated under pressure, to yield the title compound. NMR confirmed the structure. MS $(M+H)^+$: 453 (PLA2)

EXAMPLE 186

2H-1,4-Diazepin-2-one,hexahydro-4-[3-[(3-methoxyestra-1,3,5(10)-trien-17-yl)amino]propyl]

23 mg of 2-methylimidizole was dissolved in 2 ml of $CH_2Cl_2$ and cooled to −10° C. 15 μl of bromoacetyl bromide was then added and stirred at −10° C.–0° C. for 1 hour. The reaction mixture was warmed to 20°–25° and a solution containing 30 mg of N-(3-aminopropyl)-N'-[(17β)-3-methoxyestra-1,3,5(10)-trien-17-yl]-1,3-propanediamine in 2 ml of $CH_2Cl_2$ was added dropwise over 30 minutes. This was stirred at 20°–25° for 2 hours. TLC ($CHCl_3$/25% $NH_4OH$ in MeOH (4:1)) revealed product formation. The reaction mixture was evaporated under reduced pressure to yield crude product. The entire crude was chromatographed on 8 g of 70–230 mesh silica gel, eluting with $CH_2Cl_2$/10% $NH_4OH$ in MeOH (4:1). After 10 ml of column volume was voided 1 ml fractions were collected. Preparation A: fractions numbers 25–30.

Preparation A was chromatographed with 7–8 g of 230–400 mesh silica gel, eluting with $CH_2Cl_2$/10% $NH_4OH$ in MeOH (6:1). After 5 ml of column volume was voided, 0.5–1.0 ml fractions (numbers 8–18) were taken containing the title compound. By I.R., C-13, 200 $MH_z$ NMR the title compound was produced. MS $(M+H)^+$: 440.3322 (PLA2)

EXAMPLE 187

2-Butenoic acid, 4-[[3-[acetyl[3-[(3-methoxyestra-1,3,5(10-trien-17-yl)amino]propyl]amino]propyl]amino]-4-oxo 100 mg of N-(3-aminopropyl)-N'-[(17β)-3-methoxyestra-1,3,5(10)-trien-17-yl]-1,3-propanediamine was dissolved in 4 ml of $CHCl_3$ and a solution containing 27 mg of maleic anhydride in 1 ml of THF was added. After 1 hr TLC analysis ($CHCl_3$/25% $NH_4OH$ in MeOH (4:1)) revealed some starting amine left. Another 10 mg of maleic anhydride in 0.5 ml of THF was added. After 20 minutes TLC analysis revealed product formation. The reaction mixture was evaporated under reduced pressure and the entire residue was chromatographed on 8 g of 70–230 mesh silica gel, eluting with $CHCl_3$/25% $NH_4OH$ in MeOH (4:1). After 10 ml of column volume was voided, 0.5–1.0 ml fractions (numbers 16–35) were taken which contained the maleamic acid intermediate as confirmed by NMR.

48 mg of this maleamic acid was dissolved in 2 ml of $CHCl_3$, and 16 μl of glacial acetic acid was added and stirred for 15 minutes. 39 μl of acetic anhydride was then added followed by 3–5 mg of $NaO_2C_2H_3$. This mixture was stirred at 20°–25° for 30 minutes. TLC analysis ($CHCl_3$/25% $NH_4OH$ in MeOH (4:1)) revealed product formation. The entire reaction mixture was evaporated under reduced pressure and the white residue was chromatographed on 8 g of 70-230 mesh silica gel, eluting with CHCl3/25% NH4OH in MeOH (4:1). After 10 ml of column volume was voided, 0.5-1.0 ml fractions (numbers 9-14) were taken containing the title compound, mp 121°-23° C. (PLA2)

EXAMPLE 188

L-Lysine, N6-[1-[6-[(3-methoxyestra-1,3,5(10)-trien-17-yl)amino]-hexyl]-2,5-dioxo-3-pyrrolidinyl]-methyl ester Lysine methyl ester dihydrochloride, 2 ml of ethanol, and 0.110 ml Et3N were added together and stirred until the lysine was completely dissolved. This entire solution was added to a heated solution (37°-39° C.) of the title compound from Example 170 and 30 ml of absolute ethanol and stirred for 4 hours. By TLC the reaction was complete.

Water was added to the solution and the pH was raised to 11 using dilute K2CO3 (2%). The solution was extracted with CHCl3 (2×) and the organic phase washed with brine, dried (MgSO4), filtered, and concentrated to provide an oily white solid.

The oily white solid was chromatographed on 22 g of 40-60 μm silica gel eluting with CHCl3 containing 5% of a MeOH/NH4OH (9/1) mixture. Two 25 ml fractions were collected followed by 3 ml fractions. Fraction numbers 69-93 contained the desired product along with impurities. Solvent evaporation provided 0.156 g of a yellow oil. This oil was rechromatographed on 22 g of 40-60 μm silica gel using the same solvent system. After two 25 ml fractions were voided, 3 ml fractions were collected. Fraction numbers 64-83 were collected and solvent evaporation provided the title compound as a light yellow oil product. MS (M+H)+: 625.4346 (PLA2)

EXAMPLE 189

2,5-Pyrrolidinedione
3-methoxy-1-[6-[(3-methoxyestra-1,3,5(10)-trien-17-yl)amino]hexyl]; Butanoic acid,
3-methoxy-4-[[6-[(3-methoxyestra-1,3,5(10)-trien-17-yl)amino]hexyl]amino]-4-oxo-, methyl ester; Butanoic acid,
2-methoxy-4-[[6-[(3-methoxyestra-1,3,5(10)-trien-17-yl)amino]hexyl]amino]-4-oxo-, methyl ester The title compound from Example 170 was heated in MeOH in a sand bath to a temperature of 55° C. After 2 hours the reaction was complete by TLC. The solution was allowed to cool and the MeOH evaporated under reduced pressure to provide a light yellow oil, while in the refrigerator the oil became an off-white semi-solid.

The semi-solid was chromatographed on 22 g of 40-60 μm silica gel eluting with CHCl3 containing 4% of a MeOH/NH4OH (9/1) mixture. Initially, two-25 ml fractions were collected followed by 2.5 ml fractions. Fraction numbers 18-39 were homogeneous by TLC and corresponded to the first title compound (10A) (PLA2). Fraction numbers 45-90 were homogeneous by TLC and corresponded to the second title compound (10B). Fraction numbers 103-123 were homogeneous by TLC and corresponded to the third title compound (10C). The appropriate fractions were combined and concentrated to give an oil for 10A, an oil for 10B, and an oil for 10C. MS (M+H)+: 10A=497.3390, 10B=529.3669, 10C=529.3613 (PLA2).

EXAMPLE 190

N-(5-fluoro-2,4-dinitrophenyl)-N'-[(17β)-3-methoxyestra-1,3,5(10)-trien-17-yl]-1,6-hexanediamine 0.151 g of the title compound from Example 169 was dissolved in 20 ml of MeOH. To this was added 0.6 ml Et2N, followed by 0.312 g 1,5-difluoro-2,4-dinitrobenzene in 10 ml of MeOH. By TLC after 15 minutes the reaction was complete. The solution was diluted with CHCl3 and washed with H2O. The H2O layer was extracted with additional CHCl3 and the combined organic layers were washed with brine and dried (Na2SO4), filtered, and concentrated to give an oil.

The oil was chromatographed on 50 g of 70-230 mesh silica gel eluting with CHCl3 containing 3.5% of a MeOH/NH4OH (9/1) mixture. An initial fraction of 50 ml was collected followed by 5 ml fractions. Fractions 17-45 were homogeneous by TLC and were combined and concentrated to give a semi-solid. NMR was consistent with the desired product. MS (M+H)+: 569.3146

EXAMPLE 191

N-(2,4-dinitrophenyl)-N'-[(17β)-3-methoxyestra-1,3,5(10)-trien-17-yl]-1,6-hexanediamine Following the general procedure of Example 190 but starting with 2,4-dinitrofluorobenzene the title compound is produced, mp 90°-92° C.

EXAMPLE 192

N-[4-(4'-Cyclohexylcyclohexylidene)cyclohexyl]-N-(3-pyridinyl)methylamines and

To a solution of 3-aminomethylpyridine (0.800 ml) and acetic acid (0.65 ml) in methanol (16 ml) was added the title compound from Preparation 19 (1.0 g) and solid sodium cyanoborohydride (0.252 g of 95% quality) in a N2 atmosphere. A vigorous evolution of gas occurred when the hydride was added. TLC after three hours indicated that the reaction was complete. The reaction mixture was poured into aqueous 1N NaOH and the pH of the mixture was adjusted to pH>10. The aqueous mixture was extracted with ether (4×), and the pooled ether extracts were washed with water, dried (Na2SO4), filtered, and concentrated to give a white solid. Chromatography (190 g of 40-63 μm silica gel, 96.3-3-0.2 CHCl3-methanol-ammonium hydroxide, 40 ml fractions) of this solid gave a less polar isomer eluting in fractions 14-18 and a more polar isomer eluting in fractions 20-30.

The less polar isomer was recrystallized from ether-pentane, giving colorless crystals, mp 93.5°-94.5° C.

EXAMPLE 193

N-Benzylestra-1,3,5(10)-trien-17β-amine

To a solution of benzylamine (11.2 ml) in dry methanol (75 ml) was added sequentially acetic acid (6.16 ml), estra-1,3,5(10)-trien-17-one (5.21 g) sodium cyanoborohydride (1.35 g), and THF (60 ml) under a N2 atmosphere. The resulting mixture was stirred overnight at room temperature, concentrated in vacuo, diluted with water (200 ml), and made alkaline with aqueous sodium hydroxide (50 ml). The suspension was extracted with ethyl acetate (3×200 ml) and the combined extracts were dried over MgSO4, filtered and concentrated to an oil. This product was chromatographed (300 g silica gel 0.4-4-96 Et3N-acetone-hexane, 20 ml fractions) and gave impure product in fractions 53-79 and pure product in fractions 80–135. The latter were combined and after removal of the solvent gave the title compound as crystals, mp 71°–74° C. (PLA2, diabetes)

EXAMPLE 194

3-Methoxy-N-[2-(4'-pyridinyl)ethyl]estra-1,3,5(10)-trien-17β-amine

To methanol (110 ml) were added sequentially 4-(2-aminoethyl)pyridine (20.4 g, Reilly), acetic acid (20 ml, 20 g), estrone methylether (9.5 g), sodium cyanoborohydride (2.09 g), and THF (80 ml). The resulting mixture was stirred at room temperature for 30 hours. The now clear solution was concentrated under reduced pressure to a yellow solid residue. Water (300 ml) and aqueous 50% sodium hydroxide were added to the residue and the resulting mixture was extracted 2× with ethyl acetate. The extracts were dried (MgSO$_4$), filtered, and concentrated. A solid yellow residue was obtained. Recrystallization of the solid from acetone gave first crop of crystals, mp 143°–147° C., and a second crop of crystals. Recrystallization of 1.00 g from acetone gave 0.724 g of the title compound as nearly colorless crystals, mp 145°–147° C. (PLA2-, diabetes)

EXAMPLE 195

3-Methoxy-N-[4-(3'-pyridinylmethyl)phenyl]estra-1,3,5(10)-trien-17β-amine dihydrochloride A solution of estrone methyl ether (8.52 g) and 3-(4'-amino)-benzylpyridine (5.52 g) in toluene (100 ml) was heated to reflux temperature. Water in the condensate was collected in a Dean-Stark trap. After 23 hours the solution was concentrated under reduced pressure and methanol (70 ml) and tetrahydrofuran (40 ml) were added to the residue. The resulting solution was stirred at room temperature, sodium cyanoborohydride (3.5 g) and acetic acid (3.6 ml, 3.6 g) were added, and stirring was continued overnight. TLC (10% of 10% NH$_4$OH in CH$_3$OH in CHCl$_3$) showed starting ketone and two more polar components. Stirring another 4 hours with additional sodium cyanoborohydride did not change the TLC picture significantly. Water was added to the reaction solution and the solution was concentrated under reduced pressure, giving a solid residue. Water (200 ml) and 50% aqueous NaOH were added to the residue. The residue was broken up with a spatula and the mixture was extracted with ether (2×), the ether extracts were dried (MgSO$_4$), filtered and concentrated. A gummy, yellow residue was obtained and was chromatographed (395 g silica gel, 30% ethyl acetate in hexane, 45 ml fractions) using low pressure liquid chromatography. The desired product was eluted in fractions 80–122.

A part of the product (4.580 g) was dissolved in ether and ethereal HCl was added. The precipitate was yellow at first but with more HCl, the precipitate became white. The ether was blown off with a stream of N$_2$. The residual solid was crystallized from methanol-ether and gave the title compound, mp 170°–215° C. (PLA2-, diabetes)

EXAMPLE 196

N-Diphenylmethyl-3-methoxyestra-1,3,5(10)-trien-17β-amine

A solution of aminodiphenylmethane (5.50 g) in methanol (100 ml) was stirred at room temperature. Added sequentially to this solution were glacial acetic acid (1.8 ml, 1.8 g), estrone methyl ether (8.52 g), sodium cyanoborohydride (2.3 g), and THF (80 ml). The mixture was stirred at room temperature for 8 days. Additional NaB(CN)H$_3$ (1.5 g), amine (5.5 g), and acetic acid (1.8 g) were added after four days of the reaction time. Excess solvent was removed under reduced pressure and water (300 ml) was added to the solid residue. The mixture was made alkaline with 50% aqueous NaOH and was extracted with ether (3×). The extracts were dried (MgSO$_4$), filtered, and concentrated, giving an oily residue. This crude product was chromatographed (500 g silica gel, 5% ethyl acetate-hexane, 350 ml fractions) on a gravity column. The desired product was eluted in fractions 4–7, and after recrystallization from methanol gave a first crop of crystals, mp 127°–129° C., and a second crop. A sample was recrystallized again from methanol and gave an analytical sample of the title compound, mp 127°–129° C. (PLA2, diabetes)

EXAMPLE 197

N-[2-(2'-Pyridinyl)ethyl]estra-1,3,5(10)-trien-17β-amine

To a solution of 2-(2-amino)ethylpyridine (12.91 ml, 13.2 g) in methanol (75 ml) were added sequentially, under N$_2$, acetic acid (12.31 ml), estrone methyl ether (5.21 g) sodium cyanoborohydride (1.35 g), and tetrahydrofuran (60 ml). The resulting mixture was stirred at room temperature for 40 hours, then concentrated in vacuo, diluted with water (200 ml), and aqueous 50% sodium hydroxide (50 ml). This mixture was extracted with ethyl acetate (3×200 ml) and the combined extracts were dried (MgSO$_4$), filtered and concentrated to a solid. The crude product was chromatographed (300 g silica gel, 0.5% triethylamine/10% acetone/hexane, 30 ml fractions), giving the desired product in fractions 61–142. These fractions were pooled and crystallized from hot hexane to give a first crop of title compound, mp 74°–76° C., and a second crop of title compound. (PLA2)

EXAMPLE 198

N-(3'-Pyridinyl)methylestra-1,3,5(10)-17β-amine

A solution of 3-aminomethylpyridine (10.65 ml) in methanol (75 ml) under N$_2$ was treated sequentially with acetic acid (12.3 ml), estrone methyl ether (5.21 g), sodium cyanoborohydride (1.35 g), and THF (60 ml). The mixture was stirred at room temperature for 24 hours, then concentrated in vacuo, diluted with water (200 ml) and 50% aqueous NaOH, and extracted with ethyl acetate (3×200 ml). The extracts were combined, dried (MgSO$_4$), filtered, and concentrated to a white solid. The crude product was chromatographed on silica gel (320 g) in 0.4% triethylamine/8% acetone/hexane while collecting fractions of 40 ml volume. The desired product was eluted in fractions 163–270, which were combined and crystallized from hot hexane to give the title compound, mp 92°–93° C. (PLA2, diabetes)

EXAMPLE 199

N-[2-(2'-Phenyl)ethyl]-3-methoxy-estra-1,3,5(10)-trien-17β-amine

Phenethylamine (13.33 ml) was dissolved in anhydrous methanol (75 ml) and treated under nitrogen with stirring with glacial acetic acid (6.31 ml), followed by estrone methyl ether (5.97 g), sodium cyanoborohydride (1.38 g, 21 mmoles) and freshly distilled THF (60 ml). The resulting suspension was stirred at 60°±5° under nitrogen for 20 hours, cooled to room temperature, concentrated in vacuo and diluted with water (200 ml) then treated with 50% aqueous sodium hydroxide (50 ml). The resulting suspension was extracted with ethyl acetate (3×200 ml) and the combined extracts were dried over magnesium sulfate, filtered and concentrated to a semi-solid.

The crude product was chromatographed on silica gel (300 g) in 0.75% triethylamine/17.5% acetone/hexane while collecting 40 ml fractions. Fraction numbers 18-21 were concentrated to give a solid; fraction numbers 22-34 were combined and concentrated to give a solid which was recrystallized from hot acetone hexane to give the crystalline title compound, mp 137°-9° C. (PLA2-, diabetes)

EXAMPLE 200

(1'S,2'S)-N-(1',3'-Dihydroxy-1'-phenyl)isopropyl-3-methoxyestra-1,3,5(10)-triene-17β-amine 1S,2S-(+)-2-Amino-1-phenyl-1,3-propanediol (22.26 g) glacial acetic acid (7.61 g), estrone methyl ether (7.20 g), tetrahydrofuran (65 ml) and sodium cyanoborohydride (1.67 g) were added to methanol (88 ml). The resulting mixture was stirred at room temperature for 22 hours. TLC (40% ethyl acetate-hexane) after 44 hours showed remaining starting material and after three days the reaction was completed. Excess solvent was removed under reduced pressure. Water was added and made basis (pH 9) with aqueous 50% NaOH. The cloudy mixture was extracted with ether (3×). The combined extracts were dried (NaSO4), filtered and concentrated to a white solid. TLC showed a polar impurity. The solid was mixed with 33 g of flash silica gel and ethyl acetate. The solvent was removed under reduced pressure and the silica gel was poured on top of the chromatographic column. The compound was eluted with 50% ethyl acetate-hexane. The solid was recrystallized from ethyl acetate to give a first crop of colorless crystals, mp 194°-195° C. A portion of the first crop was recrystallized, mp 192°-193° C. A second crop was obtained, mp 192°-193° C. (PLA2-, diabetes)

EXAMPLE 201

N-(2'-(4''-Hydroxyphenyl)ethyl)-3-methoxyestra-1,3,5-(10)-triene-17β-amine

Tyramine (5.27 g), glacial acetic acid (5.27 g), estrone methyl ether (4.92 g) sodium cyanoborohydride (1.09 g), tetrahydrofuran (43 ml) were added to methanol (58 ml). The reacting mixture was allowed to stir for 21 hours at room temperature. TLC (ethyl acetate) revealed the formation of a more polar product (Rf 0.25). After 19 hours TLC revealed that the starting material still remained in the reaction solution. The system was warmed at 40° C. in an oil bath. The solution remained as a white undissolved solid. After 29 hours the system was allowed to reach room temperature. Excess solvent was removed under reduced pressure. Water was added and made basic (pH 9) with aqueous 50% NaOH. The white solid did not dissolve in ether and was slightly soluble in ethyl acetate. The solid was filtered and mixed with 34 g of flash silica gel and ethyl acetate. The solvent was removed under reduced pressure. The silica gel was poured on top of the chromatographic column. The compound was eluted with ethyl acetate. Solid was obtained and was recrystallized from ethyl acetate, mp 184°-185° C. (diabetes)

EXAMPLE 202

N-Benzyl-5α-androstan-17β-amine

5α-Androstan-17β-amine (10.946 g), glacial acetic acid (2.39 g), sodium cyanoborohydride (0.50 g), benzaldehyde (0.84 g) and tetrahydrofuran (50 ml) were added to methanol (25 ml). The resulting mixture was stirred at room temperature for 48 hours. Excess solvent was removed under reduced pressure. Water was added and made basic (pH 9) with 50% aqueous NMaOH. The mixture was extracted with ether (3×). The combined extracts were dried, filtered and concentrated to a solid. The solid was mixed with 20 g of flash silica gel and dissolved in ethyl acetate. The solvent was removed at reduced pressure and the silica gel was poured on top of the chromatographic column. The compound was eluted with 5% triethylamine-ethylacetate. 6 fractions (200 ml) were collected. An oil was obtained and was dissolved in hot methanol. The solution was cooled giving colorless crystals, mp 85.5°-87.5° C. (PLA2, diabetes)

EXAMPLE 203

N-(3-Dimethylaminopropyl)-N-[2-(2'-fluoro-1',1''-biphen-4'-yl)ethyl]amine

A solution of the title compound from Example 55 (3.28 g) in dioxane (75 ml) was added under N2 to a slurry of LiAlH4 (0.759 g) in dioxane. The resulting mixture was stirred at room temperature for 20 hours after which TLC of a quenched aliquot revealed only starting material. The mixture was heated at 60° C. for 24 hours, additional LiAlH4 (1.14 g) was added, and the mixture was heated at 60° C. for an additional 24 hours. The reaction was cooled in an ice bath and quenched by the careful addition of, first, ethyl acetate and then water. The mixture was filtered through celite and the filtrate layers were separated. The aqueous layer was further extracted with ethyl acetate, the combined extracts were dried (Na2SO4), filtered, and concentrated. The residue was chromatographed over silica gel (40–63 μm, 395 g) using chloroformmethanol-ammonium hydroxide (90-9-1; 50 ml fractions) as the solvent system. The title compound was eluted in fractions 31–42 which contained 0.626 g of oil: IR (liquid film) 2958, 2940, 2894, 2874, 1625, 1484, 1461, 1450, 1418, 1269, 1132, 1041, 836, 767, 725, 698 cm$^{-1}$. (PLA2-, diabetes)

EXAMPLE 204

N-((4'-Chloro)benzyl)-5α-androstan-17β-amine

4-Chlorobenzaldehyde (0.464 g), 5α-androstan-17β-amine (4.40 g), glacial acetic acid (0.99 g), sodium cyanoborohydride (0.21 g) and tetrahydrofuran (5 ml) were added to methanol (11 ml). The resulting mixture was warmed to dissolve the solid in solution and allowed to stir overnight at room temperature. Excess solvent was removed under reduced pressure. Water was added and made basic (pH 9) with 50% aqueous NaOH. The mixture was extracted with ether and the organic layer became cloudy. Celite was used to filter the organic layer. The aqueous layer was washed with ether and the combined organic layers were dried (NaSO4), filtered and concentrated. The crude solid was mixed with 10 g of flash silica gel and dissolved in ethyl acetate. The solvent was removed and the silica was poured on top of the chromatographic column. The compound was eluted with 50% ethyl acetate-hexane. The title compound was obtained as a solid which was recrystallized from acetone (0.364 g) mp 101°-102° C. (PLA2, diabetes)

EXAMPLE 205

N-(4'-Hydroxy-3'-methoxybenzyl)-3-methoxyestra-1,3,5(10)-triene-17β-amine

4-Hydroxy-3-methoxybenzylhydrochloride amine (8.32 g), estrone methyl ether (2.51 g), sodium cyanoborohydride (0.55 g) were added to methanol (30 ml) followed by tetrahydrofuran (22 ml). The solution was allowed to stir for about 4 days at room temperature. TLC (ethyl acetate) revealed the formation of a more polar compound and the presence of some starting material. The solution was heated to reflux for a few more days. TLC revealed the reaction did not complete. Excess solvent was removed at reduced pressure. Water was added and made basic (pH 9) with aqueous 50% NaOH. The solution was extracted with ether (3×). The combined extracts were dried (Na$_2$SO$_4$), filtered and concentrated. The oil was mixed with 20 g of flash silica gel and ethyl acetate. The solvent was removed under reduced pressure and the silica gel was poured on top of the chromatographic column. The compound was eluted with ethyl acetate. The title compound was obtained as a solid and was recrystallized from ethyl acetate (0.488 g), mp 169°-169.5° C. (PLA2, diabetes-)

EXAMPLE 206

N-[(5α,17β)-Androstan-17-yl]-1,6-hexanediamine

A 100 ml round-bottomed flask, equipped with a magnetic stir bar, condenser, and nitrogen inlet tube, was charged with 1,6-hexanediamine (0.904 g) and 15 ml of methanol. The solution was treated with glacial acetic acid until the pH was 6.7. To this mixture was added 15 ml of tetrahydrofuran, 5α-androstan-17-one (0.704 g) and sodium cyanoborohydride (0.228 g). The mixture was heated to reflux for 18 h. After cooling, the solution was made basic with aqueous 2M sodium hydroxide to a pH of 13-14. The solution was extracted with chloroform (3×) and the combined organic layers were washed with water and brine, dried (Na$_2$SO$_4$), filtered, and concentrated to give 1.2 g of an oil.

The oil was chromatographed on 87 g of 230-400 mesh silica gel, eluting with chloroform containing 20% of a methanol/ammonium hydroxide (9/1) mixture. An initial fraction of 150 ml was collected followed by 5 ml fractions. Fractions 12-20 were impure by TLC. These fractions were combined, concentrated, and rechromatographed on the same column eluting with chloroform containing 15% of a methanol/ammonium hydroxide (9/1) mixture. Fractions 18-43 were homogeneous by TLC and were combined with fractions 21-50 which were pure from the first chromatography to give 0.656 g of an oil. IR, n̄max (neat) 2924, 2853, 1470, 1464, 1447, 1158, 827, 797, and 767 cm$^{-1}$.

EXAMPLE 207

1-[6-[[(5α,17β)-Androstan-17-yl]amino]hexyl]-1H-pyrrole-2,5-dione

The title compound from Example 206 (0.393 g) and maleic anhydride (0.180 g) were covered with 12 ml of o-xylene and placed under nitrogen. The mixture was heated with stirring in a sand bath to a temperature of 145°-150° C. for 2 hours. After the mixture had cooled, the solvent was evaporated under high vacuum to give 0.966 g of a semi-solid.

The semi-solid was chromatographed on 50 g of 230-400 mesh silica gel eluting with chloroform containing 5% of a methanol/ammonium hydroxide (9/1) mixture. An initial fraction of 125 ml was collected followed by 5 ml fractions. Fractions 2-40 contained the desired product along with small amounts of lower Rf impurities. The fractions were combined and concentrated to give 0.194 g of a white solid (m.p. >250° C.) IR n̄max (mull) 1706, 1451, 1409, 1392, 843, 833, and 696 cm$^{-1}$.

EXAMPLE 208

3-(3-t-Butoxycarbonyl-aminopropoxy)estra-1,3,5(10)-trien-17-one

A flame dried 1000 ml 3-necked round-bottomed flask, equipped with a nitrogen inlet tube magnetic stir bar, 500 ml constant pressure addition funnel and 125 ml constant pressure addition funnel, was charged with a 60% sodium hydride dispersion (4.80 g). The dispersion was washed with hexane (3×) with the solvent removed by suction. The sodium hydride was covered with 100 ml of dimethylformamide and the estrone (11.1 g) in 250 ml of dimethylformamide was added over 35 minutes. The mixture was stirred at room temperature for 1 hour. The mesylate (13.06 g) in 80 ml of dimethylformamide was added to the above solution over 10 minutes and the mixture stirred an additional 1.5 hours.

The reaction mixture was poured slowly and carefully into ice water. The aqueous solution was extracted with hexane/ethyl acetate (1/1) and then chloroform. The organic phase was washed with brine, dried (MgSO$_4$), filtered, and concentrated to give 18.4 g of an oil. The oil was chromatographed on 1600 g of 230-400 mesh silica gel eluting with chloroform/acetone (99/1). An initial fraction of 300 ml was collected followed by 45 ml fractions. Fractions 88-97 and 118-140 contained impure product as determined by TLC. These fractions were combined, concentrated, and rechromatographed on 300 g of 230-400 mesh silica gel eluting with the same solvent. After collecting a 450 ml fraction, 8 ml fractions were collected. Fractions 71-126 were homogeneous by TLC and were combined with fractions 98-117 from the first chromatography to give 6.15 g of a powder (m.p. 134°-136° C.).

EXAMPLE 209

N/[(17β)-3-[3-t-Butoxycarbonyl-aminopropoxy]estra-1,3,5(10)-trien-17-yl]-1,3-propanediamine A 25 ml round-bottomed flask, equipped with a magnetic stir bar, condenser, and nitrogen inlet tube, was charged with 1,3-propanediamine (0.31 ml, d=0.888) and 7.5 ml of methanol. The solution was treated with glacial acetic acid until the pH was 6.6. To this mixture was added 7.5 ml of tetrahydrofuran, the title compound from Example 208 (0.518 g), and sodium cyanoborohydride (97.1 mg). The mixture was heated to reflux for 5½ hours. After cooling the solution was made basic with aqueous 2M sodium hydroxide to a pH of 13-14. The solution was extracted with chloroform (3×) and the organic phase washed with water and brine, dried (Na$_2$SO$_4$), filtered, and concentrated to give 0.836 g of a colorless oil.

The oil was chromatographed on 85 g of 230-400 mesh silica gel eluting with chloroform containing 10% of a methanol/ammonium hydroxide (9/1) mixture. An initial fraction of 130 ml was collected followed by 5 ml fractions. Fractions 86-100 were impure by TLC. These fractions were combined, concentrated, and rechromatographed on the same column eluting with chloroform containing 12-15% of a methanol/ammonium hydroxide (9/1) mixture. Using the same fraction size, fractions 21-40 were homogeneous by TLC and were combined with fractions 101-134 from the first chromatography to give, after trituration with hexane, 0.387 g of a solid (m.p. 87.5°-89.5° C.).

EXAMPLE 210

1,3-Propanediamine,N-[3-(3-aminopropoxy)estra-1,3,5(10)-trien-17-yl]-, trihydrochloride A flame dried 25 ml 2-necked round-bottomed flask equipped with a nitrogen inlet tube, rubber septum, and magnetic stir bar, was charged with the title compound from Example 209 (0.123 g) and 10 ml of ethyl acetate. To this was added 0.3 ml of methanol to completely dissolve the starting material. A 2.8M solution of HCl in ethyl acetate was added via syringe (0.4 ml). Over a period of 4½ hours additional HCl-ethyl acetate (1.5 ml) was added. By TLC after 4½ hours the reaction was complete. The addition of ether to ensure precipitation formed a finely divided solid which was difficult to filter. Therefore the solvent was evaporated under reduced pressure and the resulting solid triturated with hexane. The collected solid was dried under high vacuum overnight to provide 117 mg of a white solid (m.p. 277°-281° C.). (PLA2)

EXAMPLE 211

[U-75733F] 1,3-Propanediamine, N-[3-(3-aminopropoxy)estra-1,3,5(10)trien-17-yl]-, tris(trifluoroacetate)

A flame dried 25 ml 2-necked round-bottomed flask equipped with a nitrogen inlet tube, magnetic stir bar, and rubber septum, was charged with the title compound from Example 209 (0.102 g), 5 ml of methylene chloride, and trifluoroacetic acid (0.25 ml). By TLC after 2 hours the reaction was complete with only a minor impurity. Addition of ether precipitated out the salt which was collected using a fine frit scintered glass funnel. The solid was dried under high vacuum overnight to provide 140 mg of a powder (m.p. 203°-207° C.). (PLA2)

EXAMPLE 212

N-[(17β)-3-[3-t-Butoxycarbonyl-aminopropoxy]estra-1,3,5(10)-trien-17-yl]-1,6-hexanediamine A 50 ml round-bottomed flask, equipped with a magnetic stir bar, condenser, and nitrogen inlet tube, was charged with 1,6-hexanediamine (0.437 g) and 10 ml of methanol. The solution was treated with glacial acetic acid until the pH was 6.6. To this mixture was added 10 ml of tetrahydrofuran, the title compound from Example 208 (0.509 g), and sodium cyanoborohydride (0.11 g). The mixture was heated to reflux for 5 hours. After cooling the solution was made basic with aqueous 2M sodium hydroxide to a pH of 13-14. The solution was extracted with chloroform and the organic phase washed with water and brine, dried (Na₂SO₄), filtered, and concentrated to give 0.962 g of an oil.

The oil was chromatographed on 85 g of 230-400 mesh silica gel eluting with chloroform containing 15% of a methanol/ammonium hydroxide (9/1) mixture. An initial fraction of 130 ml was collected followed by 5 ml fractions. Fractions 34-46 were impure by TLC. These fractions were combined, concentrated, and rechromatographed on the same column eluting with chloroform containing 10% of a methanol/ammonium hydroxide (9/1) mixture. An initial fraction of 130 ml was collected followed by 5 ml fractions. Fractions 27-63 were homogeneous by TLC and were combined with fractions 47-60 from the first chromatography to give 0.492 g of an oil. In another trial trituration with hexane gave a white solid (m.p. 82°-84° C.).

EXAMPLE 213

1,6-Hexanediamine, N-[3-(3-aminopropoxy)estra-1,3,5(10)-trien-17-yl]-,trihydrochloride A flame dried 25 ml 2-necked round-bottomed flask equipped with a nitrogen inlet tube, rubber septum, and magnetic stir bar, was charged with the title compound from Example 212, (0.118 g) and 10 ml of ethyl acetate. To this was added 0.3 ml of methanol to completely dissolve the starting material. A 2.8M solution of HCl in ethyl acetate was added via syringe (1.3 ml) followed by an additional 1.3 ml of the HCl-ethyl acetate solution over a 3 hour period. After a total reaction time of 6½ hours ether was added to ensure complete precipitation of the salt. The salt was collected using a fine frit sintered glass funnel and dried under high vacuum overnight to provide 106 mg of a solid (m.p. 265°-270° C.). (PLA2)

EXAMPLE 214

1-[6-[[(17β)-3-[3-t-Butoxycarbonyl-aminopropoxy]estra-1,3,5(10)-trien-17-yl]amino]hexyl]-1H-pyrrole-2,5-dione The title compound from Example 212 (0.301 g) and maleic anhydride (94.7 mg) were covered with 15 ml of o-xylene and placed under nitrogen. The solution was refluxed for 4 hours. After cooling, the solvent was evaporated under high vacuum to give 0.67 g of an oil.

The oil was chromatographed on 70 g of 70-230 mesh silica gel eluting with chloroform containing 5% of a methanol/ammonium hydroxide (9/1) mixture. An initial fraction of 100 ml was collected followed by 5 ml fractions. Fractions 10-30 were homogeneous by TLC and were combined and concentrated to give, after trituration with hexane, 0.162 g of a yellow solid (m.p. 103°-105° C.).

EXAMPLE 215

Acetic acid, trifluoro-, compd. with 1-[6-[[3-(3-aminopropoxy)estra-1,3,5(10)-trien-17-yl]amino]hexyl]-1H-pyrrole-2,5-dione(2:1)

A flame dried 25 ml round-bottomed flask, equipped with a nitrogen inlet tube and magnetic stir bar, was charged with the title compound from Example 214 (0.136 g) and 6 ml of methylene chloride. To this solution was added trifluoroacetic acid (0.21 ml, d=1.48). After stirring at room temperature for almost 2 hours additional trifluoroacetic acid (0.1 ml) was added to complete the reaction. After a total reaction time of 3 hours, ether was slowly added to precipitate the salt. The salt oiled out. The solvent was evaporated under reduced pressure. After repeated attempts at forming a solid by trituration with ether a light yellow foam was obtained. This salt was placed under high vacuum for 24 hours to give 0.160 g of solid. IR, nmax (mull) 1707, 1672, 1611, 1501, 1411, 1367, 1203, 1179, 1134, 832, 799, and 696 cm$^{-1}$. (PLA2)

EXAMPLE 216

N-t-Butoxycarbonyl-6-amino-1-hexanol, methanesulfonate t-Butoxycarbonyl formation: 6-Amino-1-hexanol (3.13 g) was dissolved in 150 ml of tetrahydrofuran. To this was added di-t-butyldicarbonate (5.87 g) in 20 ml of tetrahydrofuran over several minutes. The solution was stirred at room temperature for 50 minutes. The solvent was evaporated under reduced pressure and the resulting oil taken up in ethyl acetate. The organic solution was washed with aqueous 5% sodium hydroxide and brine, dried (MgSO$_4$), filtered, and concentrated to give 5.77 g of an oil. The product was pure by TLC. (Rf=0.55 in ethyl acetate/hexane [7/3]).

Mesylate formation: The entire oil from the previous reaction was taken up in 100 ml of methylene chloride and placed under nitrogen. The solution was cooled in a carbon tetrachloride-dry ice bath (−20° C.). Addition of triethylamine (3.91 g) in one portion was followed by addition of methanesulfonyl chloride (2.4 ml, d=1.48) over several minutes. By TLC after 35 minutes the reaction was complete. The reaction was quenched with ice water and the layers separated. The organic layer was washed with dilute aqueous sodium bicarbonate and brine, dried (Na$_2$SO$_4$), filtered, and concentrated to give 7.69 g of a solid (m.p. 48°–49.5° C.).

EXAMPLE 217

N-[(17β)-3-[6-t-Butoxycarbonyl-aminohexoxy]estra-1,3,5(10)-trien-17-yl]-N,N',N'-trimethyl-1,3-propanediamine A flame dried 25 ml 2-necked round-bottomed flask, equipped with a nitrogen inlet tube, 10 ml constant pressure addition funnel, and magentic stir bar, was charged with a 60% dispersion of sodium hydride (58 mg). The dispersion was washed with hexane (3×), the hexane being removed by suction through a gas dispersion tube. The sodium hydride was covered with 3 ml of dimethylformamide. Addition of the title compound from Preparation 11 (0.202 g) in 8 ml of dimethylformamide was carried out over 15 minutes. After stirring for 1 hour at room temperature the boc-mesylate (0.196 g) in 2 ml of dimethylformamide was added. By TLC after 1½ hours the reaction was only 20% complete. The solution was heated in an oil bath to a temperature of 55° C. overnight. After cooling the reaction was poured into ice water and the aqueous solution was extracted with chloroform (3×). The combined organic layers were washed with brine, dried (MgSO$_4$), filtered, and concentrated under high vacuum to give 0.401 g of an oil.

The oil was chromatographed on 59 g of 230–400 mesh silica gel eluting with chloroform containing 7% of a methanol/ammonium hydroxide (9/1) mixture. An initial fraction of 125 ml was collected followed by 5 ml fractions. Fractions 76–92 were impure by TLC and were rechromatographed on 22 g of 230–400 mesh silica gel eluting with chloroform containing 6% of a methanol/ammonium hydroxide (9/1) mixture. An initial fraction of 50 ml was collected followed by 5 ml fractions. Fractions 14–21 were homogeneous by TLC and were combined with fractions 66–75 from the first chromatography to give 106 mg of a colorless oil. NMR (CDCl$_3$; TMS): δ 7.3–7.15, 6.85–6.6, 4.8–4.5, 4.05–3.85, 2.25, 1.45, 0.8

EXAMPLE 218

Acetic acid, trifluoro-, compd. with N-[3-[(6-aminohexyl)oxy]estra-1,3,5(10)-trien-17-yl]-N,N',N'-trimethyl-1,3-propanediamine (3:1)

A flame dried 25 ml round-bottomed flask, equipped with a nitrogen inlet tube and magnetic stir bar, was charged with the title compound from Example 217 (0.106 g) and 6 ml of methylene chloride. To this solution was added trifluoroacetic acid (0.25 ml, d=1.48). After 2 hours the reaction was 80% complete by TLC. However, after 5 hours at room temperature there was still 5–10% unreacted starting material. Additional trifluoroacetic acid (0.15 ml) was added and stirring continued for 45 minutes. To precipitate out the salt, ether was added, but the salt oiled out. Solvent evaporation and trituration with hexane and ether still provided an oil. By TLC there remained—5% starting material. The oil was again taken up in methylene chloride and trifluoroacetic acid (0.2 ml) was added. After 2 hours at room temperature there remained—5% of starting material. Solvent evaporation and concentration provided 0.184 g of an oil. IR: ñmax (neat) 3035, 2941, 2869, 1779, 1744, 1676, 1612, 1501, 1477, 1428, 1203, 1185, 1140, 837, 799, 722, and 707 cm$^{-1}$. (PLA2)

EXAMPLE 219

N6-(3-Methoxyestra-1,3,5(10)-trien-17-yl)-N-t-boc-lysine, methyl ester

A 100 ml, 3-necked flask, equipped with a magnetic stirrer, was flame dried and then cooled in a nitrogen atmosphere. The flask was charged with 1.1 g of estrone 3-methyl ether dissolved in 20 ml of tetrahydrofuran and 30 ml of methanol. The solution was treated with 4 g of 3A molecular sieves followed by 1.51 g of α t-boc lysine. The pH of the slurry was adjusted to 6.0 with glacial acetic acid. The slurry was then treated with 243 mg of sodium cyanoborohydride and the reaction mixture refluxed for 18 hours. The reaction mixture was filtered through Celite and the solids washed with 200 ml of methanol/tetrahydrofuran (4:3). The filtrate was concentrated in vacuo.

The crude product (4.6 g) was chromatographed on 285 g of 230–400 mesh silica gel. The column was packed and eluted with 95:4.5:0.5 chloroform/methanol/concentrated ammonium hydroxide. An initial fraction of 500 ml was collected followed by 6 ml fractions.

Based of their TLC homogeneity, fractions 1–70 were combined affording 1.1 g of title compound. NMR (CDCl$_3$, TMS) δ 7.3–7.1, 6.8–6.5, 5.25–5.0, 4.5–4.05, 3.8, 3.75, 3.0–1.0, 1.5 and 0.75 ppm.

EXAMPLE 220

N6-(3-Methoxyestra-1,3,5(10)-trien-17-yl), L-lysine, methyl ester

A 10 ml, 2-necked flask, equipped with a magnetic stirrer, was flame dried and then cooled in a nitrogen atmosphere. The flask was charged with 50 mg of the title compound from Example 219 dissolved in 5 ml of methylene chloride. The solution was cooled to 0° C. The solution was then treated with 2.46 ml of trifluoroacetic acid and stirred at room temperature for 2 hours. The reaction mixture was concentrated in vacuo.

The crude product (89 mg) was chromatographed on 7 g of 70–230 mesh silica gel. The column was packed and eluted with (89:10:1) chloroform/methanol/concentrated ammonium hydroxide. An initial fraction of 5 ml was collected followed by 1 ml fractions. Based on their TLC homogeneity, fractions 16–24 were combined affording 31 mg of the title compound. NMR (CDCl$_3$, TMS): δ 7.25–7.1, 6.75–6.5, 3.75, 3.7, 3.0–1.0 and 0.7 ppm.

EXAMPLE 221

1H-Pyrrole-1-acetic acid, 2,5-dihydro-α-[4-[(3-methoxyestra-1,3,5(10)-trien-17-yl)amino]butyl]-2,5-dioxo-, methyl ester A 25 ml, 2-necked flask, equipped with a magnetic stirrer, was flame dried and then cooled in a nitrogen atmosphere. The flask was charged with 163 mg of the title compound from Example 220 slurried in 20 ml of o-xylene. The solution was treated with 45 mg of maleic anhydride, and the reaction mixture was refluxed for 2 hours. The reaction mixture was allowed to cool and then concentrated in vacuo.

The crude product (143 mg) was chromatographed on 25 g of 230–400 mesh silica gel. The column was packed and eluted with (95.2:4.3:0.5) chloroform/2-propanol/concentrated ammonium hydroxide. An initial fraction of 40 ml was collected followed by 2 ml fractions. Based on their TLC homogeneity, fractions 9–20 were combined affording 64 mg of the title compound. NMR (CDCl$_3$, TMS): δ 7.25–7.0, 6.8–6.5, 4.8–4.5, 3.75, 3.7, 3.0–1.0 and 0.75 ppm. (PLA2)

EXAMPLE 222

1H-Pyrrole-2,5-dione1-[3-[(3-methoxyestra-1,3,5(10)-trien-17-yl)amino]-propyl]

A 25 ml, 2-necked flask, equipped with a magnetic stirrer, was flame dried and then cooled in a nitrogen atmosphere. The flask was charged with 246 mg of the first title compound from Example 68, slurried in 15 ml of o-xylene. The solution was treated with 106 ml of maleic anhydride, and the reaction mixture was refluxed for 45 minutes and then concentrated in vacuo.

The crude product (360 mg) was chromatographed on 30 g of 230–400 mesh silica gel. The column was packed and eluted with (95:4.5:0.5) chloroform/methanol/concentrated ammonium hydroxide. An initial fraction of 140 ml was collected followed by 5 ml fractions. Based on their TLC homogeneity, fractions 1–130 were combined affording 98 mg of impure title compound. The 98 mg of impure title compound was rechromatographed on 25 g of 230–400 mesh silica gel. The column was packed and eluted with (96.4:3.2:0.4) chloroform/2-propanol/concentrated ammonium hydroxide. Based on their TLC homogeneity, fractions 19–45 were combined affording 48 mg of title compound, m.p. 105–106. (PLA2)

EXAMPLE 223

1,6-Hexanediamine, N-estra-1,3,5(10)-trien-17-yl 1,6-Hexanediamine (1.2 g) was dissolved in 20 ml of methanol and the pH of the solution was lowered to 6.6 with glacial acetic acid. To this solution was added 500 mg of estra-1,3,5(10-trien-17-one) and 20 ml of THF. Then 166 mg of sodium cyanoborohydride was added and the reaction was brought to reflux. After 7 hours TLC (CHCl$_3$/10% NH$_4$OH in MeOH (9:1)) revealed product formation with no starting material present. The solution was made basic with concentrated NH$_4$OH and dried by evaporation to produce 2.3 g of crude product. The entire crude was chromatographed on 100 mg of 230–400 mesh silica gel, eluting with CHCl$_3$/10% NH$_4$OH in MeOH (9:1). After 150 ml was collected, 7 ml fractions were taken. Fraction numbers 32–90 yielded 492 mg of the title compound. MS C$_{24}$H$_{39}$N$_2$ Meas. 355.3082. (PLA2)

EXAMPLE 224

1,3-Propanediamine, N-[(17β)-3-[3-(dimethylamino)propoxy]estra-1,3,5(10)-trien-17-yl]-N,N',N'-trimethyl A flame dried 50 ml 2-necked round-bottomed flask, equipped with a nitrogen inlet tube, 10 ml constant pressure addition funnel, and magnetic stir bar, was charged with a 60% dispersion of sodium hydride (0.113 g). The dispersion was washed with hexane (3×), the hexane being removed by suction through a gas dispersion tube. The sodium hydride was covered with 5 ml of dimethylformamide and the title compound from Preparation 11 (0.338 g) in 10 ml of dimethylformamide was added over 15 minutes. After stirring for 1 hour at room temperature, the solid azetidine salt (0.307 g) from Preparation 10 was added. After an additional 3½ hours, another portion of the azetidine salt (50 mg) was added and stirring continued overnight. The reaction contents were poured into ice water and the aqueous solution was extracted with chloroform (3×). The combined organic layers were washed with brine, dried (MgSO$_4$), filtered, and concentrated under high vacuum to give 0.416 g of a semi-solid.

The semi-solid was chromatographed on 60 g of 230–400 mesh silica gel eluting with chloroform containing 4–6% of a methanol/ammonium hydroxide (9/1) mixture. An initial fraction of 90 ml was collected followed by 5 ml fractions. Fractions 137, 138, and 150–170 contained impure product by TLC and were rechromatographed on the same column eluting with chloroform containing 6% of a methanol/ammonium hydroxide (9/1) mixture. An initial fraction of 100 ml was collected followed by 5 ml fractions. Fractions 5–15 were nearly homogeneous by TLC and were combined with fractions 139–149 from the first chromatography to give 0.253 g of a colorless oil. IR: nmax (neat) 1610, 1501, 1461, 1382, 1313, 1282, 1256, 1237, 1179, 1155, 1061, 1042, 1011, and 841 cm$^{-1}$. (PLA2)

EXAMPLE 225

17β-t-Butyldimethylsilyloxy-5α-estran-3-one 10 g of 17β-hydroxy-5α-estran-3-one was dissolved in 150 ml of DMF. 3.7 g of imidazole were then added and the mixture was cooled to 0° C. 6.5 g of t-butyl dimethyl silyl chloride were added and the mixture was stirred and gradually warmed to room temperature followed by stirring for two days. TLC (hexane/EtOAc (9:1)) revealed that the reaction was complete. The reaction mixture was diluted with water and then extracted with 500 ml of hexane/EtOAc (9:1) (2×). The combined organic layers were washed with brine, dried over MgSO$_4$, filtered, and evaporated under reduced pressure to produce crude product (14.6 g). The entire crude yield was flash chromatographed with the Aldrich flash chromatography system. The 600 ml column was filled with 7 inches of 230–400 mesh silica gel, eluting with hexane/EtOAc (10:1). Once the sample was loaded, 30 ml fractions were taken. Fraction numbers 4–13, yielded 14 g of the title compound, m.p. 103°–104° C.

EXAMPLE 226

17β-t-Butyldimethylsilyloxy-5α-estran-3α(and 3β)-ol 14 g of the title compound from Example 225 was dissolved in 100 ml of $CH_2Cl_2$, diluted with methanol (750 ml) and cooled to 0° C. 7.0 g of $NaBH_4$ was added in portions until TLC (hexane/EtOAc (9:1)) no longer revealed starting material. Excess $NaBH_4$ was quenched by adding 2M $NaHSO_4$ until gassing ceased (pH of 4). The mixture was diluted with water and EtOAc and the organic layer was separated. The aqueous layer was extracted with EtOAc and the combined extracts were then washed with water and brine, dried over $MgSO_4$, filtered, and evaporated under reduced pressure to yield crude product (15.3 g). The entire crude was chromatographed on 1000 g of 230–400 mesh silica gel eluting with $CH_2Cl_2$/acetone (98:2). After 1200 ml of column volume was collected, 17 ml fractions were taken. Fraction numbers 130–210 yielded 3.2 g of the α-isomer; m.p. 160°–162° C. Fraction numbers 280–430 yielded 10.9 g of the β-isomer, m.p. 135°–138° C.

EXAMPLE 227

17β-t-Butyldimethylsilyloxy-5α-estran-3β-ol, 3-(2-cyanoethyl)ether 5.1 g of title compound from Example 226 was dissolved in 100 ml of benzene (stored over 4 Å sieves). 1.7 ml of acrylonitrile (purified according to "Purification of Laboratory Chemicals," D. D. Perrin et al., pp. 87–88) was then added followed by 0.24 ml of Triton B and the mixture was stirred at room temperature. TLC (hexane/EtOAc (5:1)) revealed product formation, approximately 70–80% complete. The crude product was diluted with EtOAc, washed with water and brine, dried over $MgSO_4$, filtered, and evaporated under reduced pressure to produce crude product (5.82 g). The entire crude was chromatographed on 430 g 70–230 mesh silica gel, eluting with hexane/EtOAc (5:1). After 500 ml was collected, 18 ml fractions were collected. Fractions 45–90 yield 4.43 g of the title compound. MS $C_{27}H_{48}NO_2S$: Theory 446.3454, Measured 446.3480.

EXAMPLE 228

3β,17β-Dihydroxy-5α-estrane, 3-(2-cyanoethyl)ether (3α-)-4.4 g of the cyano-ether steroid from Example 227 was dissolved in 10 ml of $CH_2Cl_2$ and then diluted with 200 ml of MeOH. 40 ml of $CH_2Cl_2$ was then added and the reaction mixture became slightly turbid. 32 ml of a methanolic 3.2M HCl solution (final reaction concentration 0.4M) was then added. After 20 minutes, TLC (hexane/EtOAc (3:1)) revealed that the reaction was complete. The product was then diluted with water and EtOAc, washed again with water and then with brine, dried over $MgSO_4$, filtered and evaporated under reduced pressure to produce crude product (3.73 g). The entire crude was flash chromatographed on 8 inches of 230–400 mesh silica gel, eluting with $CH_2Cl_2$/acetone (98:2), collecting 25 ml fractions. Fraction numbers 8–25, yield 3.2 g of title compound. MS [M+] 331 found 331.

EXAMPLE 229

3β-Hydroxy-5α-estran-17-one, 3-(2-cyanoethyl)ether

The same for the (3α)-isomer 1.0 g of the cyano ether steroid from Example 228 was dissolved in 20 ml of acetone and then cooled to 0° C. 1.0 ml of Jones Reagent was then added and this was stirred at 0° C. for 45 minutes. TLC ($CH_2Cl_2$/acetone (98:2)) showed no starting material and the reaction was quenched with approximately 5 ml of 2-PrOH. The reaction mixture was then diluted with water and EtOAc. The organic layer was separated and washed with water and brine, dried over $MgSO_4$, filtered and evaporated under reduced pressure to produce crude product (1.1 g). MS $C_{21}H_{31}NO_2$: Theory 329.2355, Measured 329.2342.

EXAMPLE 230

Propanenitrile, 3-[[3β,5α)-17-[[6-aminohexyl)amino]estran-3-yl]oxy]

1.78 g of 1,6-Hexanediamine was dissolved in 30 ml of MeOH and the pH of the solution was adjusted to 6.0 with glacial acetic acid. To this solution was added 990 mg of the β cyano ether ketone from Example 229 and 30 ml of THF, followed by 251 mg of sodium cyanoborohydride. The reaction mixture was then refluxed overnight. TLC ($CHCl_3$/10% $NH_4OH$ in MeOH (4:1)) revealed product formation with a trace of starting material remaining. The entire reaction mixture was worked by evaporating under reduced pressure to produce crude product (7.98 g). The entire crude was chromatographed on 285 g of 230–400 mesh silica gel, eluting with $CHCl_3$/10% $NH_4OH$ in MeOH (4:1). After 425 ml was collected, 11 ml fractions were taken. Fraction numbers 20–140 yielded 1.05 g of product. MS $C_{27}H_{48}N_3O$: Theory 430.3786, Measured 430.3797. (PLA2)

EXAMPLE 231

Propanenitrile, 3-[[(3α,5α)-17-[(6-aminohexyl)-amino]estran-3-yl]oxy]

Following the procedure of Example 230 but starting with the α-cyano ether ketone, the title compound is produced. MS $C_{27}H_{48}N_3O$: Theory 430.3797, Measured 430.3786. (PLA2)

EXAMPLE 232

1,6-Hexanediamine, N-[(3β,5α)-3-(3-aminopropoxy)estran-17-yl]

106 mg of lithium aluminum hydride was slurried in 25 ml of ether, and a solution containing 300 mg of the cyano ether steroid from Example 230 in 45 ml of ether was added in a dropwise manner. The solution was then refluxed for 2 hours. TLC ($CHCl_3$/15% $NH_4OH$ in MeOH (4:1)) revealed product formation. The reaction was quenched with 212 ml of water and 170 ml of a 10% NaOH solution and was stirred overnight. The next morning the white solid was filtered and then washed with hot $CHCl_3$. The filtrate was then evaporated under reduced pressure to yield crude product (275 mg). The entire crude was chromatographed on 60 g of 230–400 mesh silica gel, eluting at first with $CHCl_3$/4.2M $NH_3$ in MeOH (95:5) for 5 column volumes (375 ml) then followed by $CHCl_3$/4.2M $NH_3$ in MeOH (9:1). Three ml fractions were then taken. Fraction numbers 141–230 yielded 216 mg of product. MS $C_{27}H_{52}N_3O$: Theory 434.4110, Measured 434.4152. (PLA2)

EXAMPLE 233

1,6-Hexanediamine,
N-[(3α,5α)-3-(3-aminopropoxy)estran-17-yl]

Following the procedure of Example 232, but starting with the cyano ether steroid of Example 231, the title compound is produced. MS $C_{27}H_{52}N_3O$: Theory 434.4110, Measured 434.4144. (PLA2)

EXAMPLE 234

1,3-Propanediamine,
N'-[(3β,5α)-3-2-cyanoethoxy)estran-17-yl)-N,N-dimethyl 460 mg of N,N-Dimethylpropyldiamine was dissolved in 10 ml of MeOH and the pH of the solution was adjusted to 6.0 with glacial acetic acid. To this solution was added 297 mg of the α or β-cyano ether steroid from Example 229 and 10 ml of THF, followed by 75 mg of sodium cyanoborohydride. The reaction mixture was refluxed overnight. TLC ($CHCl_3/4.2M$ $NH_3$ in MeOH (12:1)) revealed product formation with a trace of starting material remaining. The reaction mixture was evaporated under reduced pressure to produce crude product (2.88 g). The entire crude was chromatographed on 100 g of 230–400 mesh silica gel, eluting first with $CHCl_3/4.2M$ $NH_3$ in MeOH (15:1) for 1¾ column volumes (250 ml), then followed by $CHCl_3/4.2M$ $NH_3$ in MeOH (15:1). Five ml fractions were then taken. Fraction numbers 3–50 yielded 173 mg of product. MS [M+] 415, Found 415.

EXAMPLE 235

1,3-Propanediamine,
N'-[(3β,5α)-3-2-cyanoethoxy)estran-17-yl)-N,N-dimethyl]-N,N,N'-trimethyl 170 mg of the α or β-cyano ether steroid from Example 234 was dissolved in 2 ml of acetonitrile and the pH was lowered to 6.5 with glacial acetic acid. 0.16 ml of a 37% formaldehyde solution was then added followed by 41 mg of sodium cyanoborohydride. The reaction mixture was stirred overnight at room temperature. TLC ($CHCl_3/4.2M$ $NH_3$ in MeOH (12:1)) revealed product formation with a trace of starting material present. The reaction mixture was evaporated under reduced pressure to produce crude product (287 mg). The entire crude was chromatographed on 25 g of 230–400 mesh silica gel, eluting with $CHCl_3/4.2M$ $NH_3$ in MeOH (17:1). After 55 ml of column volume was collected, 3 ml fractions were taken. Fraction numbers 3–13 yielded 122 mg of product. MS [M+] 429, Found 429.

EXAMPLE 236

1,3-Propanediamine,
N-[(3β,5α)-3-(3-aminopropoxy)estran-17-yl]-N,N'N'-trimethyl 42 mg of lithium aluminum hydride was slurried in 10 ml of dry ether and a solution containing 121 mg of the β-cyano ether steroid from Example 236 was dissolved in 20 ml of ether. After the addition was completed, the mixture was refluxed for 2 hours. TLC ($CHCl_3/4.2M$ $NH_3$ in MeOH (12:1)) revealed product formation. The reaction mixture was quenched with 84 μl of water and 67 μl of 10% NaOH solution and stirred overnight. The precipitate formed was filtered and then washed several times with hot $CHCl_3$. The combined filtrate was evaporated under reduced pressure to produce crude product (104 mg). The entire crude was chromatographed on 25 g of 230–400 mesh silica gel, eluting with $CHCl_3/4.2M$ $NH_3$ in MeOH (15:1). After 50 ml of 1 column volume was collected, 2 ml fractions were taken. Fraction numbers 23–90 yielded 97 mg of product. MS $C_{27}H_{52}N_3O$: Theory 434.4110, Measured 434,4144. (PLA2)

EXAMPLE 237

1,3-Propanediamine,
N-[(3α,5α)-3-(3-aminopropoxy)estran-17-yl]-N,N'N'-trimethyl

Following the procedure of Example 236, but starting with the α-cyano ether steroid of Example 235, the title compound is produced. MS $C_{27}H_{52}N_3O$: Theory 434.4110, Measured 434.4144.

EXAMPLE 238

1,3-Propanediamine,
N'-[(3β,5α)-3-2-cyanoethoxy)estran-17-yl)-N,N-dimethyl 100 mg of the β-cyano ether steroid from Example 229 and 153 mg of 3-dimethylaminopropylamine were placed in a 10 ml 2-necked flask. 68 μl of 95% formic acid were then added and the reaction mixture was heated to 150° C. The reaction was heated at 130° C. for about 5 to 10 minutes and the temperature gradually increased to 150° C. within 30 minutes. Then the reaction was heated an additional 1 hour. TLC ($CHCl_3/10\%$ $NH_4OH$ in MeOH (7:1)) revealed product formation. The reaction mixture was removed from the oil bath, allowed to cool, diluted with $CHCl_3$, transferred and evaporated under reduced pressure to product crude product (253 mg). The entire crude was chromatographed on 7 g of 230–400 mesh silica gel, first eluting with $CHCl_3/10\%$ $NH_4OH$ in MeOH (10:1). After 10 ml of column volume was collected 1 ml fractions were taken. Fraction numbers 14–25 yielded 103 mg (105A). Since the separation was poor the 105A was rechromatographed on 7 g of 230–400 mesh silica gel, eluting with $CHCl_3/10\%$ $NH_4OH$ in MeOH (19:1). After 10 ml of column volume was collected 1 ml fractions were taken. Fraction numbers 25–34 yielded 4/7 mg of impure product (105B).

The entire 47 mg of 105B was placed on 8 g of 230–400 mesh silica gel column, eluting with $CHCl_3/4.2M$ $NH_3$ in MeOH (99:1). After 10 ml of column volume was collected, 40-4 1 ml fractions were collected. Then 90-1 ml fractions of $CHCl_3/4.2M$ $NH_3$ in MeOH (98:2) were collected. TLC analysis revealed the upper Rf impurities were separated. Finally the solvent polarity was increased to $CHCl_3/4.2M$ $NH_3$ in MeOH (97:3) and fractions were collected. Fraction numbers 185–245 yielded 19 mg of product. MS [M+] 415, Found 415.

EXAMPLE 239

1,3-Propanediamine,
N'-[(3β,5α)-3-(3-aminopropoxy)estran-17-yl]-N,N-dimethyl 7 mg of lithium aluminum hydride was slurried in 2 ml of ether and a solution containing 19 mg of the cyano ether from Example 238 in 7 ml of ether was added. Once the addition was completed, the reaction mixture was refluxed for 2 hours. TLC ($CHCl_3/5\%$ $NH_4OH$ in MeOH (4:1)) revealed product formation with a trace of starting material. Therefore, 1.4 μl of water and 1.1 μl of a 10% NaOH solution were added and the reaction mixture was stirred overnight. The ether solution and white precipitate were filtered and the precipitate was washed several times with hot CHCl₃. The filtrate was evaporated under reduced pressure to produce the crude product (19.7 mg). The entire crude was chromatographed on 7 g of 230–400 mesh silica gel, eluting with CHCl₃/4.2M NH₃ in MeOH (95:5) for 5 column volumes and then eluted with CHCl₃/4.2M NH₃ in MeOH (9:1) collecting 2 ml fractions. Fraction numbers 26–50 yielded 12 mg of product. MS $C_{26}H_{50}N_3O$: Theory 420.3954, Measured 420.3956. (PLA2)

EXAMPLE 240

1H-Pyrrole-1-acetamide,
2,5-dihydro-N-[6-[(3-methoxyestra-1,3,5(10)-trien-17-yl)amino]hexyl]-2,5-dioxo-, monohydrochloride 100 mg of the title compound from Example 76 and 72 mg of the p-nitro ester nitrophenyl succinimidoylacetate were dissolved in 3 ml of DMF and stirred at room temperature for 18 hours. TLC (CHCl/10% NH₄OH in t-PrOH (10:1) revealed product formation. The reaction mixture was diluted with water, extracted several times with CHCl₃, and the organic layer was separated, washed with saturated NaCl, dried over MgSO₄, filtered, and evaporated under reduced pressure (high vacuum) to produce crude product (130 mg). The entire crude was chromatographed on 25 g of 230–400 mesh silica gel eluting with CHCl₃/ 10% Et₃N in 2-PrOH (4:1). After 50 ml of column volume was collected, 2-3 ml fractions were taken. The entire mixture of components came out on the first column volume as well as the first 10 fractions. This was combined to yield 75 mg. Another chromatography was performed, the same procedure was followed with one exception, the solvent system was CHCl₃/10% Et₃N in 2-PrOH (10:1), after 50 ml was collected, 2-3 ml fractions were taken. Fraction numbers 45–55 yielded 47 mg of crude product. MS $C_{31}H_{44}N_3O_4$: Theory 522.3332, Measured 522.3309.

The entire 47 mg of crude product was dissolved in a minimum amount of CHCl₃ (approximately 1 ml). Then a 2.8M HCl in EtOAc solution (1 ml) was added with stirring. After 15 minutes at room temperature the reaction mixture was still clear, therefore, 15 ml of n-hexane was added and the resulting light yellow solid was isolated. Upon filtration it was noted that the solid was tacky, therefore a nitrogen atmosphere was placed around the filtration apparatus. The 47 mg was placed in the vacuum desicator overnight at 0.1 torr and room temperature. The yield after vacuum desication was 17 mg. (PLA2)

EXAMPLE 241

1H-Pyrrole-2,5-dione,
1-[3-[(3-methoxyestra-1,3,5(10)-trien-17-yl)oxy]-propyl]

100 mg of the amine ether steroid 3-[(3-methoxyestra-1,3,5(10)-trien-17-yl)oxy]-1-propanamine and 34 mg of maleic anhydride were slurried in 10 ml of o-xylene and refluxed for 1 hour. TLC (CHCl₃/4.2M NH₃ in MeOH (12:1)) revealed all starting material gone. After 2 hours total reflux the reaction was stopped and allowed to stand for 2 days. TLC (CHCl₃/25% NH₄OH in MeOH (4:1)) revealed that the maleiamic acid was formed. The reaction mixture was placed on the high vacuum, evaporated under reduced pressure to produce crude product (120 mg).

The 120 mg of maleamic acid was slurried in 2 ml of xylene and 1 ml DMF, 9 mg of Amberlyst 15 resin were added and the reaction mixture was heated to reflux. After 3 hours of reflux, TLC (CHCl₃/4.2M NH₃ in MeOH (12:1) revealed no product formation, therefore the mixture was refluxed overnight. TLC in CHCl₃/25% NH₄OH in MeOH (4:1) revealed product formation and that some of the maleamic acid was present. The reaction was cooled and then was evaporated under reduced pressure under high vacuum to produce crude product (129 mg). The entire crude was chromatographed on 25 g of 230–400 mesh silica gel eluting with 100% CHCl₃. After 50 ml (1 column volume) was collected, 2 ml fractions were taken. Fraction numbers 3–9 yielded 10 mg of product. MS $C_{26}H_{33}NO_3$: Theory 423.2409, Measured 423.2386. (PLA2-)

EXAMPLE 242

Propanenitrile,
3-[(3-methoxyestra-1,3,5(10)-trien-17-yl)oxy]

1.16 g of the 17β-alcohol steroid estradiol, 3-methyl ether was dissolved in 20 ml of benzene (stored over 4 Å sieves). 0.53 ml acrylonitrile (purified according to "Purification of Laboratory Chemicals," D. D. Perrin et al. pp. 87–88) was then added followed by 73 μl of Triton B and the mixture was stirred at room temperature for 2 days. TLC (hexane/EtOAc (5:1)) revealed product formation with a trace of starting material present. The crude product was worked up by diluting with EtOAc and brine. The aqueous layer was made acidic with 2M NaHSO₄ and the organic layer was separated, dried over MgSO₄, filtered, and evaporated under reduced pressure to produce crude product (1.51 g). The entire crude was chromatographed on 285 g of 230–400 mesh silica gel, eluting with CH₂Cl₂/hexane (2:1). After 500 ml was collected, 12 ml fractions were taken. Fraction numbers 120–220 yielded 1.4 g of product. MSM⁺ 339 found 339.

EXAMPLE 243

1-Propanamine,
3-[(3-methoxyestra-1,3,5(10)-trien-17-yl)oxy]

626 mg of lithium aluminum hydride was slurried in 150 ml of dry ether and a solution containing 1.4 g of the cyano ether steroid from Example 242 in 300 ml of dry ether. After the addition was completed the mixture was refluxed for 2 hours. TLC (CHCl₃/4.2M NH₃ in MeOH (12:1)) revealed product formation but starting material was still present. An additional 626 mg of LiAlH₄ was added. After 30 minutes TLC revealed about 75% completion. The reaction mixture was refluxed for 1½ hours, after which TLC indicated no starting material left. 2.5 ml of water was added carefully followed by 2.0 ml of a 10% sodium hydroxide solution. The mixture was stirred overnight. The reaction mixture was filtered and the solids washed several times with hot CHCl₃. The combined organic filtrate was then evaporated under reduced pressure to produce crude product (1.53 g). The entire crude was chromatographed on 285 g of 230–400 mesh silica gel, eluting with CHCl₃/4.2M NH₃ in MeOH (24:1). After 475 ml (1 column volume) was collected, 12 ml fractions were taken. Fraction numbers 193–210 yielded 566 mg. MS $C_{22}H_{34}NO_2$: Theory 344.2589, Measured 344.2603

EXAMPLE 244

Acetamide, 2-bromo-N-[3-[(3-methoxyestra-1,3,5(10)-trien-17-yl)oxy]propyl]

100 mg of the amino ether steroid from Example 243 was dissolved in 8 ml of THF and cooled to 0° C. Then a solution containing 65 mg of the succinimide N-(α-bromoacetoxy)-succinimide in 4 ml of THF was added. The mixture was stirred. After 1 hour at 0° C. the mixture was gradually warmed to room temperature. After 1-2 hour, TLC ($CHCl_3$/4.2M $NH_3$ in MeOH (24:1)) revealed product formation with only a trace of starting material present. The reaction mixture was evaporated under reduced pressure to produce crude product (167 mg). The entire crude was chromatographed on 25 g of 230-400 mesh silica gel, eluting with $CHCl_3$/4.2M $NH_3$ in MeOH (24:1). After 40 ml was collected (0.8 column volume), 1.5-2.0 ml fractions were taken. Fraction numbers 3-9 yielded 102 mg of product. MS $C_{24}H_{35}BrNO_3$ Theory 464.1801, Measured 464.1790.

EXAMPLE 245

17β-[(2-(4-Aminosulfonylphenyl)ethyl)amino]-5α-androstand Hemihydrate

A solution of 3.39 g of 4-(2-aminoethyl)benzenesulfonamide in 50 ml of MeOH and 150 ml of THF was acidified with 3 ml (3.15 g) of acetic acid. Then 2.32 g of 5α-androstan-17-one was added. After a solution was obtained, 1.2 g of sodium cyanoborohydride was added. The resulting solution was stirred for 5 hours. An additional 1.2 g of sodium cyanoborohydride was added. The stirring was continued for 19 hours. The solvent was evaporated from the solution. The residue was treated with 200 ml of water, made basic with 50% NaOH solution, and extracted with $CH_2Cl_2$ (3×100 ml). The combined extracts were washed with 50 ml of brine and dried over $MgSO_4$. Evaporation of the solvent left 3.75 g of solid. The solid was chromatographed on a 400 g column of silica gel. The column was eluted with 10% MeOH-$CH_2Cl_2$ and 100 ml fractions were collected. The fractions were assayed by silica gel TLC (1×4″) (10% MeOH-$CH_2Cl_2$). Fractions 18-30 were combined and crystallized from MeOH-$H_2O$ giving 0.76 g of the title compound.

Some of the compounds of the present invention also are useful as angiogenic and angiostatic compounds, i.e., compounds that stimulate or inhibit growth of blood vessels respectively. These activities may be assayed by the methods described in J. Folkman, et al., Science, 221, pp. 719-25 (1983).

The preferred compounds for angiogenic use as assayed in the absence of heparin include 1-[6-[[(17β)-3-methoxyestra-1,3,5(10)-trien-17-yl]amino]hexyl]-1H-pyrrole-2,5-dione, N-[3-(N'-morpholino)propyl]-3-methoxyestra-1,3,5(10)-trien-17β-amine, 3-methoxy-N-(3'-pyridinylmethyl)estra-1,3,5(10)-trien-17β-amine, N-[3-(dimethylamino)propyl]-3-methoxy-N-methylestra-1,3,5(10)-trien-17β-amine, N-[3'-(dimethylamino)propyl]-3-methoxy-N-methylestra-2,5(10)-dien-17β-amine, and 1-[6-[(3-methoxyestra1,3,5(10)-trien-17-yl)amino]hexyl]-3,4,-dimethyl-1H-pyrrole-2,5-dione.

The preferred compounds for angiostatic use include N-(5-fluoro-2,4-dinitrophenyl)-N'-[(17β)-3-methoxyestra-1,3,5(10)-trien-17-yl]-1,6-hexanediamineand N-(2,4-dinitrophenyl)-N'-[(17β)-3-methoxyestra-1,3,5(10)-trien-17-yl]-1,6-hexanediamine.

The angiostatic compounds of the present invention are useful in treating the following diseases and injuries: head trauma, spinal trauma, septic or traumatic shock, stroke, and hemorrhagic shock. In addition, utility in cancer as well as other disorders or physiological phenomena dependent on angiogenesis such as embryo implantation (antifertility), arthritis, and atherosclerosis is exhibited with these compounds optionally co-administered with oral heparin or systemic heparin fragments (see J. Folkman, et al., supra).

The angiostatic compounds can be administered orally, intramuscularly, intravenously and by suppository, and the effective dosage range is 10 to 1500 mg/kg/day. The compounds of the present invention may be coadministered with low doses of glucocorticoids. For the treatment of cancer including head tumors and other conditions dependent upon angiogenesis a preferred dosage range of the angiostatic compounds is 50 to 500 mg/kg/day for 30 days repeated for 30 additional days after a 30 day respite or on a chronic intermittent basis such as every other day therapy until tumor regression or absence of metastases is observed. The preferred route of administration is orally, by suppository or intramuscularly. For the treatment of arthritis the preferred dosage range of the angiostatic compounds is 10 to 250 mg/kg/day or every other day until absence or significant reduction in associated symptoms is observed. For the treatment of atherosclerosis the preferred dosage range of the angiostatic compounds is 10 to 250 mg/kg/day or every other day chronically. And, for the disruption of or prevention of embryo implantation the preferred dosage range of the angiostatic compounds is 10 to 250 mg/kg/day chronically to fertile women. When coadministering an angiostatic compound with heparin or a heparin fragment in practicing the present invention the amount of heparin or heparin to be utilized varies from 1,000 to 50,000 units/kg/day with heparin being administered orally and heparin fragments being administered subcutaneously, orally, intramuscularly or intravenously.

The utility of the compounds of the present invention can be demonstrated in various test models as follows: For head trauma, mice are struck on the head with a standard weight which is dropped from a set height. They are then dosed subcutaneously with the test compound. After one hour the motor abilities of the mice are assessed. Active test compounds promote improved motor activity relative to controls. For spinal trauma, see E. D. Hall and J. M. Braughler, Surg. Neurol. 18, 320-327 (1982) and J. Neurosurg. 56, 838-844 (1982). Septic (traumatic) shock is demonstrated in a rat model whereby test compound is administered and protection of the rats from the lethal effects of endotoxin is measured. For stroke, the carotid arteries of gerbils are ligated for a brief period after which test compound is administered subcutaneously. The behavior of the gerbils is observed after a recovery period, and gerbils receiving test compound display a more normal behavior after the recovery period. And for hemorrhagic shock, by published procedures used to evaluate glucocorticoids. The inhibition of angiogenesis associated with tumor formation and proliferation is typically evaluated in the chick embryo or rabbit cornea, e.g., as reported by J. Folkman, et al., supra.

Sterile aqueous solutions of the angiostatic compounds typically will contain other components such as preservatives, anti-oxidants, chelating agents, or other stabilizers. Suitable preservatives can include benzyl alcohol, the parabens, benzalkonium chloride, or benzoic acid. Anti-oxidants such as sodium bisulfite, ascorbic acid, propyl 3,4,5-trihydroxy benzoate, and the like may be employed. Chelating agents such as citrate, tartrate, or ethylenediaminetetraacetic acid (EDTA) may be used. Other additives useful as stabilizers of corticosteroid prodrugs (e.g., creatinine, polysorbate 80, and the like) may be employed.

Sterile aqueous solutions of the angiostatic compounds can be administered to the patient being treated, i.e., a warm blooded mammal, including humans, intramuscularly or intravenously or orally. Additionally conventional solid dosage forms of the angiostatic compounds can be administered orally to the patient being treated. For example, capsules, pills, tablets or powders of the angiostatic compounds can be formulated in unit dosage forms incorporating conventional fillers, dispersants, preservatives and lubricants. Also suppositories providing a sustained release of an angiostatic compound can be formulated using conventional inert materials such as biodegradable polymers or synthetic silicones.

Heparin fragment means any part of the heparin compound having substantially the same type of anti-angiogenic activity as heparin.

-continued
CHART A

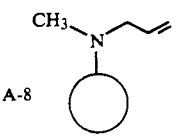
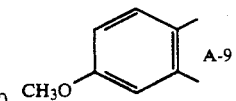

Step A-7 | Li/NH$_3$

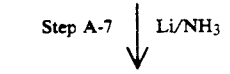

Step A-8 | H$_3^+$O

CHART B

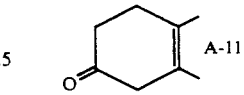

Step B-1 | H$_2$N—R, NaB(CH)H$_3$  |  Step B-1 | H$_2$N—(R)—NH$_2$, NaB(CN)H$_3$

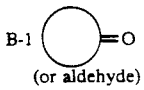

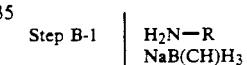 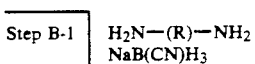

CHART C

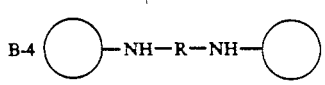

Step C-1 | SOCl$_2$

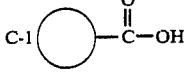

Step C-2 | NH$_2$—R

Step A-2 | LiAlH$_4$

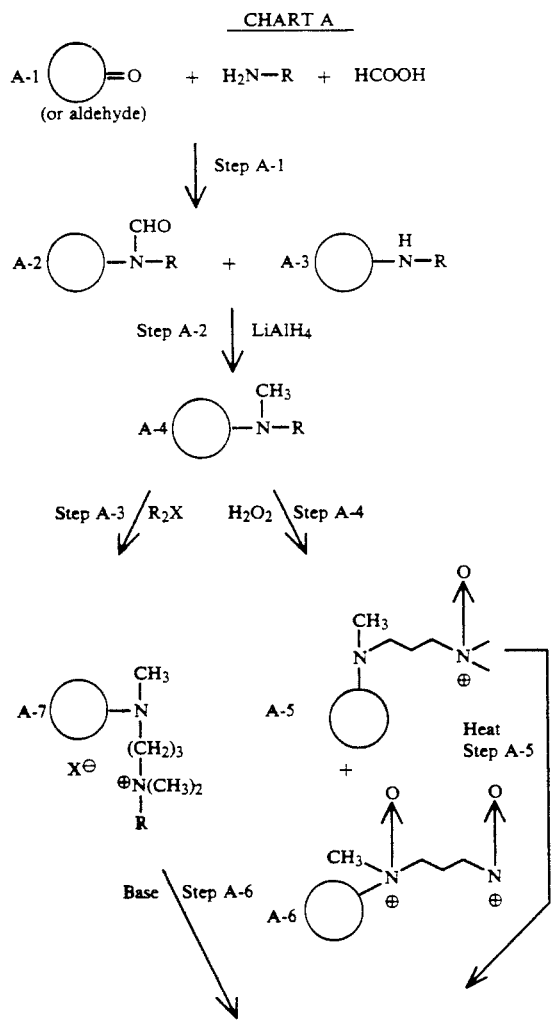

-continued
CHART C

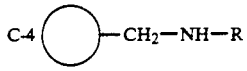

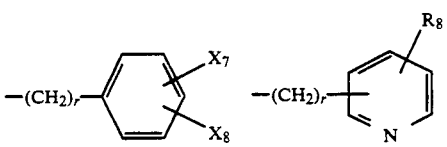

CHART D

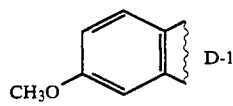

Step D-1 | $(C_6H_5)_2$—PH/n-$C_4H_7$Li

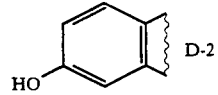

Step D-2
$K_2CO_3$

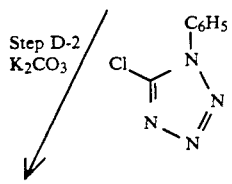

Step D-3 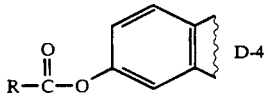

Step D-4 | $BrNH\overset{O}{\underset{\|}{C}}CH_3$

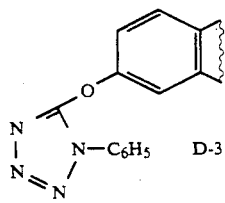

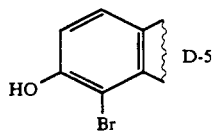

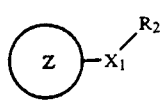

I claim:
1. A compound of the formula

Formula I wherein Z is 4-bicyclohexenylcyclohexyl,
wherein $X_1$ is $NR_1$;
wherein $R_1$ is —CH($CH_2OH$)—CH(OH) (phenyl), —CH(-phenyl)$_2$, -(phenyl)—$CH_2$-(3-pyridinyl), or

wherein $R_8$ is hydrogen;
wherein $X_7$ and $X_8$ are the same or different and are hydrogen, —$CH_3$, —$CF_3$, halogen, —OH, —OCH₃, —NO₂, —NR₄R₄, —SO₂N(R₃) (R₄), —CO₂R₄, —CON(R₃) (R₄), —CH₂N(R₃) (R₄), or tetrazolyl;

wherein $R_2$ is hydrogen, or -$C_1$-$C_3$ alkyl;

wherein $R_3$ and $R_4$ are hydrogen, -$C_1$-$C_2$ alkyl, —CH₂OH, or nothing;

wherein r is 1-8; and pharmacologically acceptable salts thereof.

2. A compound according to claim 1 wherein wherein $R_1$ is

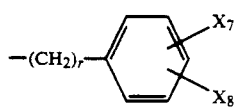

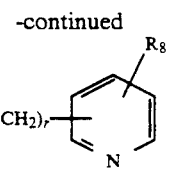

CH(CH₂OH)—CH(OH) (phenyl), —CH(phenyl)₂, -(phenyl)—CH₂(3-pyridinyl);

wherein $R_8$ is hydrogen;

wherein $X_7$ and $X_8$ are the same or different and are hydrogen, halogen, OH, or OCH₃;

wherein $R_2$ is hydrogen;

wherein r is 1-8; and pharmacologically acceptable salts thereof.

3. A compound according to claim 2, consisting of: N-(4-(4'-cyclohexylcyclohexylidene)cyclohexyl)-N-(3-pyridinyl)methylamine.

* * * * *